(12) United States Patent
Yoshida et al.

(10) Patent No.: US 10,547,009 B2
(45) Date of Patent: Jan. 28, 2020

(54) ORGANIC ELECTROLUMINESCENT ELEMENT, ELECTRONIC DEVICE AND COMPOUND

(71) Applicant: IDEMITSU KOSAN CO., LTD., Chiyoda-ku (JP)

(72) Inventors: Kei Yoshida, Sodegaura (JP); Ryohei Hashimoto, Sodegaura (JP); Toshinari Ogiwara, Sodegaura (JP); Yuichiro Kawamura, Sodegaura (JP); Masatoshi Saito, Sodegaura (JP)

(73) Assignee: IDEMITSU KOSAN CO., LTD., Chiyoda-ku (JP)

( * ) Notice: Subject to any disclaimer, the term of this patent is extended or adjusted under 35 U.S.C. 154(b) by 203 days.

(21) Appl. No.: 15/557,681

(22) PCT Filed: Mar. 18, 2016

(86) PCT No.: PCT/JP2016/058877
§ 371 (c)(1),
(2) Date: Sep. 12, 2017

(87) PCT Pub. No.: WO2016/158540
PCT Pub. Date: Oct. 6, 2016

(65) Prior Publication Data
US 2018/0053901 A1    Feb. 22, 2018

(30) Foreign Application Priority Data

Mar. 27, 2015 (JP) .................................. 2015-067466

(51) Int. Cl.
*H01L 51/00* (2006.01)
*C07D 403/10* (2006.01)
(Continued)

(52) U.S. Cl.
CPC ........ *H01L 51/0067* (2013.01); *C07D 403/10* (2013.01); *C07D 403/14* (2013.01);
(Continued)

(58) Field of Classification Search
None
See application file for complete search history.

(56) References Cited

U.S. PATENT DOCUMENTS

2008/0145699 A1    6/2008 Yabe et al.
2009/0191426 A2    7/2009 Yabe et al.
(Continued)

FOREIGN PATENT DOCUMENTS

JP    2010-278287 A    12/2010
JP    2011-49512 A    3/2011
(Continued)

OTHER PUBLICATIONS

Leung et al. "Novel Ambipolar Orthogonal Donor-Acceptor Host for Blue Organic Light Emitting Diodes" Org. Lett. 2013, 15(18), 4694-4697. (Year: 2013).*

(Continued)

*Primary Examiner* — Robert S Loewe
(74) *Attorney, Agent, or Firm* — Oblon, McClelland, Maier & Neustadt, L.L.P.

(57) ABSTRACT

An organic electroluminescence device includes an anode, an emitting layer, and a cathode, the emitting layer including a delayed-fluorescent first compound represented by a formula (1), and a fluorescent second compound. In the formula (1), $Ar_1$ is a substituted or unsubstituted aryl group having 6 to 30 ring carbon atoms and the like, and $Ar_{EWG}$ is a substituted or unsubstituted heteroaryl group having 5 to 30 ring atoms and including one or more nitrogen atom in the ring, or an aryl group having 6 to 30 ring carbon atoms and (Continued)

substituted by one or more cyano group, at least one of $Ar_1$ and $Ar_X$ being at least one group selected from the group consisting of groups represented by a formula (1a) and the like.

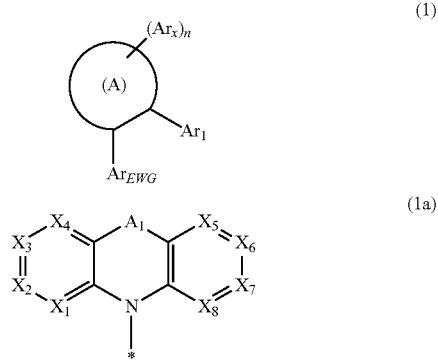

19 Claims, 6 Drawing Sheets

(51) Int. Cl.
  *C07D 403/14* (2006.01)
  *C09K 11/06* (2006.01)
  *H01L 51/50* (2006.01)

(52) U.S. Cl.
  CPC .......... *C09K 11/06* (2013.01); *H01L 51/0072* (2013.01); *C09K 2211/1007* (2013.01); *C09K 2211/1018* (2013.01); *H01L 51/5012* (2013.01); *H01L 51/5056* (2013.01); *H01L 51/5072* (2013.01)

(56) References Cited

U.S. PATENT DOCUMENTS

| | | | |
|---|---|---|---|
| 2011/0121268 A1* | 5/2011 | Nagao | H01L 51/0054 257/40 |
| 2012/0126692 A1 | 5/2012 | Ise et al. | |
| 2013/0240796 A1 | 9/2013 | Parham et al. | |
| 2014/0061548 A1 | 3/2014 | Montenegro et al. | |
| 2014/0070146 A1 | 3/2014 | Parham et al. | |
| 2015/0349286 A1* | 12/2015 | Forrest | C09K 11/06 252/301.16 |
| 2016/0072076 A1 | 3/2016 | Stoessel et al. | |
| 2016/0197286 A1* | 7/2016 | Kawamura | C09K 11/06 257/40 |

FOREIGN PATENT DOCUMENTS

| | | | |
|---|---|---|---|
| JP | 2014-503502 A | 2/2014 | |
| JP | 2014-527022 A | 10/2014 | |
| JP | 5669163 B1 | 2/2015 | |
| JP | 2016-36025 A | 3/2016 | |
| JP | 2016-46417 A | 4/2016 | |
| WO | 2006/067976 A1 | 6/2006 | |
| WO | 2012/153780 A1 | 11/2012 | |
| WO | 2013/038650 A1 | 3/2013 | |
| WO | 2014/092083 A1 | 6/2014 | |
| WO | 2014/106524 A2 | 7/2014 | |
| WO | WO 2014/146752 A1 | 9/2014 | |
| WO | 2014/183080 A1 | 11/2014 | |
| WO | 2015/022835 A1 | 2/2015 | |
| WO | 2015/029964 A1 | 3/2015 | |
| WO | 2016/017514 A1 | 2/2016 | |
| WO | 2016/017684 A1 | 2/2016 | |
| WO | 2016/017688 A1 | 2/2016 | |
| WO | 2016/017741 A1 | 2/2016 | |
| WO | 2016/017757 A1 | 2/2016 | |
| WO | 2016/017760 A1 | 2/2016 | |
| WO | 2016/159479 A1 | 10/2016 | |

OTHER PUBLICATIONS

Machine translation of WO-2015029964, translation generated Apr. 2019, 98 pages. (Year: 2019).*
International Search Report dated Jun. 21, 2016 in PCT/JP2016/058877 filed Mar. 18, 2016.
Adachi, Chihaya, "Yuki Hando-tai no Debaisu Bussei (Device Physics of Oganic Semiconductors)," Kodansha, Mar. 2012, 5 pages (with English Translation).
Lee, Sae Youn et al., "High-efficiency organic light-emitting diodes utilizing thermally activated delayed fluorescence from triazine-based donor-acceptor hybrid molecules," Applied Physics Letters, vol. 101, 2012, 5 pages.
Extended European Search Report dated Oct. 8, 2018 in Patent Application No. 16772422.8, 10 pages.

* cited by examiner

ORGANIC ELECTROLUMINESCENT ELEMENT, ELECTRONIC DEVICE AND COMPOUND

TECHNICAL FIELD

The present invention relates to an organic electroluminescence device, an electronic device and a compound.

BACKGROUND ART

When a voltage is applied to an organic electroluminescence device (hereinafter, occasionally referred to as an "organic EL device"), holes and electrons are injected into an emitting layer respectively from an anode and a cathode. The injected holes and electrons are recombined in the emitting layer to form excitons. Here, according to the electron spin statistics theory, singlet excitons are generated at a ratio of 25% and triplet excitons are generated at a ratio of 75%.

A fluorescent organic EL device, which uses emission caused by singlet excitons, is applied to full-color displays for cellular phones and televisions. Studies for further enhancing the performance of fluorescent organic EL devices have been made. For instance, in order to further enhance the emission efficiency, an organic EL device that uses the singlet excitons and triplet excitons has been studied.

An organic EL device using delayed fluorescence has been proposed and studied. For instance, a thermally activated delayed fluorescence (TADF) mechanism has been studied. The TADF mechanism uses such a phenomenon that inverse intersystem crossing from triplet excitons to singlet excitons thermally occurs when a material having a small energy difference ($\Delta ST$) between singlet energy level and triplet energy level is used. As for thermally activated delayed fluorescence, refer to, for instance, "ADACHI, Chihaya, ed. (Mar. 22, 2012), *Yuki Hando-tai no Debaisu Bussei* (*Device Physics of Organic Semiconductors*), Kodansha, pp. 261-262."

For instance, Patent Literatures 1, 2 and 3 disclose organic EL devices using the TADF mechanism. Patent Literatures 1 to 3 relate to organic EL devices, in which delayed-fluorescent material is mainly emitted in the emitting layer.

CITATION LIST

Patent Literature(s)

Patent Literature 1: International Publication No. WO2014/092083
Patent Literature 2: International Publication No. WO2014/106524
Patent Literature 3: International Publication No. WO2015/022835

SUMMARY OF THE INVENTION

Problems to be Solved by the Invention

An object of the invention is to provide an organic electroluminescence device capable of improving a luminous efficiency and an electronic device including the organic electroluminescence device. Another object of the invention is to provide a compound capable of improving the luminous efficiency of an organic electroluminescence device.

Means for Solving the Problems

According to an aspect of the invention, an organic electroluminescence device including an anode, an organic layer and a cathode is provided, the emitting layer containing a delayed-fluorescent first compound represented by a formula (1) and a fluorescent second compound.

[Formula 1]

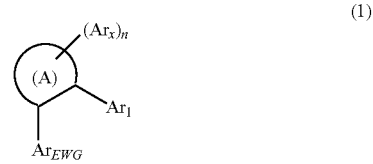

(1)

In the formula (1), $Ar_1$ is a group selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, a carboxy group, and groups represented by formulae (1a) to (1j) below, $Ar_{EWG}$ is a substituted or unsubstituted heteroaryl group having 5 to 30 ring atoms which has one or more nitrogen atom in the ring, or an aryl group having 6 to 30 ring carbon atoms and substituted by one or more cyano group;

$Ar_X$ is each independently a hydrogen atom or a substituent, and Arx as a substituent is a group selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, a carboxy group, and the groups represented by the formulae (1a) to (1j);

n represents an integer ranging from 0 to 5;
when n is 2 or more, a plurality of $Ar_X$s are mutually the same or different;
the ring (A) is a five-membered ring, a six-membered ring, or a seven-membered ring;
at least one of $Ar_1$ and $Ar_X$ is selected from the group consisting of groups represented by the formulae (1a) to (1j) below.

[Formula 2]

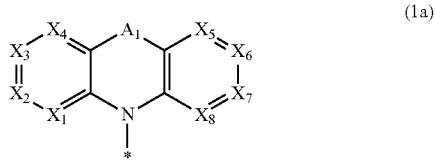

(1a)

-continued

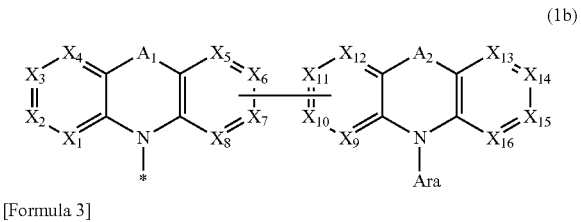

[Formula 3]

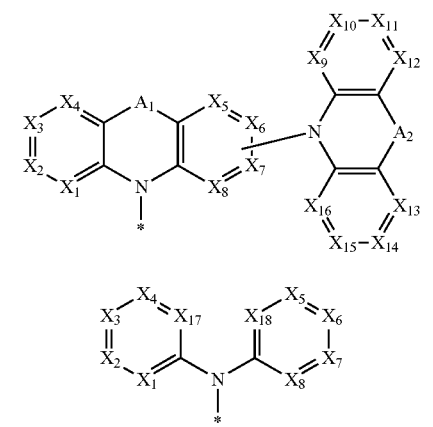

[Formula 4]

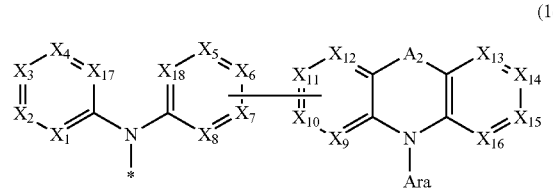

[Formula 5]

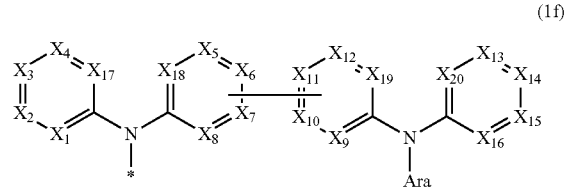

[Formula 6]

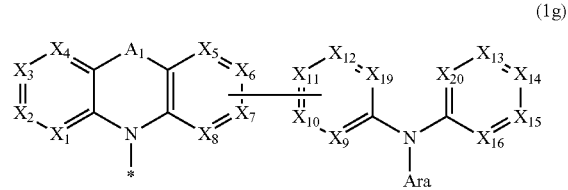

[Formula 7]

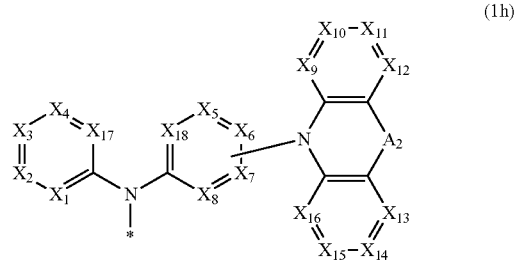

-continued

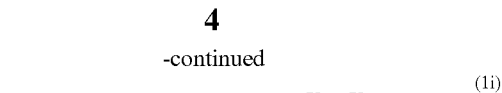

[Formula 8]

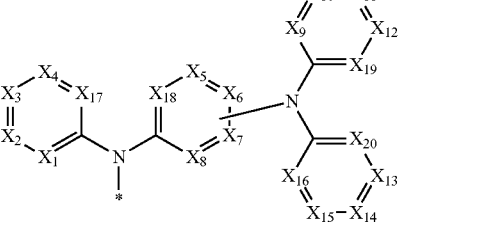

In the formulae (1a) to (1j): $X_1$ to $X_{20}$ are each independently N or C—Rx, with a proviso that: in the formula (1b), one of $X_5$ to $X_8$ is a carbon atom bonded to one of $X_9$ to $X_{12}$, and one of $X_9$ to $X_{12}$ is a carbon atom bonded to one of $X_5$ to $X_8$; in the formula (1c), one of $X_5$ to $X_8$ is a carbon atom bonded to the nitrogen atom in the ring comprising $A_2$; in the formula (1e), one of $X_5$ to $X_8$ and $X_{18}$ is a carbon atom bonded to one of $X_9$ to $X_{12}$, and one of $X_9$ to $X_{12}$ is a carbon atom bonded to one of $X_5$ to $X_8$ and $X_{18}$; in the formula (1f), one of $X_5$ to $X_8$ and $X_{18}$ is a carbon atom bonded to one of $X_9$ to $X_{12}$ and $X_{19}$ and one of $X_9$ to $X_{12}$ and $X_{19}$ is a carbon atom bonded to one of $X_5$ to $X_8$ and $X_{18}$; in the formula (1g), one of $X_5$ to $X_8$ is a carbon atom bonded to one of $X_9$ to $X_{12}$ and $X_{19}$, and one of $X_9$ to $X_{12}$ and $X_{19}$ is a carbon atom bonded to one of $X_5$ to $X_8$; in the formula (1h), one of $X_5$ to $X_8$ and $X_{18}$ is a carbon atom bonded the a nitrogen atom in the ring comprising $A_2$; in the formula (1i), one of $X_5$ to $X_8$ and $X_{18}$ is a carbon atom bonded to a nitrogen atom connecting the ring comprising $X_9$ to $X_{12}$ and $X_{19}$ and the ring comprising $X_{13}$ to $X_{16}$ and $X_{20}$; and in the formula (1j), one of $X_5$ to $X_8$ is a carbon atom bonded the a nitrogen atom connecting the ring comprising $X_9$ to $X_{12}$ and $X_{19}$ and the ring comprising $X_{13}$ to $X_{16}$ and $X_{20}$;

$R_X$ is each independently a hydrogen atom or a substituent, and Rx as a substituent is a group selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, and a carboxy group; and a plurality of Rxs as substituents are mutually the same or different, the plurality of Rxs as the substituents being directly bonded to each other to form a ring, being bonded via a hetero atom to form a ring, or not forming a ring;

$A_1$ and $A_2$ are each independently a single bond, O, S, $C(R_1)(R_2)$, $Si(R_3)(R_4)$, $C(=O)$, $S(=O)$, $SO_2$ or $N(R_5)$;

$R_1$ to $R_5$ are each independently a hydrogen atom or a substituent, and $R_1$ to $R_5$ as substituents are groups selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, and a carboxy group; and Ara is a group selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, and a substituted silyl group.

An electronic device according to another aspect of the invention includes the organic electroluminescence device according to the above aspect.

A compound of according to still another aspect of the invention is represented by a formula (10) or a formula (11) below.

[Formula 9]

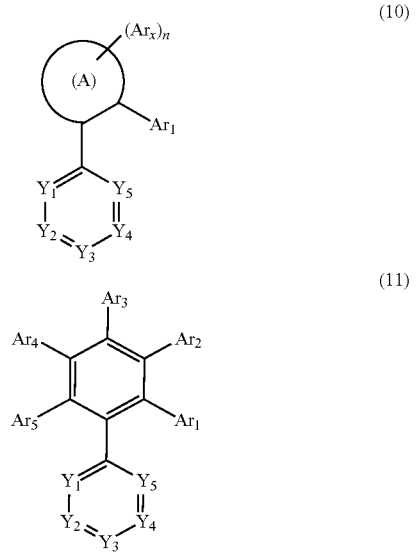

In the formulae (10) and (11):

$Y_1$ to $Y_5$ are each independently N, C—CN or C—Ry, at least one of $Y_1$ to $Y_5$ being N or C—CN;

Ry is each independently a hydrogen atom or a substituent, and Ry as a substituent is a group selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, and a carboxy;

A plurality of $R_y$s are mutually the same or different;

$Ar_1$ is a group selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, a carboxy group, and groups represented by formulae (1a) to (1c);

Arx and $Ar_2$ to $Ar_5$ each independently represent a hydrogen atom or a substituted, and Arx and $Ar_2$ to $Ar_5$ as substituents are groups selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, a carboxy group, and the groups represented by formulae (1a) to (1c) below;

n represents an integer ranging from 0 to 5;

when n is 2 or more, a plurality of $Ar_x$s are mutually the same or different;

the ring (A) is a five-membered ring, a six-membered ring, or a seven-membered ring;

In the above formula (10), at least one of $Ar_1$ and $Ar_X$ is selected from the group consisting of groups represented by the formulae (1a) to (1c) below; and In the above formula (11), at least one of $Ar_1$ to $Ar_5$ is selected from the group consisting of groups represented by the formulae (1a) to (1c).]

[Formula 10]

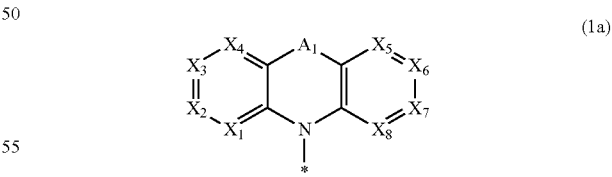

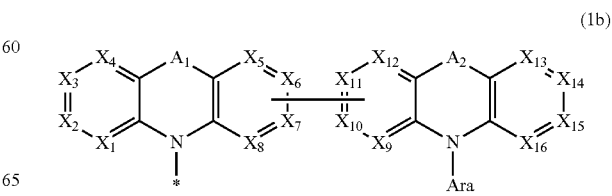

[Formula 11]

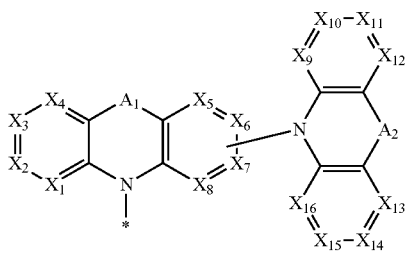

(1c)

In the formulae (1a) to (1c): $X_1$ to $X_{16}$ are each independently N or C-Rx; with a proviso that:

In the formula (1b), one of $X_5$ to $X_8$ is a carbon atom bonded to one of $X_9$ to $X_{12}$, and one of $X_9$ to $X_{12}$ is a carbon atom bonded to one of $X_5$ to $X_8$;

In the formula (1c), one of $X_5$ to $X_8$ is a carbon atom bonded to the nitrogen atom in the ring comprising $A_2$;

$R_X$ is each independently a hydrogen atom or a substituent, Rx as a substituent is a group selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or substituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, and a carboxy group;

A plurality of Rxs as substituents are mutually the same or different;

The plurality of Rxs as the substituents are directly bonded to each other to form a ring, are bonded via a hetero atom to form a ring or do not form a ring;

$A_1$ and $A_2$ are each independently a single bond, O, S, $C(R_1)(R_2)$, $Si(R_3)(R_4)$, $C(=O)$, $S(=O)$, $SO_2$ or $N(R_5)$;

$R_1$ to $R_5$ are each independently a hydrogen atom or a substituent, $R_1$ to $R_5$ as substituents are groups selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, and a carboxy group; and Ara is a group selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, and a substituted silyl group.

According to the above aspects of the invention, an organic electroluminescence device capable of improving a luminous efficiency and an electronic device including the organic electroluminescence device can be provided.

According to the still another aspects of the invention, a compound adapted to improve the luminous efficiency of an organic electroluminescence device can be provided.

DESCRIPTION OF EMBODIMENT(S)

First Exemplary Embodiment

Compound

Figure 1:
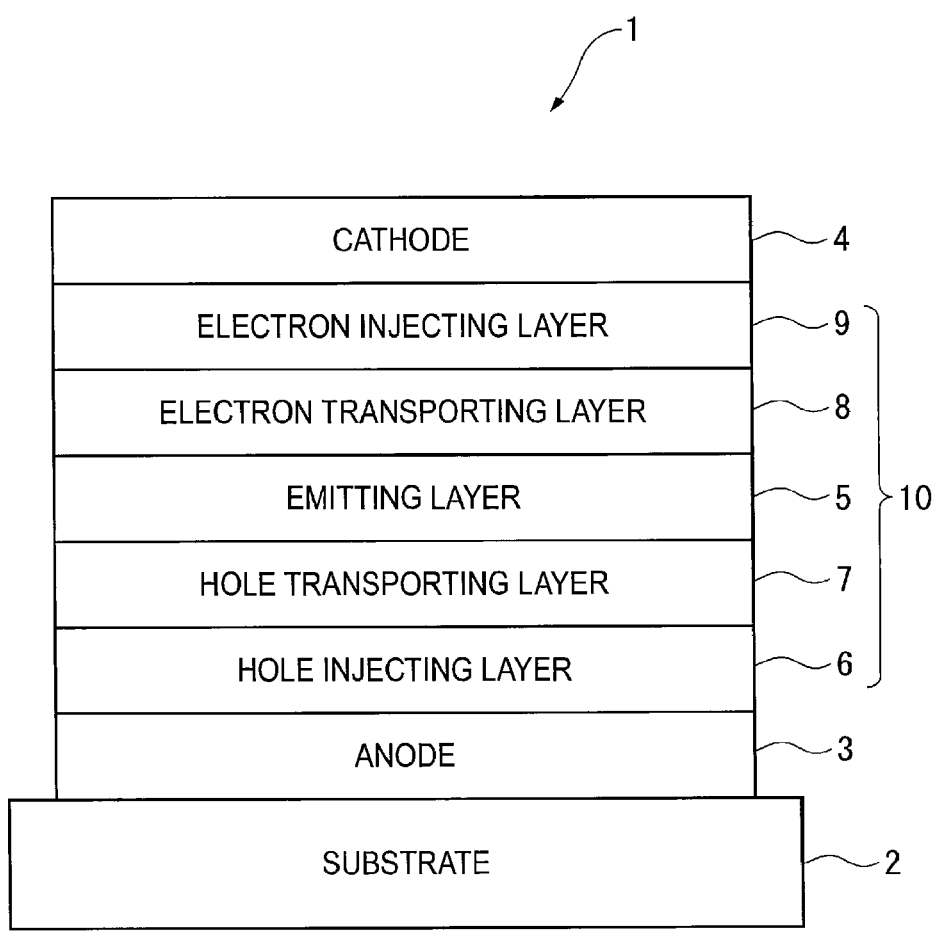
FIG. 1 schematically shows an exemplary arrangement of an organic electroluminescence device according to a first exemplary embodiment of the invention.

A compound according to a first exemplary embodiment of the invention will be described below.

The compound of the first exemplary embodiment is represented by a formula (1). The compound in the first exemplary embodiment is a delayed fluorescent compound.

[Formula 12]

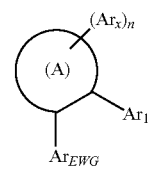

(1)

In the formula (1), $Ar_1$ is a group selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, a carboxy group, and groups represented by formulae (1a) to (1j).

In the above formula (1), $Ar_{EWG}$ is a substituted or unsubstituted heteroaryl group having 5 to 30 ring atoms which has one or more nitrogen atom in the ring, or an aryl group having 6 to 30 ring carbon atoms and substituted by one or more cyano group.

In the formula (1), $Ar_X$ is each independently a hydrogen atom or a substituent, Arx as a substituent is a group selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, a carboxy group, and the groups represented by the formulae (1a) to (1j).

In the above formula (1), n represents an integer ranging from 0 to 5. When n is 2 or more, a plurality of $Ar_X$s may be mutually the same or different.

In the formula (1), the ring (A) is a five-membered ring, a six-membered ring, or a seven-membered ring. The ring (A) may be an aromatic hydrocarbon ring or a heterocyclic ring.

In the above formula (1), at least one of $Ar_1$ and $Ar_X$ is a group selected from the group consisting of groups represented by the formulae (1a) to (1j).

[Formula 13]

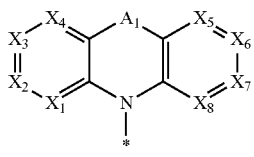
(1a)

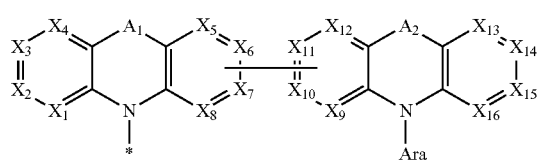
(1b)

[Formula 14]

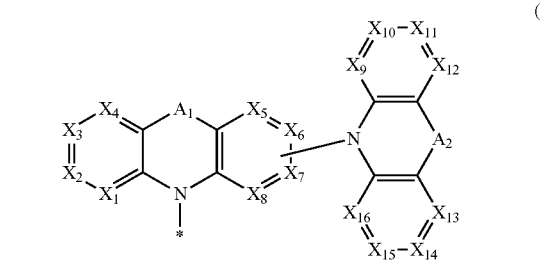
(1c)

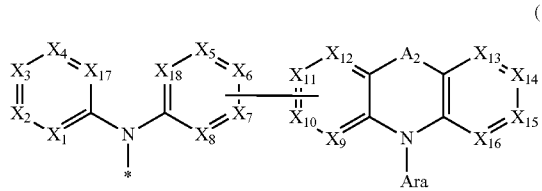
(1d)

[Formula 15]

(1e)

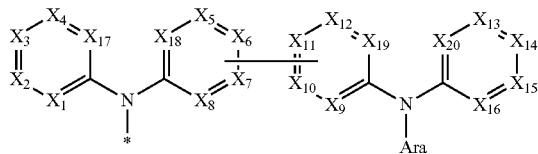

[Formula 16]

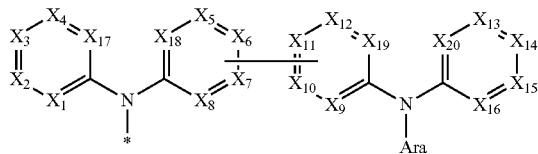
(1f)

[Formula 17]

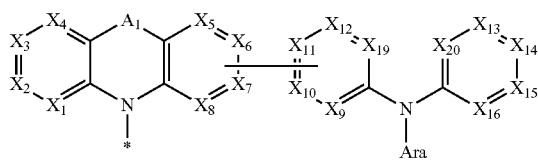
(1g)

[Formula 18]

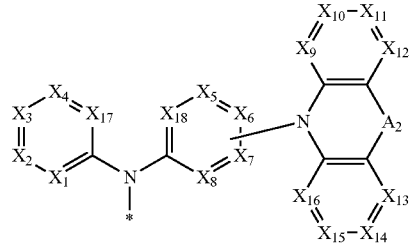
(1h)

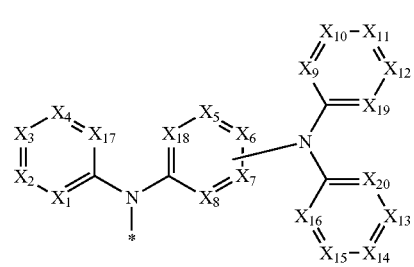
(1i)

[Formula 19]

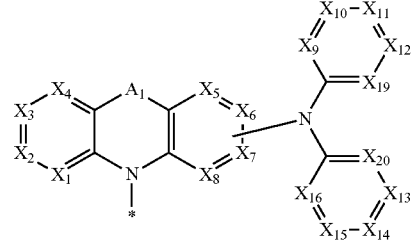
(1j)

In the above formulae (1a) to (1j), $X_1$ to $X_{20}$ are each independently a nitrogen atom (N), or a carbon atom bonded to Rx (C—$R_X$);

In the above formula (1b), one of $X_5$ to $X_8$ is a carbon atom bonded to one of $X_9$ to $X_{12}$. One of $X_9$ to $X_{12}$ is a carbon atom bonded to one of $X_5$ to $X_8$.

In the formula (1c), one of $X_5$ to $X_8$ is a carbon atom bonded to the nitrogen atom in the ring including $A_2$.

In the above formula (1e), one of $X_5$ to $X_8$ and $X_{18}$ is a carbon atom bonded to one of $X_9$ to $X_{12}$. One of $X_9$ to $X_{12}$ is a carbon atom bonded to one of $X_5$ to $X_8$ and $X_{18}$.

In the above formula (1f), one of $X_5$ to $X_8$ and $X_{18}$ is a carbon atom bonded to one of $X_9$ to $X_{12}$ and $X_{19}$. One of $X_9$ to $X_{12}$ and $X_{19}$ is a carbon atom bonded to one of $X_5$ to $X_8$ and $X_{18}$.

In the above formula (1g), one of $X_5$ to $X_8$ is a carbon atom bonded to one of $X_9$ to $X_{12}$ and $X_{19}$. One of $X_9$ to $X_{12}$ and $X_{19}$ is a carbon atom bonded to one of $X_5$ to $X_8$.

In the formula (1h), one of $X_5$ to $X_8$ and $X_{18}$ is a carbon atom bonded to the nitrogen atom in the ring including $A_2$.

In the formula (1i), one of $X_5$ to $X_8$ and $X_{18}$ is a carbon atom bonded to the nitrogen atom connecting the ring including $X_9$ to $X_{12}$ and $X_{19}$ and the ring including $X_{13}$ to $X_{16}$ and $X_{20}$.

In the formula (1j), one of $X_5$ to $X_8$ is a carbon atom bonded to the nitrogen atom connecting the ring including $X_9$ to $X_{12}$ and $X_{19}$ and the ring including $X_{13}$ to $X_{16}$ and $X_{20}$.

$R_X$ is each independently a hydrogen atom or a substituent, Rx as a substituent is a group selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, and a carboxy group.

A plurality of Rxs as substituents are mutually the same or different;

The plurality of Rxs as the substituents are directly bonded to form a ring, form a ring via a hetero atom or form no ring.

In the formula (1a), when $X_1$ to $X_8$ are carbon atoms bonded to Rx (C-Rx), the plurality of Rxs as substituents preferably do not form a ring.

* represents a bonding site to the ring (A).

In the above formulae (1a) to (1j), $A_1$ and $A_2$ are each independently a single bond, an oxygen atom (O), a sulfur atom (S), $C(R_1)(R_2)$, $Si(R_3)(R_4)$, $C(=O)$, $S(=O)$, $SO_2$ or $N(R_5)$. $R_1$ to $R_5$ are each independently a hydrogen atom or a substituent, and $R_1$ to $R_5$ as substituents are groups selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, and a carboxy group.

In the formulae (1a) to (1j), Ara is a group selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, and a substituted silyl group. Ara is preferably a substituted or unsubstituted aryl group having 6 to 30 ring carbon atoms or a substituted or unsubstituted heteroaryl group having 5 to 30 ring atoms.

When $X_1$ to $X_8$ are C—Rx, the formula (1a) is represented by a formula (1ax). In the formula (1ax), $Rx_1$ to $Rx_8$ are the same as Rx, and $Rx_1$ to $Rx_8$ are mutually the same or different. In the formula (1ax), $Rx_1$ to $Rx_8$ as the substituent preferably do not form a ring.

[Formula 20]

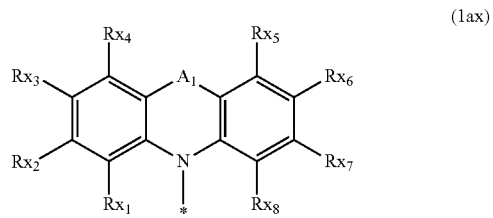

(1ax)

The above formula (1a) is represented as a formula (1aa) when $A_1$ is a single bond, represented as a formula (1ab) when $A_1$ is O, represented as a formula (1ac) when $A_1$ is S, represented as a formula (1ad) when $A_1$ is $C(R_1)(R_2)$, represented as a formula (1ae) when $A_1$ is $Si(R_3)(R_4)$, represented as a formula (1af) when $A_1$ is $C(=O)$, represented as a formula (1ag) when $A_1$ is $S(=O)$, represented as a formula (1ah) when $A_1$ is $SO_2$, and represented as a formula (1ai) when $A_1$ $N(R_5)$. In the formulae (1aa) to (1ai), $X_1$ to $X_8$ and $R_1$ to $R_5$ are the same as those described above. In the above formulae (1b), (1c), (1e) and (1g) to (1j), the rings are connected at $A_1$ and $A_2$ in the same manner as in the formulae (1aa) to (1ai). In the formula (1aa), when $X_1$ to $X_8$ are carbon atoms bonded to Rx (C-Rx), the plurality of Rxs as substituents preferably do not form a ring.

[Formula 21]

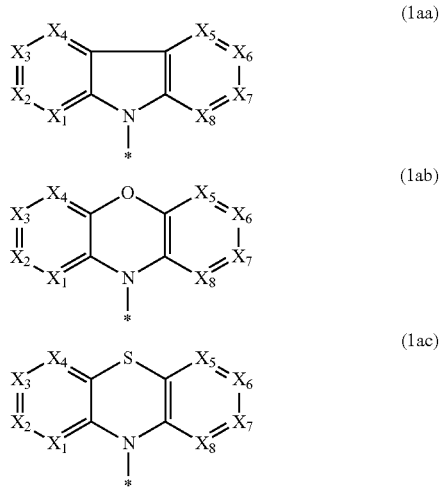

[Formula 22]

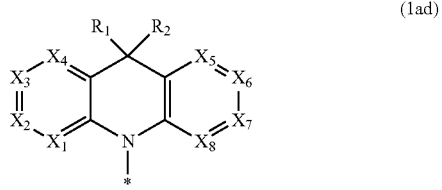

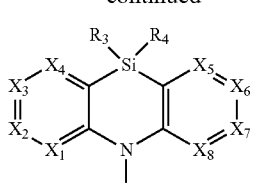
(1ae)

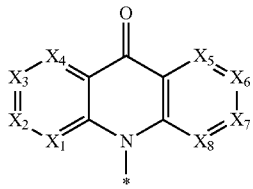
(1af)

[Formula 23]

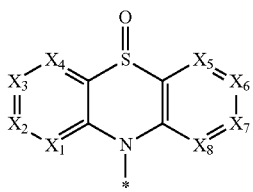
(1ag)

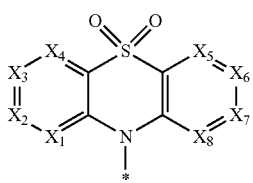
(1ah)

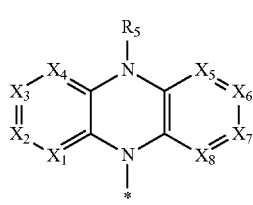
(1ai)

The compound of the first exemplary embodiment is preferably represented by a formula (10).

[Formula 24]

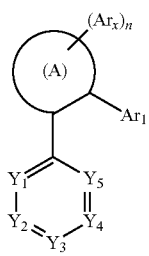
(10)

In the above formula (10), $Y_1$ to $Y_5$ are each independently N, C—CN or C—Ry, at least one of $Y_1$ to $Y_5$ being N C—CN.

Ry is each independently a hydrogen atom or a substituent, and Ry as substituent is a group selected from the group consisting of a substituted or unsubstituted aryl group having 6 to 0 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, and a carboxy group. Ry is preferably a substituted or unsubstituted aryl group having 6 to 30 ring carbon atoms or a substituted or unsubstituted heteroaryl group having 5 to 30 ring atoms. A plurality of Rys are mutually the same or different;

In the formula (10), $Ar_1$ is a group selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, a carboxy group, and the groups represented by the above formulae (1a) to (1c).

In the formula (10), $Ar_X$ is each independently a hydrogen atom or a substituent, and Arx as a substituent is a group selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, a carboxy group, and the groups represented by the above formulae (1a) to (1c).

In the formulae (10), n is an integer ranging from 0 to 5. When n is an integer of 2 or more, a plurality of Arxs are mutually the same or different.

In the formula (10), the ring (A) is a five-membered ring, a six-membered ring, or a seven-membered ring. The ring (A) may be an aromatic hydrocarbon ring or a heterocyclic ring.

In the above formula (10), at least one of $Ar_1$ and $Ar_X$ is a group selected from the group consisting of the groups represented by the above formulae (1a) to (1c).

In the first exemplary embodiment, the ring (A) is preferably a six-membered ring, more preferably an aromatic six-membered ring.

The compound of the first exemplary embodiment is also preferably represented by a formula (10x). In the formula (10x), $Ar_1$, $Ar_{EWG}$, and $Ar_2$ to $Ar_5$ are the same as $Ar_1$, $Ar_{EWG}$, and $Ar_2$ to $Ar_5$ described above.

[Formula 25]

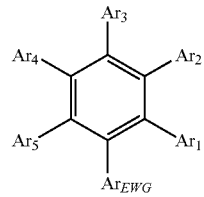
(10x)

The compound of the first exemplary embodiment is also preferably represented by a formula (11).

[Formula 26]

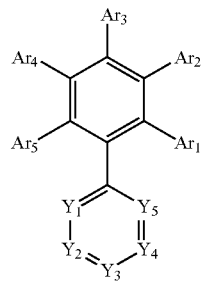

(11)

In the above formula (11), $Y_1$ to $Y_5$ are each independently a nitrogen atom (N), a carbon atom bonded to a cyano group (C—CN) or a carbon atom bonded to Ry (C-Ry), at least one of $Y_1$ to $Y_5$ being N or C—CN. A plurality of Rys are mutually the same or different.

In the above formula (11), Ry and $Ar_1$ are the same as described above.

In the formula (11), $Ar_2$ to $Ar_5$ are each independently a hydrogen atom or a substituent, and $Ar_2$ to $Ar_5$ as substituents are groups selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, a carboxy group, and the groups represented by the above formulae (1a) to (1c).

In the above formula (11), at least one of $Ar_1$ and $Ar_5$ is a group selected from the group consisting of the groups represented by the above formulae (1a) to (1c).

The compound of the first exemplary embodiment is also preferably represented by a formula (11a), a formula (11b) or a formula (11c).

[Formula 27]

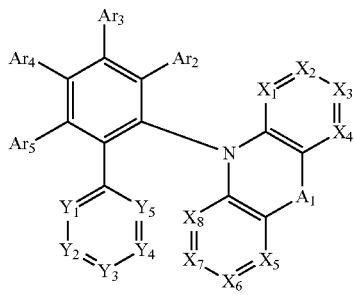

(11a)

[Formula 28]

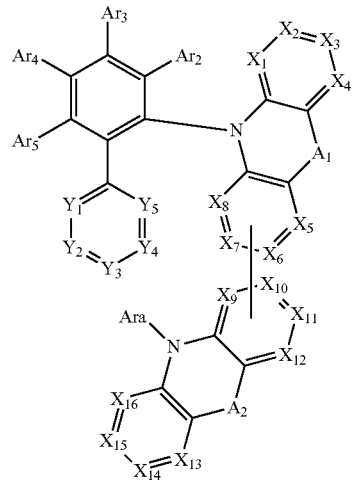

(11b)

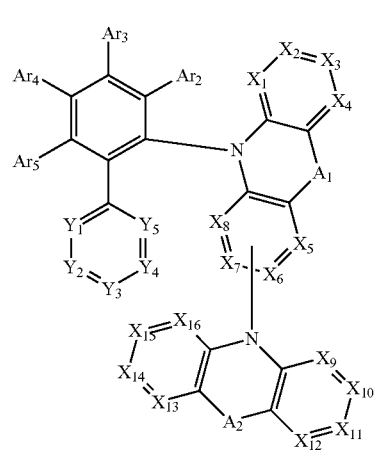

(11c)

In the above formulae (11a), (11b) and (11c), $Y_1$ to $Y_5$, Ry, $Ar_2$ to $Ar_5$, $X_1$ to $X_{16}$, Rx, $A_1$, $A_2$, $R_1$ to $R_5$ and Ara are the same as the above-described $Y_1$ to $Y_5$, Ry, $Ar_2$ to $Ar_5$, $X_1$ to $X_{16}$, Rx, $A_1$, $A_2$, $R_1$ to $R_5$, and Ara.

The compound of the first exemplary embodiment is also preferably represented by a formula (11aa), a formula (11bb) or a formula (11cc).

[Formula 29]

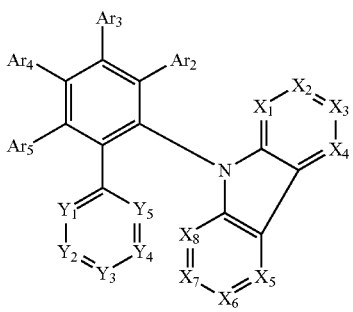

(11aa)

-continued

[Formula 30]

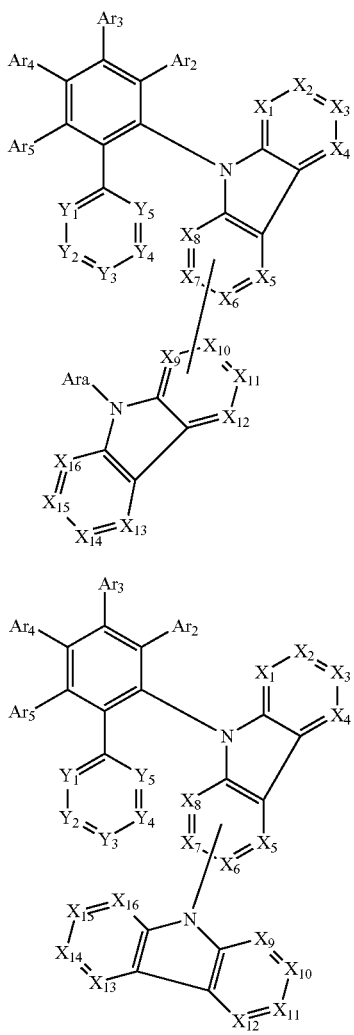

(11bb)

(11cc)

In the above formulae (11aa), (11bb) and (11cc), $Y_1$ to $Y_5$, Ry, $Ar_2$ to $Ar_5$, $X_1$ to $X_{16}$, Rx, and Ara are the same as the above-described $Y_1$ to $Y_5$, Ry, $Ar_2$ to $Ar_5$, $X_1$ to $X_{16}$, Rx, and Ara.

In the first exemplary embodiment, $Ar_1$ and $Ar_2$ are also preferably selected from the group consisting of the groups represented by the above formulae (1a) to (1j). In this case, it is preferable that $Ar_3$ to $Ar_5$ are each independently a hydrogen atom or a substituent, and $Ar_3$ to $Ar_5$ as substituents are groups selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 rings carbon atoms, a substituted or unsubstituted aralkyl group having 7 to 30 carbon atoms, a substituted phosphoryl group, a substituted silyl group, a cyano group, a nitro group, and a carboxy group.

In the first exemplary embodiment, $Ar_2$ and $Ar_3$ are also preferably selected from the group consisting of the groups represented by the above formulae (1a) to (1j). In this case, it is preferable that $Ar_1$ and $Ar_4$ to $Ar_5$ are each independently a hydrogen atom or a substituent, and $Ar_1$ and $Ar_4$ to $Ar_5$ as substituents are groups selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, and a carboxy group.

In the first exemplary embodiment, $Ar_1$ and $Ar_2$ are also preferably selected from the group consisting of the groups represented by the above formulae (1a) to (1c).

In the first exemplary embodiment, it is preferable that, when $Ar_1$ and $Ar_2$ are each independently at least one group selected from the group consisting of the groups represented by the above formulae (1a) to (1j) or at least one group selected from the group consisting of the groups represented by the above formulae (1a) to (1c), $Ar_3$ and $Ar_5$ are each independently a hydrogen atom or a substituent, and $Ar_3$ and $Ar_5$ as substituents are groups selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, and a carboxy group.

In the first exemplary embodiment, when $Ar_1$ and $Ar_2$ are each at least one group selected from the group consisting of the groups represented by the above formulae (1a) to (1j) or each at least one group selected from the group consisting of the groups represented by the above formulae (1a) to (1c), $Ar_1$ and $Ar_2$ are also preferably mutually different.

In the first exemplary embodiment, when $Ar_1$ and $Ar_2$ are each at least one group selected from the group consisting of the groups represented by the above formulae (1a) to (1j) or each at least one group selected from the group consisting of the groups represented by the above formulae (1a) to (1c), at least one of $Ar_1$ and $Ar_2$ is also preferably the group represented by the above formula (1b) or (1c).

In the first exemplary embodiment, $Ar_2$ and $Ar_3$ are preferably selected from the group consisting of the groups represented by the above formulae (1a) to (1c).

In the first exemplary embodiment, it is preferable that, when $Ar_2$ and $Ar_3$ are each independently at least one group selected from the group consisting of the groups represented by the above formulae (1a) to (1j) or at least one group selected from the group consisting of the groups represented by the above formulae (1a) to (1c), $Ar_1$ is a group selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, and a carboxy group, and $Ar_4$ and $Ar_5$ are each independently a hydrogen atom or a substituent, and $Ar_4$ and $Ar_5$ as substituents are groups selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, and a carboxy group.

When a molecule of the compound according to the first exemplary embodiment includes one or two groups represented by the above formulae (1a) to (1j), it is preferable that the compound according to the first exemplary embodiment includes one substituted or unsubstituted heteroaryl group having 5 to 30 ring atoms which has one or more nitrogen atom in the ring, or one aryl group having 6 to 30 ring carbon atoms and substituted by one or more cyano group.

In the first exemplary embodiment, it is preferable that $Ar_1$, $Ar_2$ and $Ar_3$ are selected from the group consisting of the groups represented by the above formulae (1a) to (1j), and more preferably selected from the group consisting of the groups represented by the above formulae (1a) to (1c), $Ar_1$, $Ar_2$ and $Ar_3$ being mutually the same or different.

In the first exemplary embodiment, it is preferable that, when $Ar_1$, $Ar_2$ and $Ar_3$ are each independently at least one group selected from the group consisting of the groups represented by the above formulae (1a) to (1j) or at least one group selected from the group consisting of the groups represented by the above formulae (1a) to (1c), $Ar_4$ and $Ar_5$ are each independently a hydrogen atom or a substituent, and $Ar_4$ and $Ar_5$ as substituents are groups selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, and a carboxy group.

In the first exemplary embodiment, at least one of $Y_1$, $Y_3$ and $Y_5$ is preferably a nitrogen atom (N).

In the first exemplary embodiment, it is preferable that $Y_1$ and $Y_3$ are N and $Y_2$, $Y_4$ and $Y_5$ are C-Ry.

For instance, when $Y_1$ and $Y_3$ are N and $Y_2$, $Y_4$ and $Y_5$ are C-Ry in the above formula (11aa), the compound is represented by a formula (111aa), where $Ry_1$ to $Ry_3$ are the same as the above-described Ry.

[Formula 31]

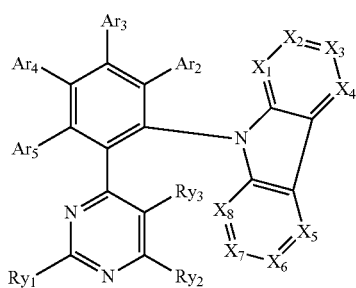

(111aa)

In the first exemplary embodiment, it is preferable that $Y_1$ and $Y_5$ are N and $Y_2$, $Y_3$ and $Y_4$ are C-Ry.

For instance, when $Y_1$ and $Y_5$ are N and $Y_2$, $Y_3$ and $Y_4$ are C-Ry in the above formula (11aa), the compound as represented by a formula (112aa), where $Ry_1$ to $Ry_3$ are the same as the above-described Ry.

[Formula 32]

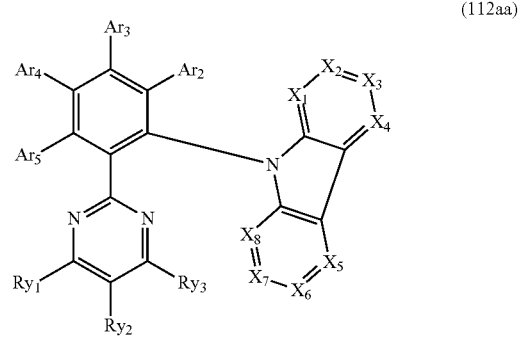

(112aa)

In the first exemplary embodiment, it is preferable that $Y_1$, $Y_3$ and $Y_5$ are N and $Y_2$ and $Y_4$ are C-Ry.

For instance, when $Y_1$, $Y_3$ and $Y_5$ are N and $Y_2$ and $Y_4$ are C-Ry in the above formula (11aa), the compound is represented by a formula (113aa), where $Ry_1$ to $Ry_3$ are the same as the above-described Ry.

[Formula 33]

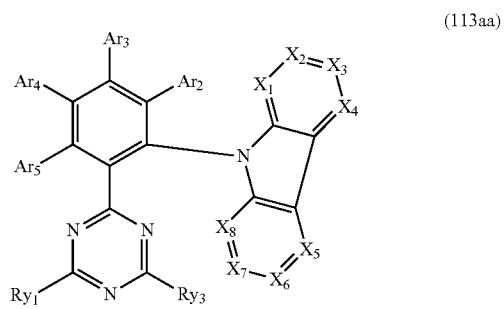

(113aa)

In the first exemplary embodiment, it is preferable that $X_1$ to $X_{20}$ are each independently a carbon atom bonded to Rx (C-Rx), and it is more preferable that Rx is H.

In the first exemplary embodiment, when $Ar_1$ is not a group represented by the formulae (1a) to (1j), $Ar_1$ in a form of a substituent is preferably a group selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms and a substituted silyl group, where $Ar_1$ is more preferably a substituted or unsubstituted aryl group having 6 to 30 ring carbon atoms or a substituted or unsubstituted heteroaryl group having 5 to 30 ring atoms, further preferably a substituted or unsubstituted aryl group having 6 to 30 ring carbon atoms, and further more preferably a substituted or unsubstituted aryl group having 6 to 10 ring carbon atoms.

In the first exemplary embodiment, when at least one of $Ar_2$, $Ar_3$, $Ar_4$ and $Ar_5$ is not a group represented by the formulae (1a) to (1j), $Ar_2$ to $Ar_5$ in a form of a substituent are preferably each independently a group selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms and a substituted silyl group, are more preferably selected from the group consisting of a substituted or unsubstituted aryl group having 6 to 30 ring carbon atoms, a substituted or unsubstituted alkyl group having 1 to 30 carbon atoms, a substituted or unsubstituted fluoroalkyl group having 1 to 30 carbon atoms and a substituted silyl group, are further preferably a substituted or unsubstituted aryl group having 6 to 30 ring carbon atoms, and are further more preferably a substituted or unsubstituted aryl group having 6 to 10 ring carbon atoms. In the first exemplary embodiment, when at least one of $Ar_2$, $Ar_3$, $Ar_4$ and $Ar_5$ is not a group represented by the above formulae (1a) to (1j), $Ar_2$ to $Ar_5$ are each also preferably a hydrogen atom.

Manufacturing Method of Compound of First Exemplary Embodiment

The compound according to the first exemplary embodiment can be manufactured, for instance, according to the method described in the later-described Examples. The compound according to the first exemplary embodiment can be manufactured according to the method described in the later-described Examples and using known substitution reactions and materials in accordance with a target compound.

Delayed Fluorescence Characteristics

Delayed fluorescence (thermally activated delayed fluorescence) is described in, for instance, "Device Physics of Organic Semiconductor" Chihaya Adachi, pages 261 to 268, published by Kodansha Company Ltd. It is described in this document that, when an energy gap $\Delta E_{13}$ between a singlet state and a triplet state can be decreased, an inverse energy transfer from the triplet state to the singlet state, which usually occurs at a low transition probability, occurs at a high probability to express Thermally Activated Delayed Fluorescence (TADF). Further, an occurrence mechanism of the delayed fluorescence is described in FIG. 10.38 of this document. The first compound of the exemplary embodiment is a compound exhibiting thermally activated delayed fluorescence occurring in this mechanism. Emission of the delayed fluorescence can be checked by measuring the transient PL (Photo Luminescence).

Behavior of the delayed fluorescence can be analyzed based on the decay curve obtained by the transient PL measurement. The transient PL measurement is a method of measuring decay behavior (transient characteristics) of the PL emission after irradiation by a pulse laser on a sample and stopping irradiation. The PL emission in the TADF material is classified into a luminescence component from singlet excitons generated in first PL excitation and a luminescence component from singlet excitons generated through triplet excitons. A lifetime of the singlet excitons generated in the first PL excitation is in a nanosecond order, and is very short. Accordingly, the emission from the singlet excitons rapidly decays after the irradiation by the pulse laser.

On the other hand, since delayed fluorescence provides an emission from singlet excitons generated through long-life triplet excitons, the delayed fluorescence gradually decays. Thus, there is a large difference in time between the emission from the singlet excitons generated in the first PL excitation and the emission from the singlet excitons through the triplet excitons. Accordingly, a luminous intensity from the delayed fluorescence can be calculated.

Figure 2:
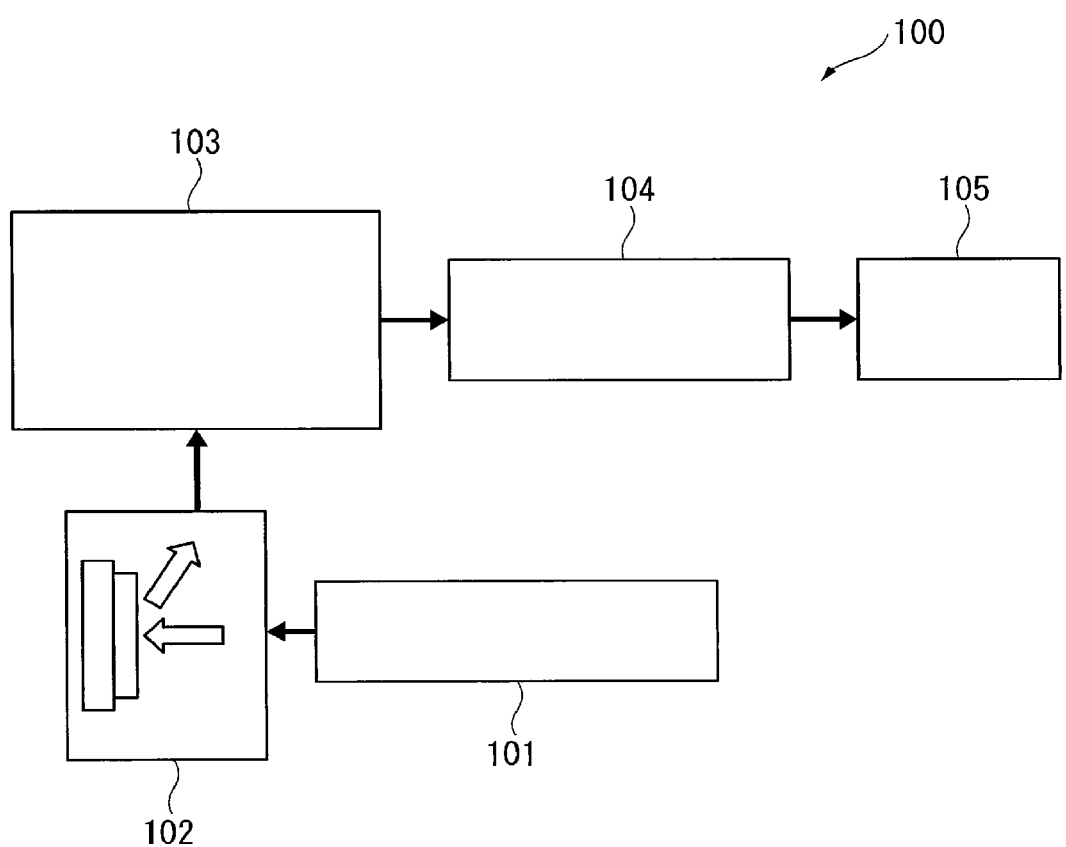
FIG. 2 schematically shows a device for measuring transient PL.

FIG. 2 schematically shows an exemplary device for measuring the transient PL.

A transient PL measuring device 100 in the exemplary embodiment includes: a pulse laser 101 capable of radiating a light having a predetermined wavelength; a sample chamber 102 configured to house a measurement sample; a spectrometer 103 configured to divide a light radiated from the measurement sample; a streak camera 104 configured to provide a two-dimensional image; and a personal computer 105 configured to import and analyze the two-dimensional image. A device for measuring the transient PL is not limited to the device described in the exemplary embodiment.

The sample to be housed in the sample chamber 102 is obtained by forming a thin film on a quartz substrate by doping a matrix material with a doping material at a concentration of 12 mass %.

The thin film sample housed in the sample chamber 102 is irradiated with a pulse laser from the pulse laser 101 to excite the doping material. Emission is extracted in a direction of 90 degrees with respect to a radiation direction of the excited light. The extracted emission is divided by the spectrometer 103 to form a two-dimensional image in the streak camera 104. As a result, the two-dimensional image is obtainable in which the ordinate axis represents a time, the abscissa axis represents a wavelength, and a bright spot represents a luminous intensity. When this two-dimensional image is taken out at a predetermined time axis, an emission spectrum in which the ordinate axis represents the luminous intensity and the abscissa axis represents the wavelength is obtainable. Moreover, when this two-dimensional image is taken out at the wavelength axis, a decay curve (transient PL) in which the ordinate axis represents a logarithm of the luminous intensity and the abscissa axis represents the time is obtainable.

For instance, a thin film sample A was manufactured as described above using a reference compound H1 as the matrix material and a reference compound D1 as the doping material and was measured in terms of the transient PL.

[Formula 34]

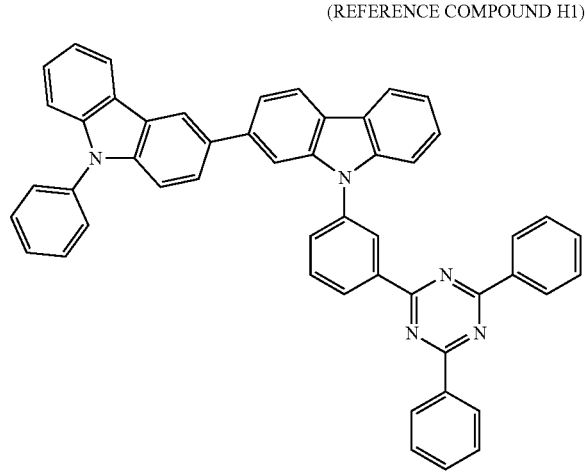

(REFERENCE COMPOUND H1)

(COMPOUND D1)

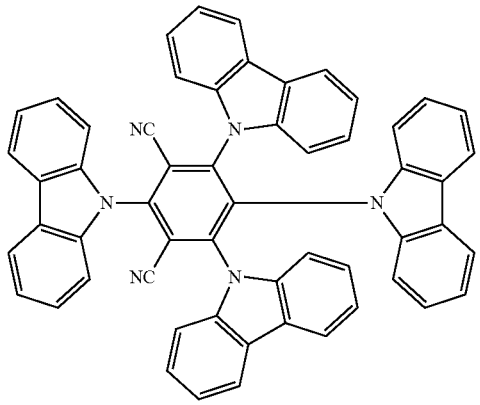

The decay curve was analyzed with respect to the above thin film sample A and a film sample B. The thin film sample B was manufactured in the same manner as described above using a reference compound H2 as the matrix material and the reference compound D1 as the doping material.

Figure 3:
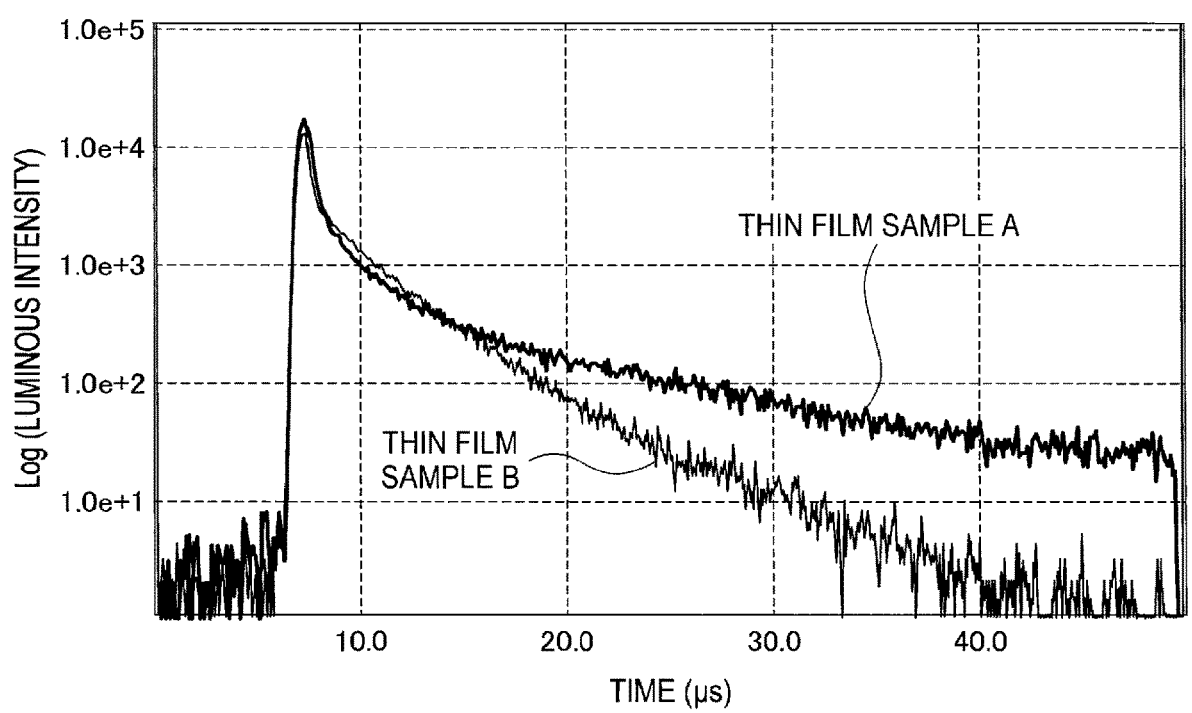
FIG. 3 shows an example of a decay curve of the transient PL.

FIG. 3 schematically shows decay curves obtained from transient PL obtained by measuring the respective thin film samples A and B.

[Formula 35]

(REFERENCE COMPOUND H2)

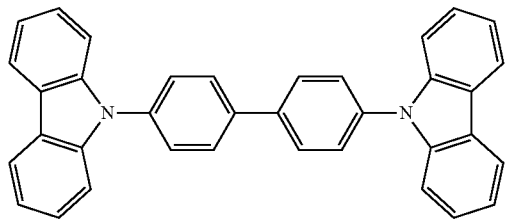

As described above, an emission decay curve in which the ordinate axis represents the luminous intensity and the abscissa axis represents the time can be obtained by the transient PL measurement. Based on the emission decay curve, a fluorescence intensity ratio between fluorescence emitted from a singlet state generated by photo-excitation and delayed fluorescence emitted from a singlet state generated by inverse energy transfer via a triplet state can be estimated. In a delayed fluorescent material, a ratio of the intensity of the slowly decaying delayed fluorescence to the intensity of the promptly decaying fluorescence is relatively large.

In the first exemplary embodiment, an emission amount of the delayed fluorescence can be obtained using the device shown in FIG. 2. In the compound according to the first exemplary embodiment, Prompt emission and Delay emission are observed. Prompt emission is observed immediately when the excited state is achieved by exciting the compound with a pulsed light (i.e., a light emitted from a pulse laser) having a wavelength which the compound absorbs. Delay emission is observed not immediately but after the excited state is achieved. In the first exemplary embodiment, the amount of Delay emission is preferably 5% or more relative to the amount of Prompt emission.

The amount of Prompt emission and the amount of Delay emission can be obtained in the same method as the method described in "Nature 492, 234-238, 2012." A device used for calculating the amount of Prompt emission and the amount of Delay emission is not limited to the device described in the above Literature.

For instance, a sample usable for measuring delayed fluorescence is manufactured by co-depositing the compound according to the first exemplary embodiment and a compound TH-2 below on a quartz substrate at a ratio of the compound of the first exemplary embodiment of 12 mass % to form a 100-nm-thick thin film.

[Formula 36]

TH-2

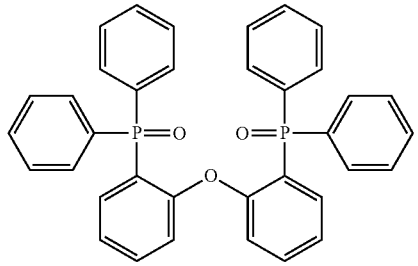

Since the compound according to the first exemplary embodiment has a structure represented by the above formula (1) etc., Delay emission component increases. The reason is speculated as follows. The compound according to the first exemplary embodiment includes an electron-donating group (the group represented by the above formulae (1a) to (1j)) and an electron-accepting group $Ar_{EWG}$ in the molecule, and the electron-accepting group and the substituent (which may be the electron-donating group) satisfy the relationship of the bonding positions represented by the above formula (1) etc. Accordingly, a torsion is caused in the molecular structure, and it is speculated that the HOMO (Highest Occupied Molecular Orbital) and the LUMO (Lowest Unoccupied Molecular Orbital) are separated. It is speculated that the separation of the HOMO and the LUMO reduces $\Delta ST$ and, as a result of the reduction in $\Delta ST$, inverse intersystem crossing becomes likely to occur to increase an emission amount of the delayed fluorescence.

In the compound according to the first exemplary embodiment, $Ar_1$ is preferably an electron-donating group (a group represented by the formulae (1a) to (1j)) and the bonding position with the electron-accepting group $Ar_{EWG}$ is as represented by the above formula (1) etc., and more preferably $Ar_1$ is a group represented by the above formula (1a) and further more preferably, Ar is a group represented by the above formula (1aa).

Further, in the compound according to the first exemplary embodiment, it is preferable that the electron-donating group (the group represented by the formulae (1a) to (1j)) is bonded to a first atom and a second atom adjacent the first atom of the ring (A) in the molecule, and it is more preferable that the electron-donating group is also bonded to a third atom adjacent to the first atom and different from the second atom. It is speculated that, since the electron-donating groups are bonded to adjacent atoms in the ring (A), the electron-donating performance due to interactions between the electron-donating groups improves, whereby the balance between the electron-accepting performance and electron-donating performance in the molecule becomes appropriate, thereby further increasing the emission amount of the delayed fluorescence. For instance, as shown in a formula (100x), it is preferable that the ring (A) has a first atom $C_1$, a second atom $C_2$ and a third atom $C_3$, the first to third atoms being adjacent with each other and $Ar_{EDG1}$ bonded to the first atom $C_1$ and $Ar_{EDG2}$ bonded to the second atom $C_2$ are electron-donating groups (the groups represented by the above formulae (1a) to (1j)). It is further more preferable that $Ar_{EDG3}$ is an electron-donating group.

[Formula 37]

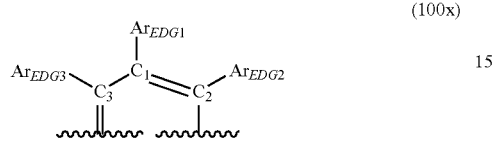

(100x)

With the use of the compound according to the first exemplary embodiment, the emission efficiency of the organic electroluminescence device can be enhanced.

Specific examples of the compound of the first exemplary embodiment are shown below. It should be noted that the compound in the exemplary embodiment is not limited thereto.

[Formula 38]

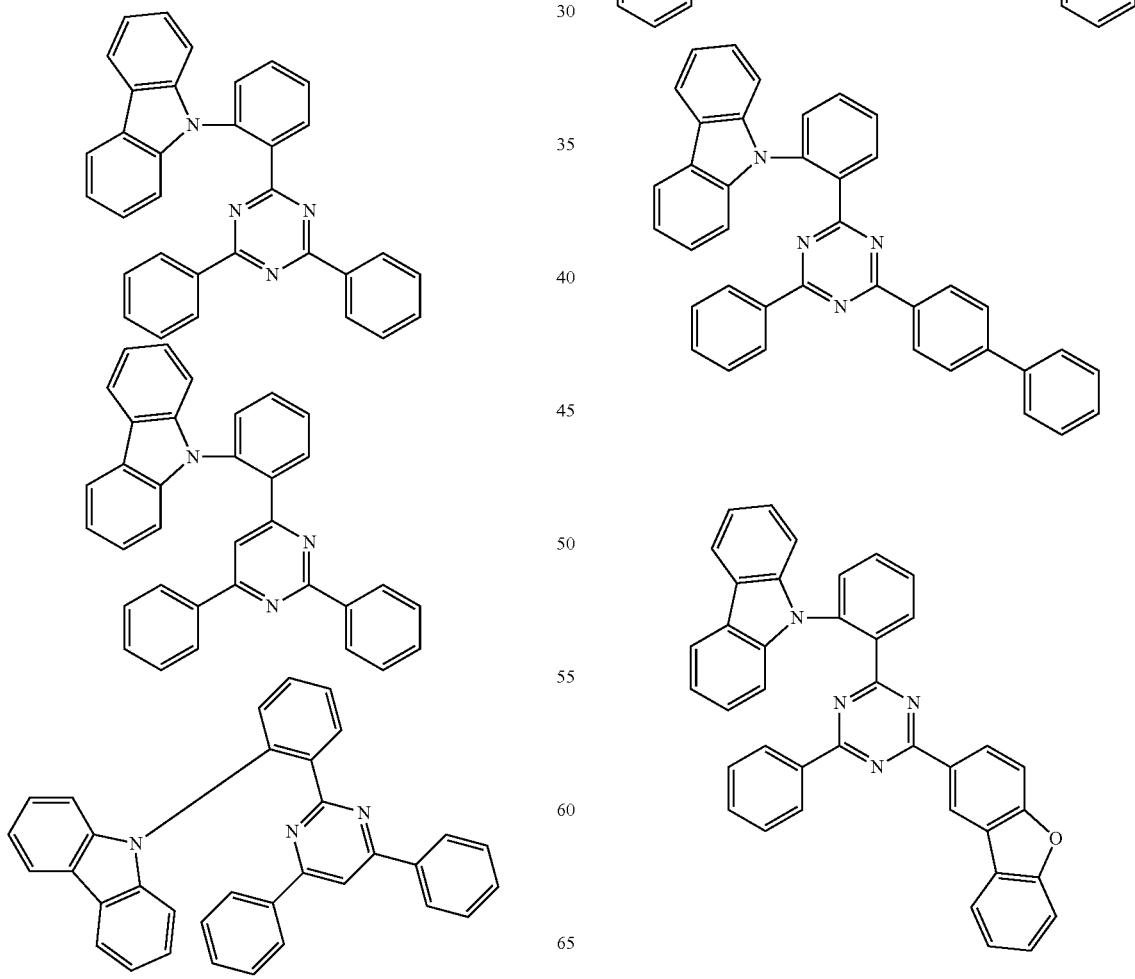

-continued

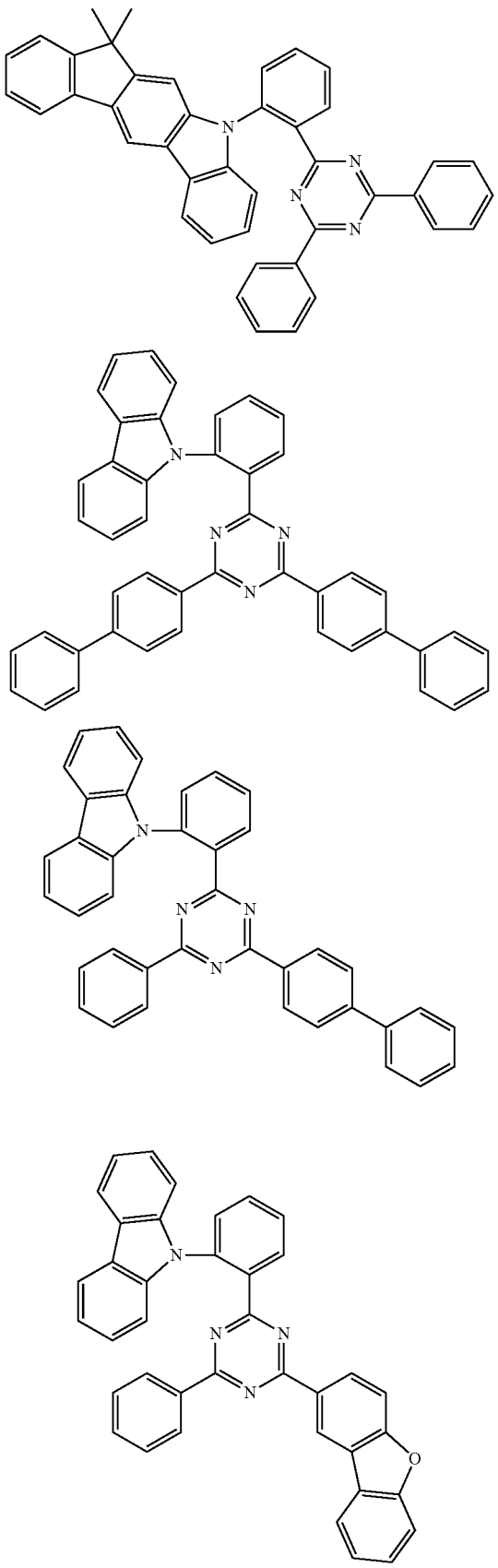

[Formula 39]
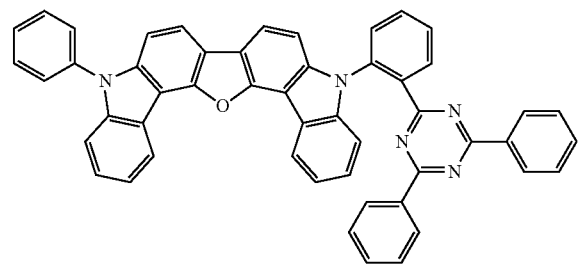
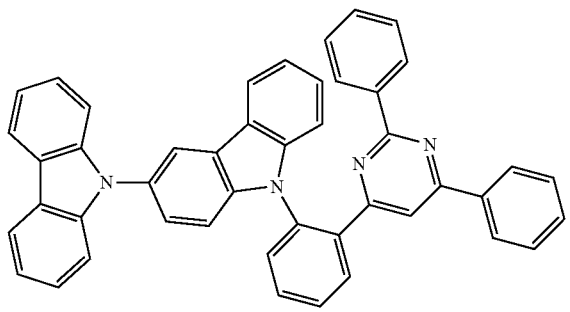
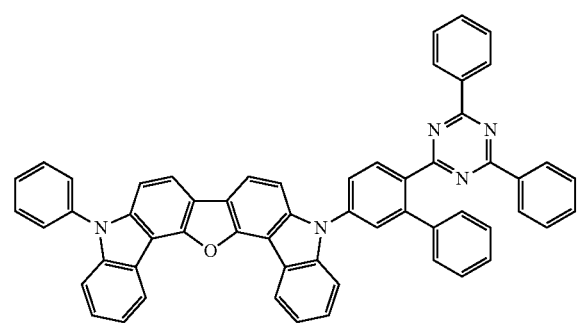
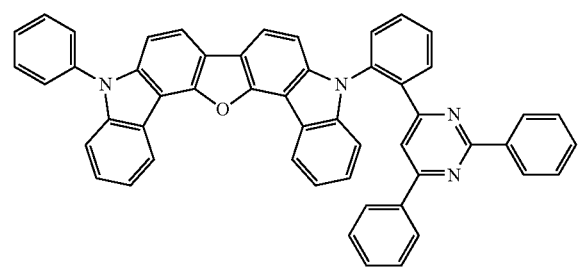
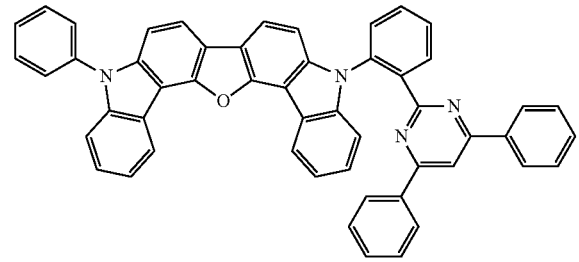
[Formula 40]
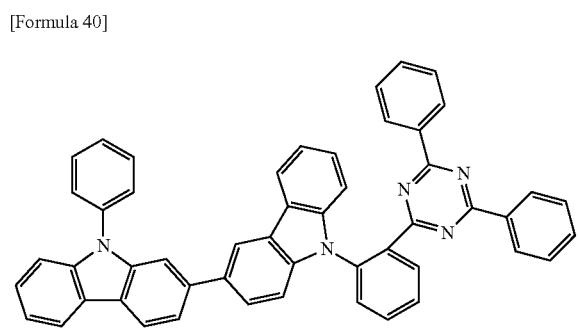
[Formula 41]
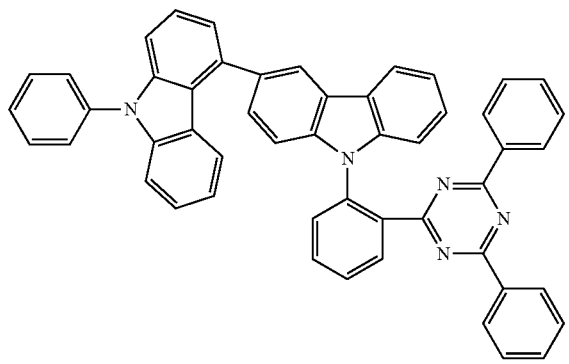
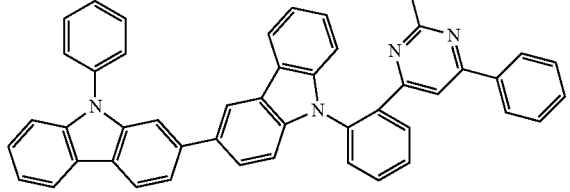

-continued
[Formula 42]
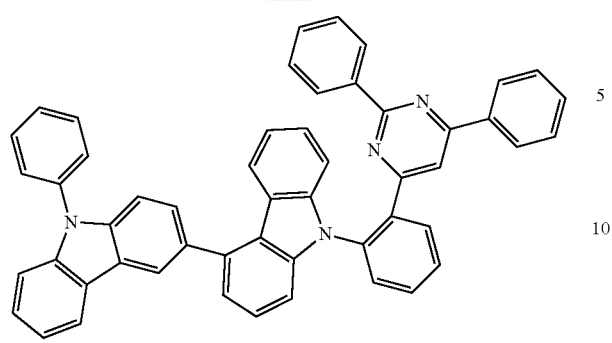
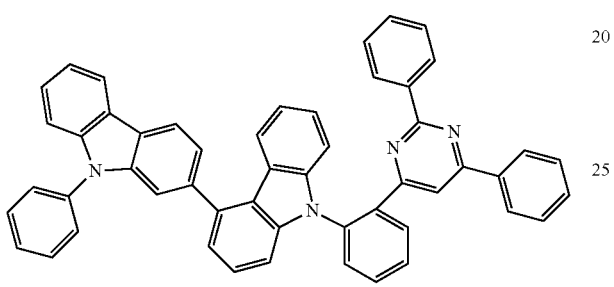
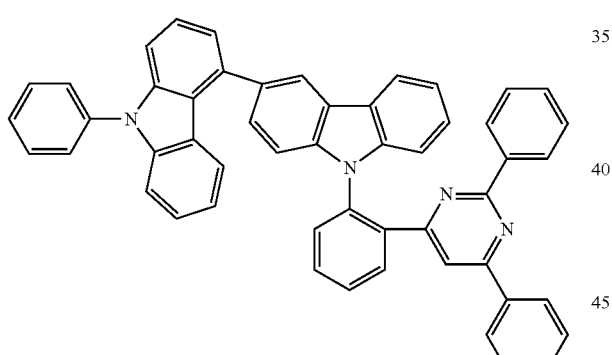
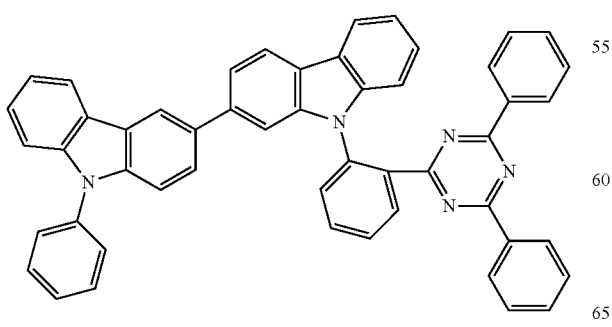
-continued
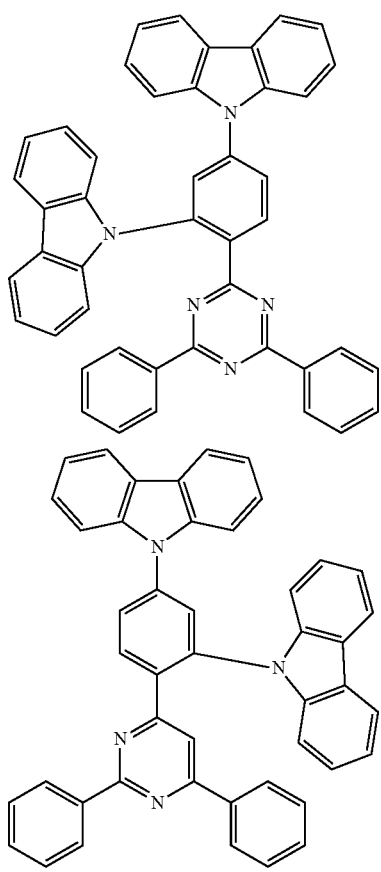
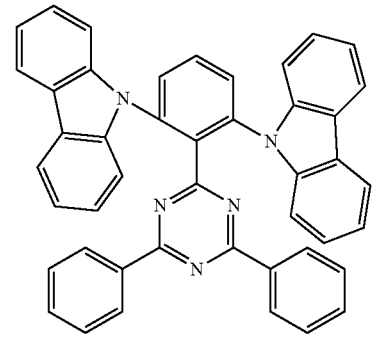
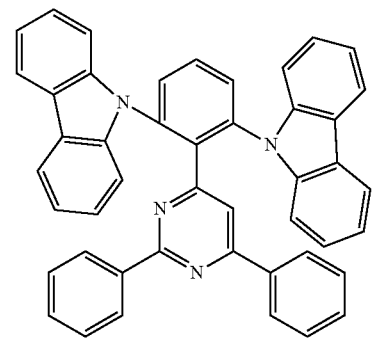

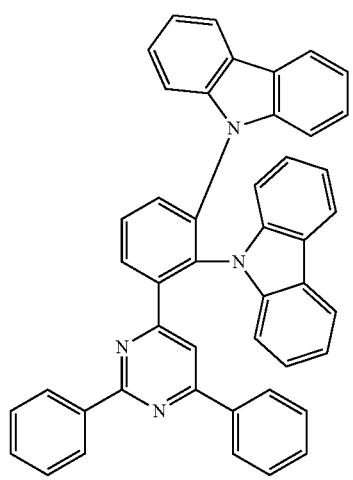
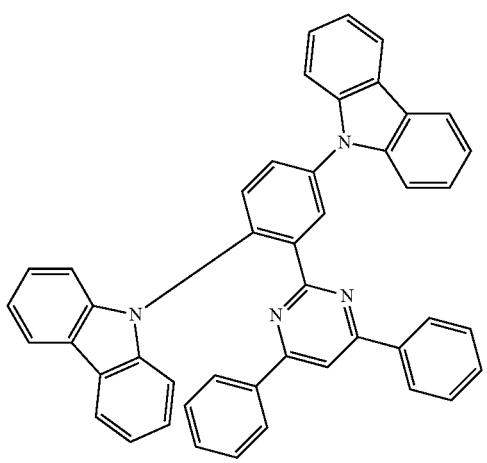
[Formula 43]
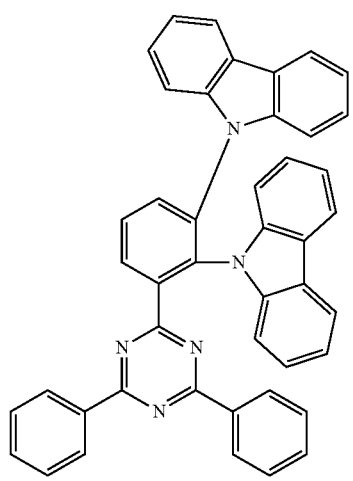
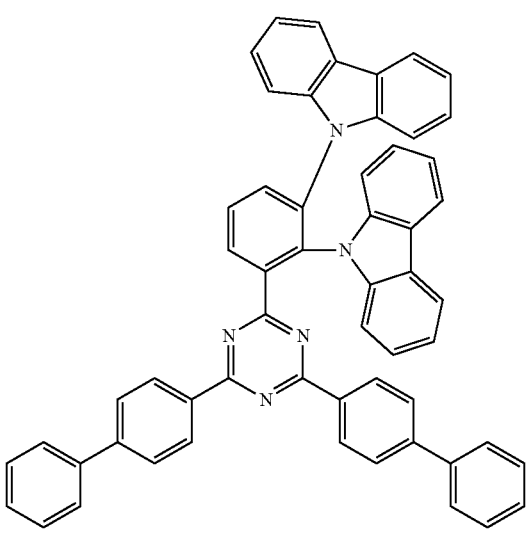
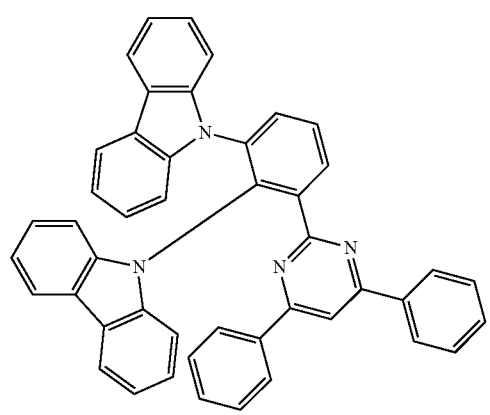
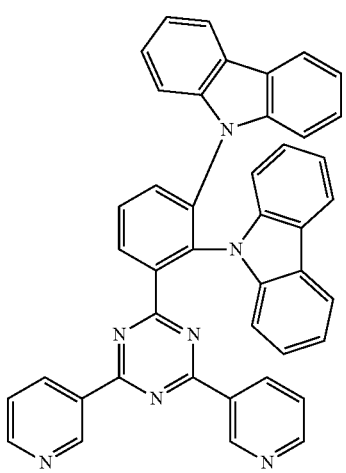

-continued
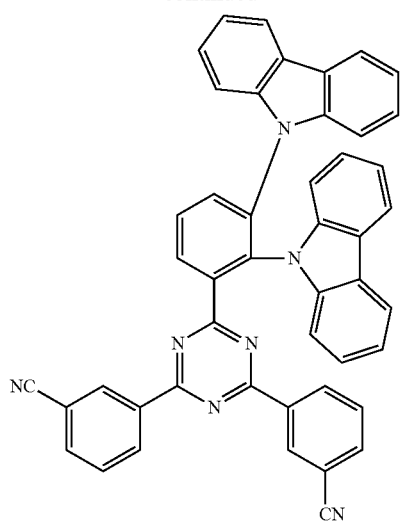
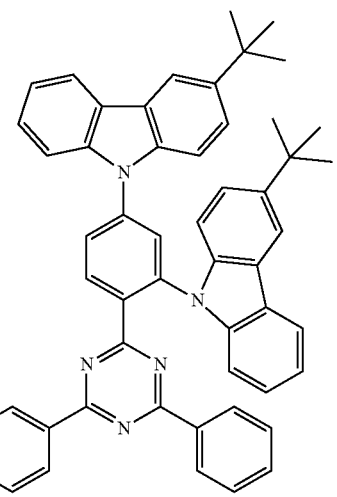
[Formula 45]
[Formula 44]
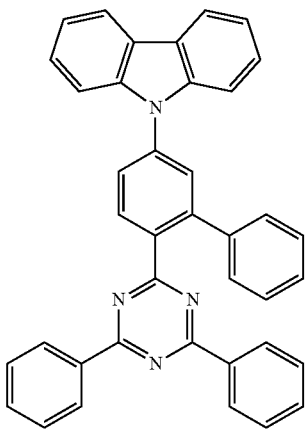
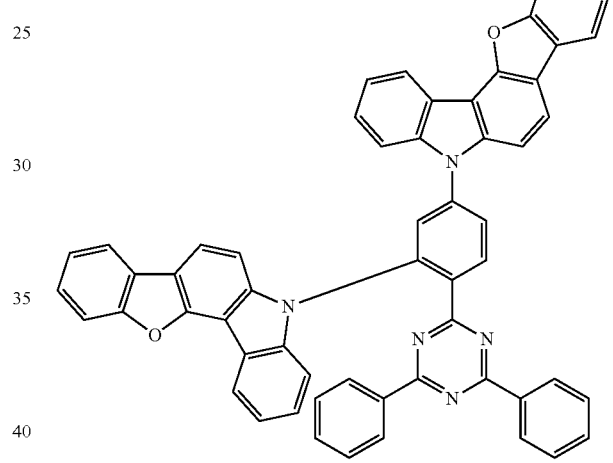
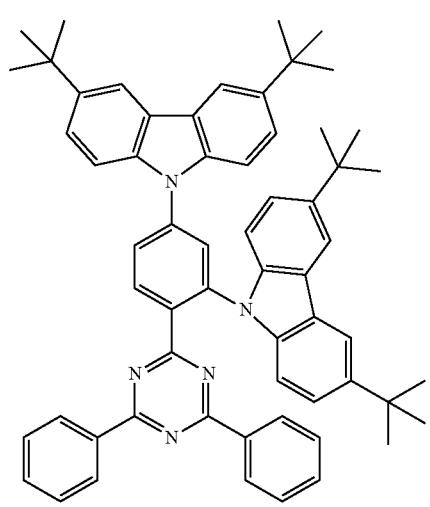
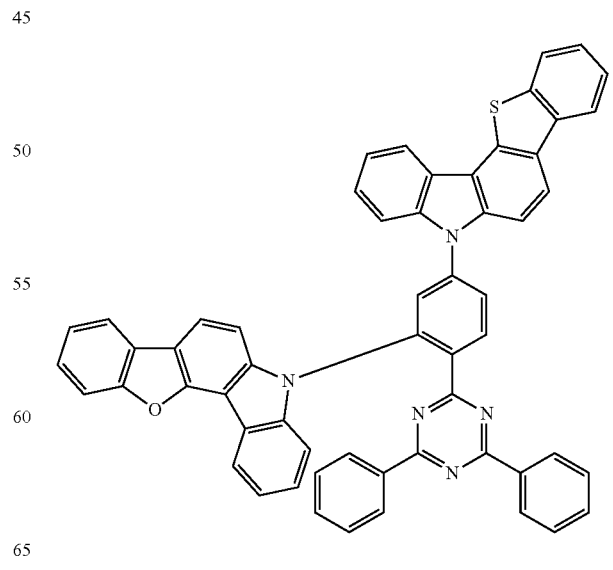

[Formula 46]
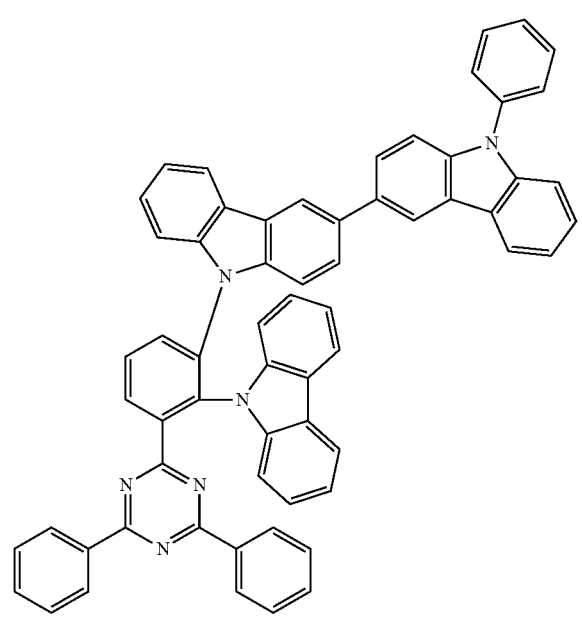
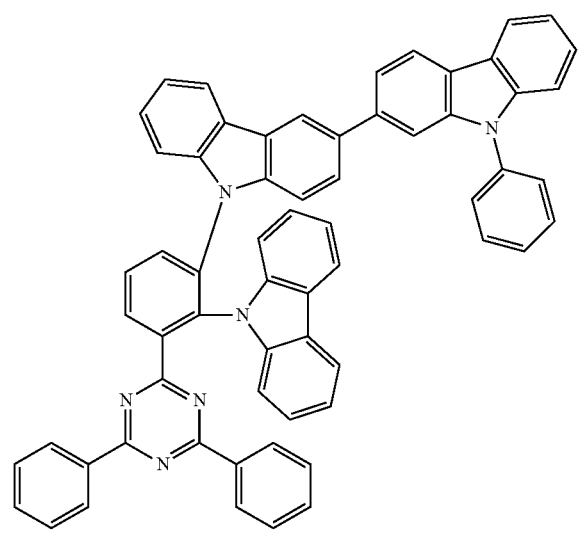
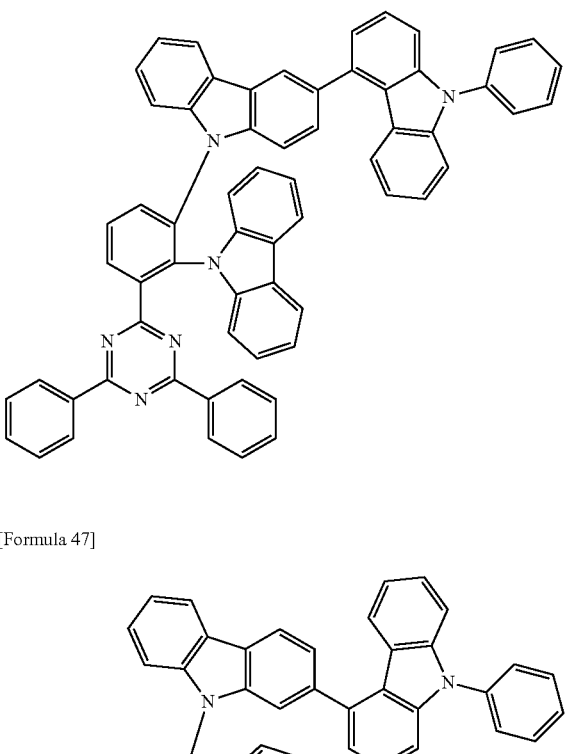
[Formula 47]
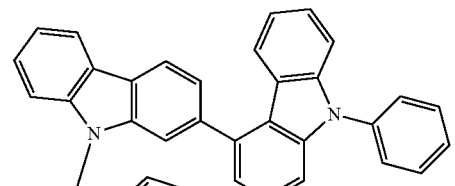
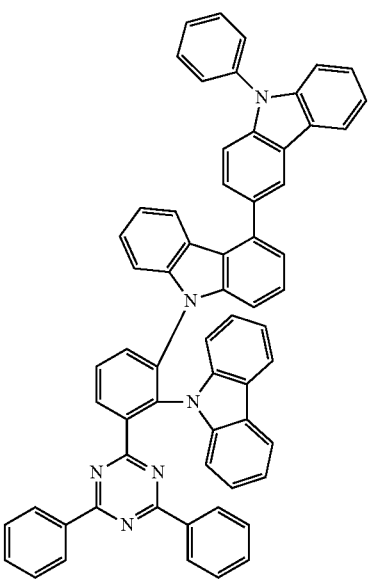

-continued
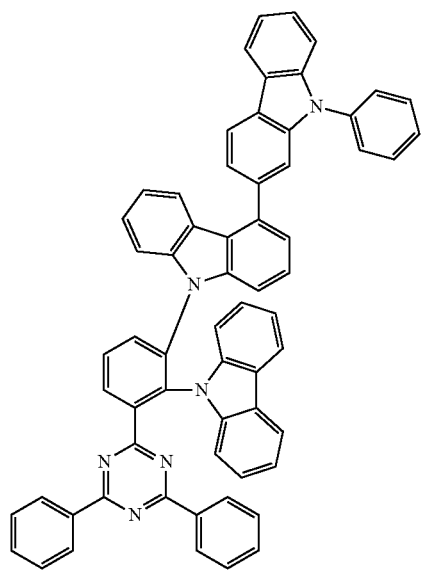
[Formula 48]
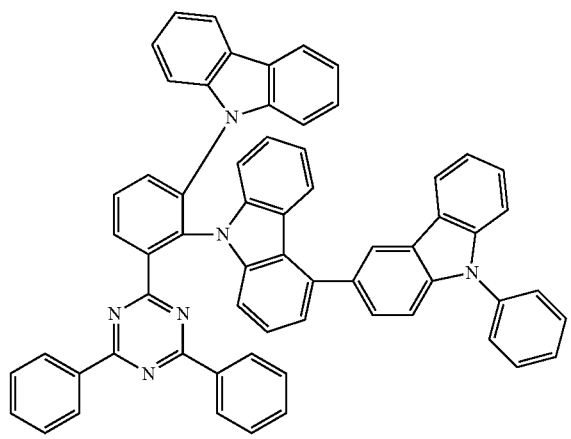
-continued
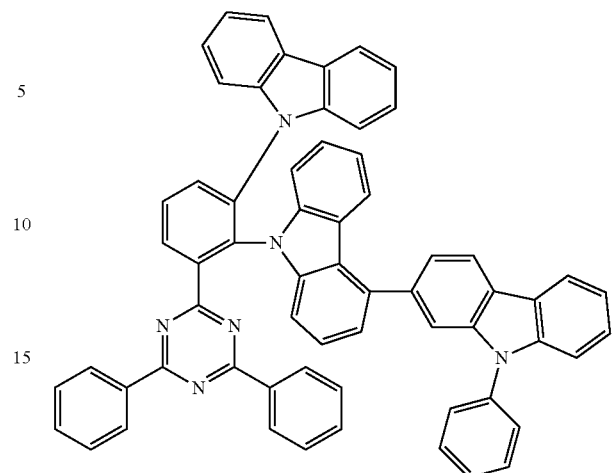
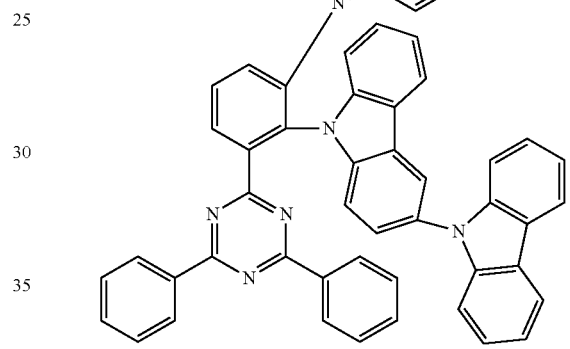
[Formula 49]
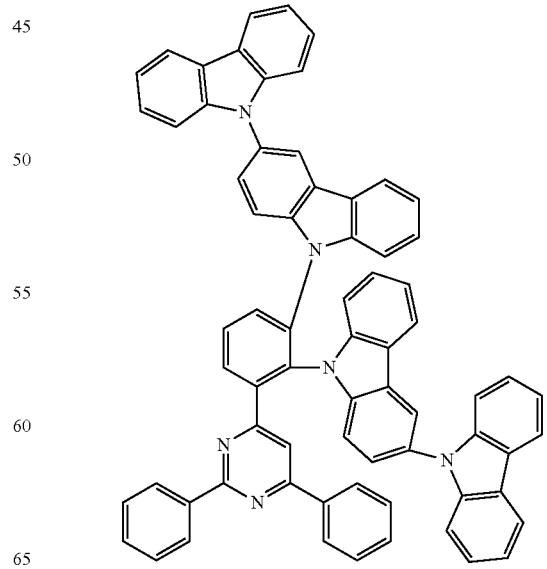

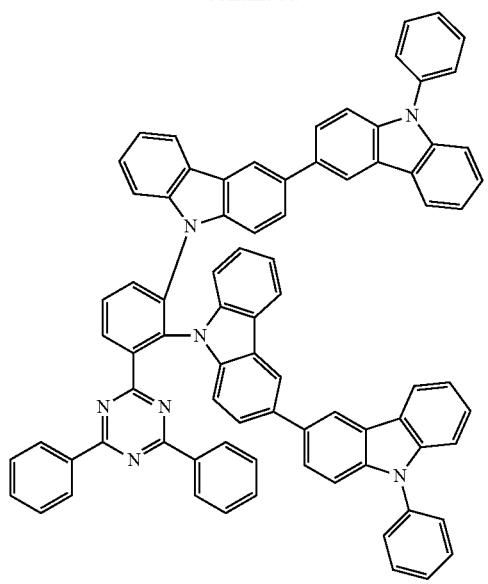
[Formula 50]
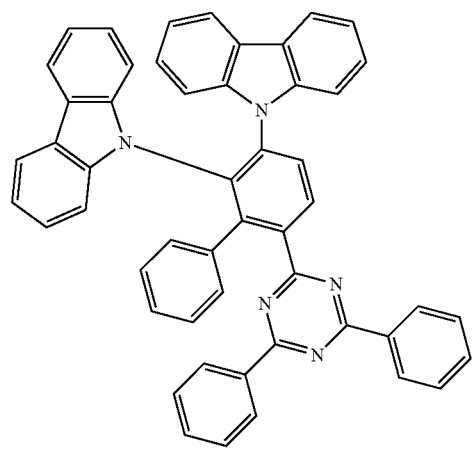
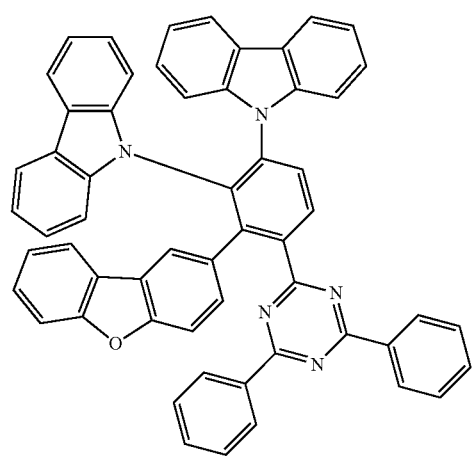
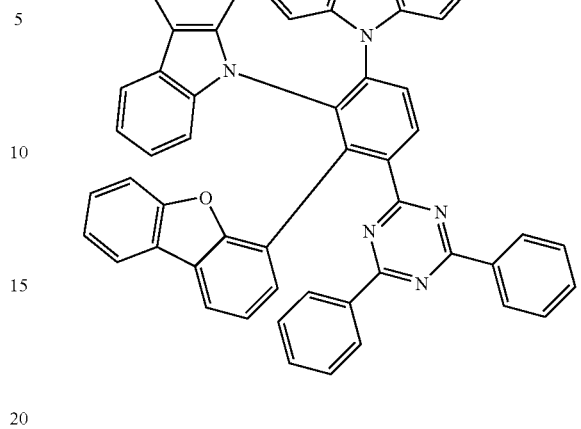
[Formula 51]
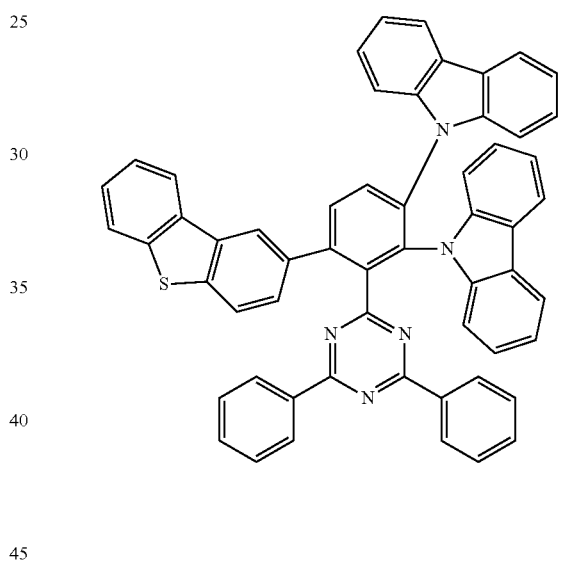
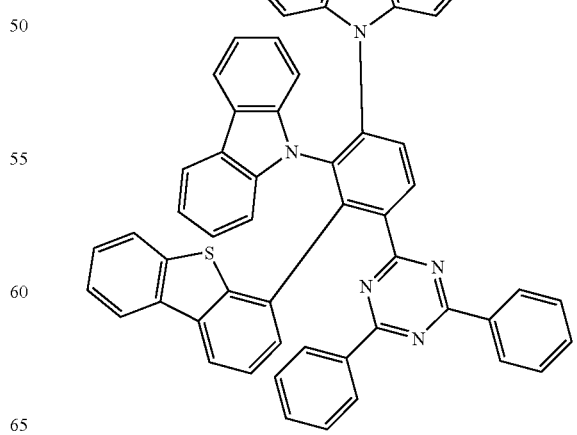

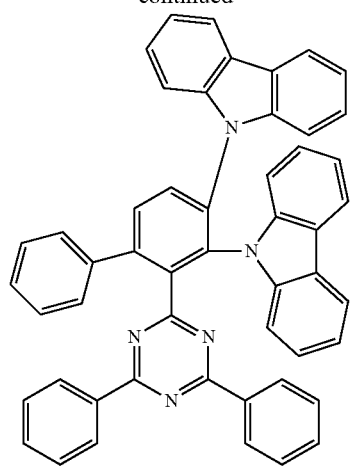
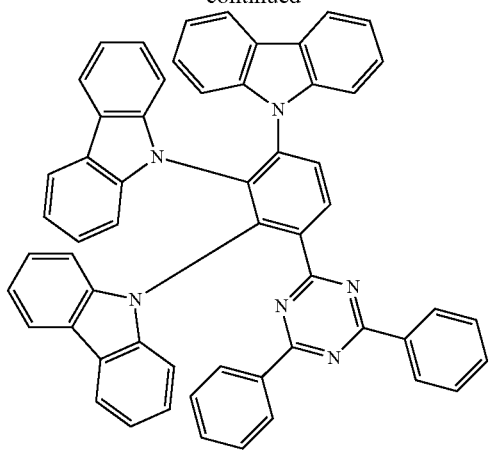
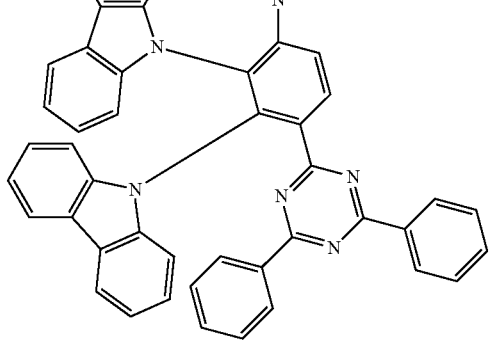
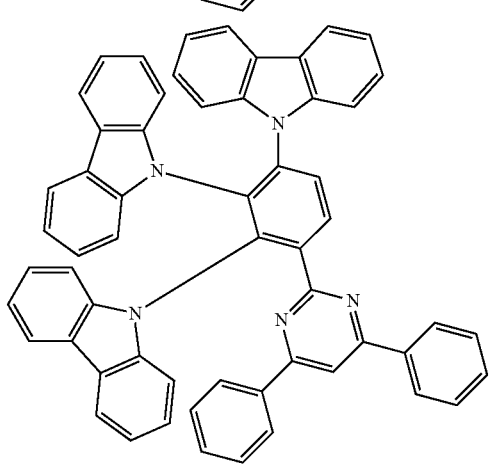
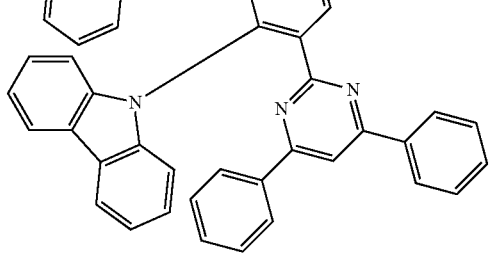
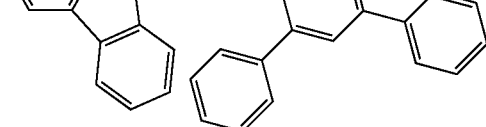
[Formula 52]
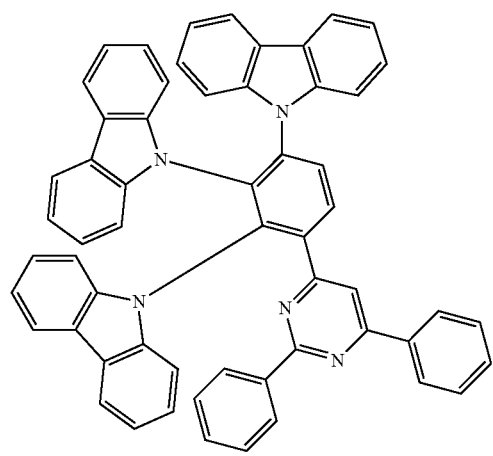

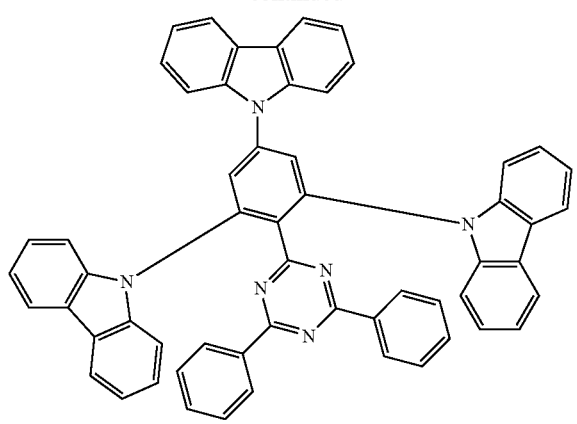
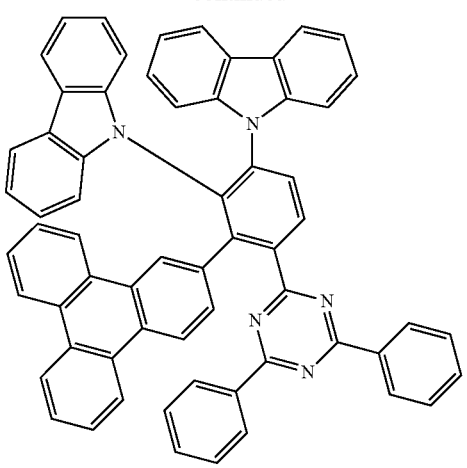
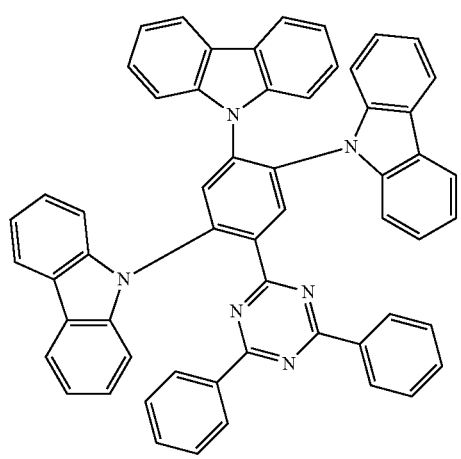
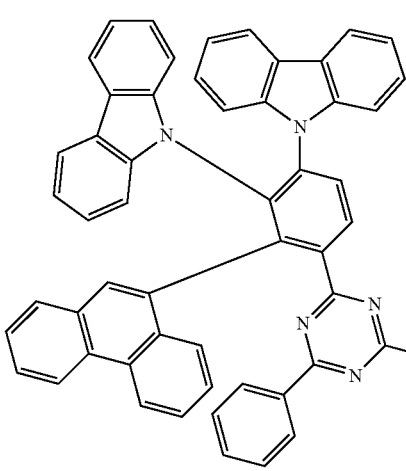
[Formula 53]
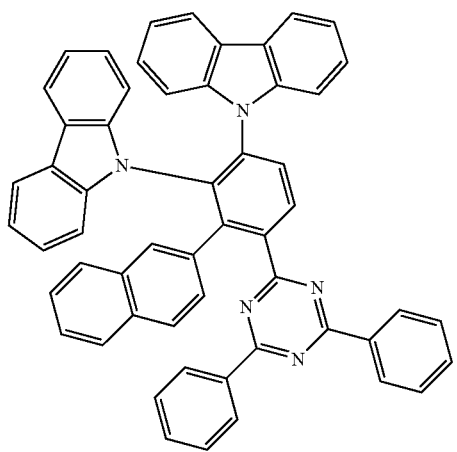
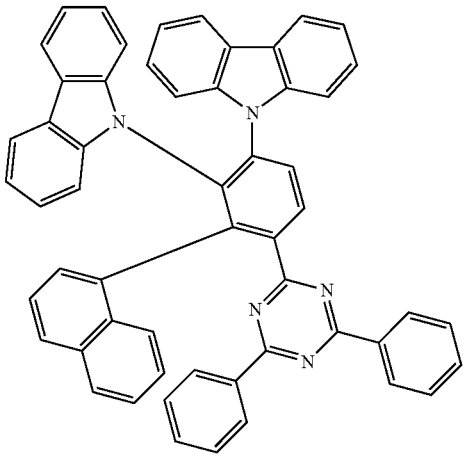

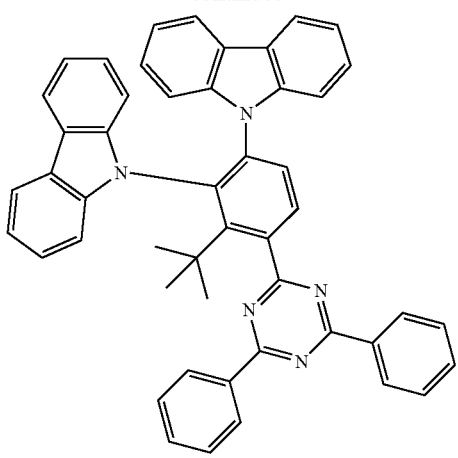
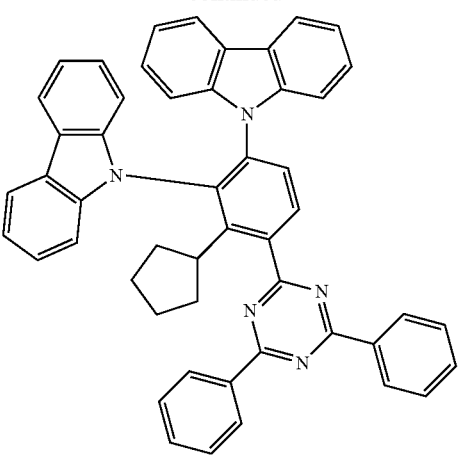
[Formula 54]
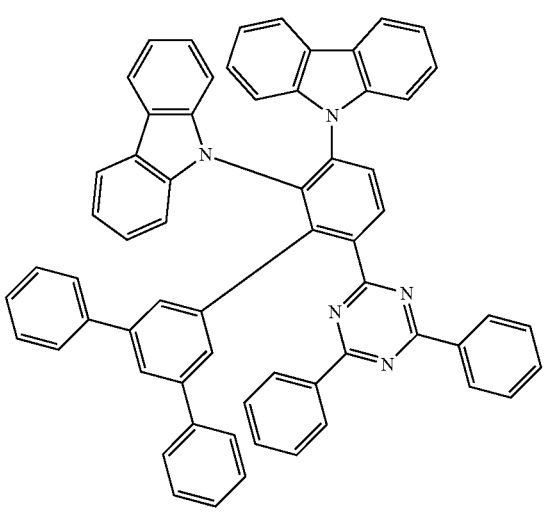
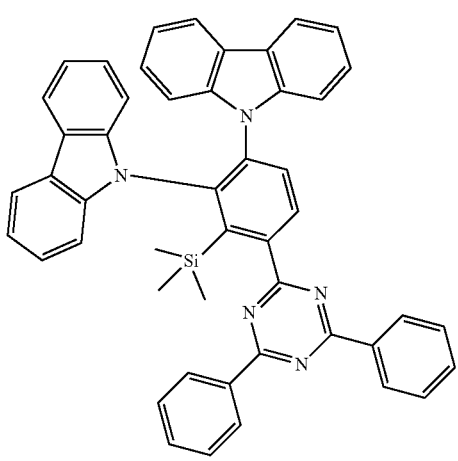
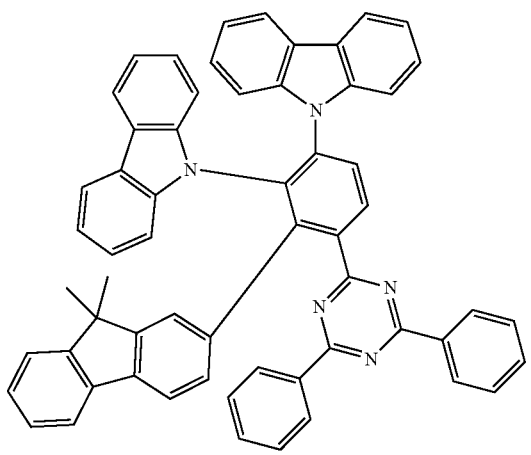
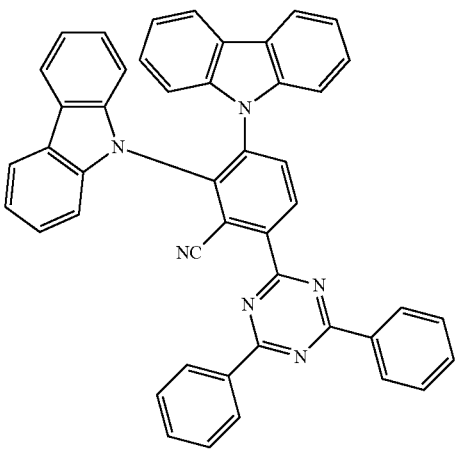

[Formula 55]
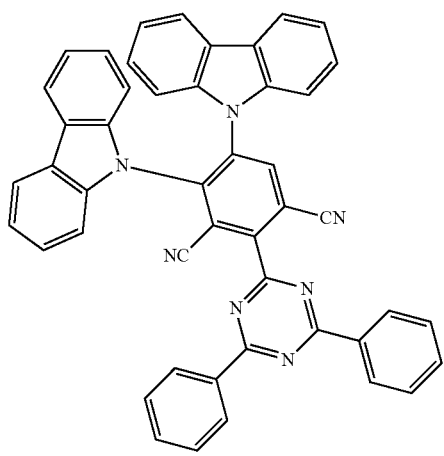
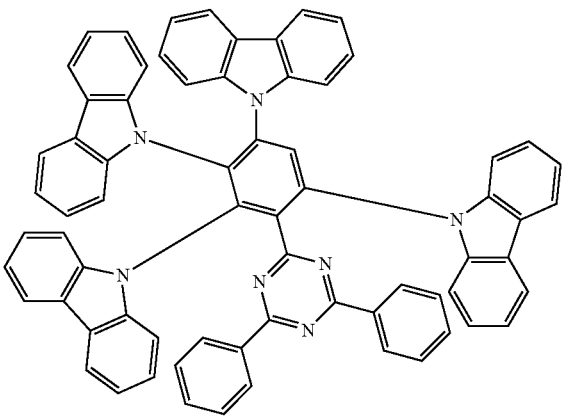
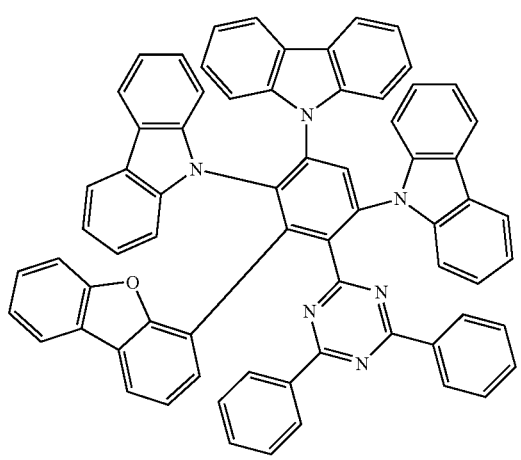
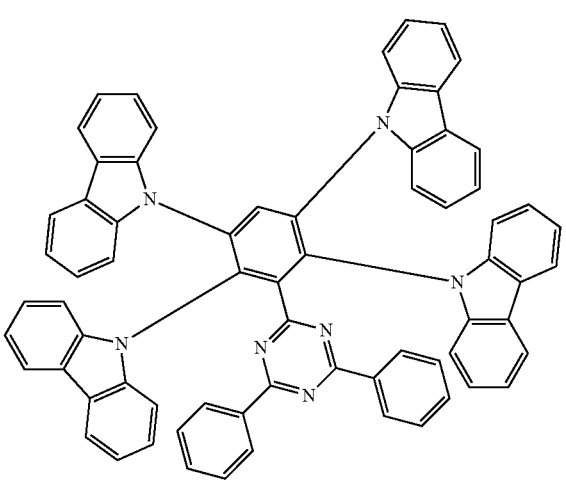
[Formula 56]
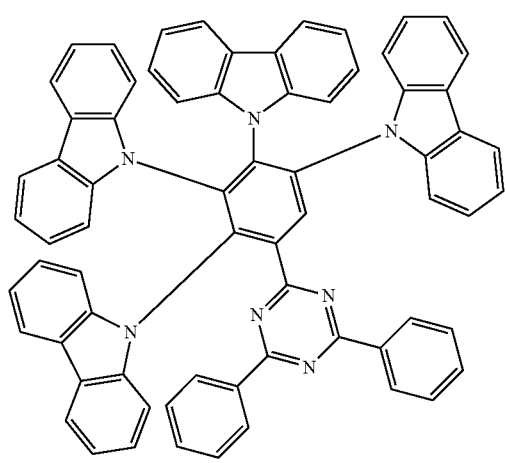
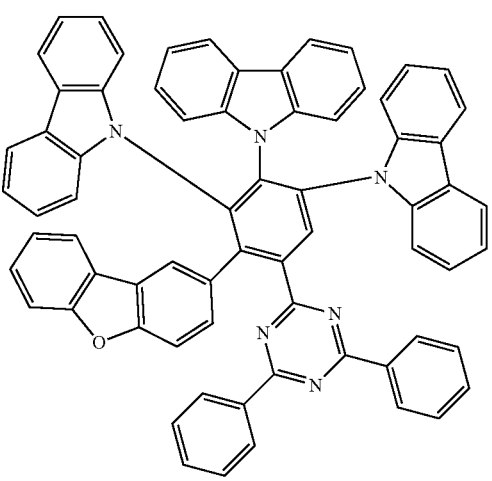

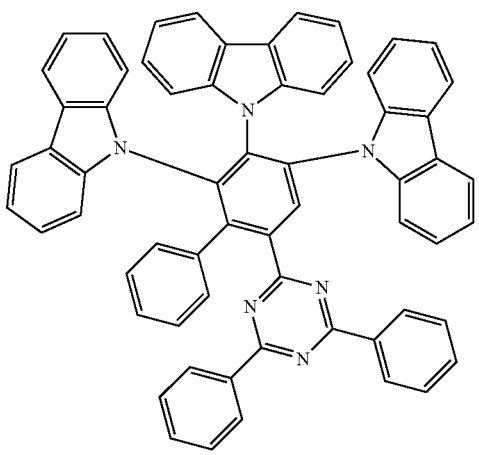

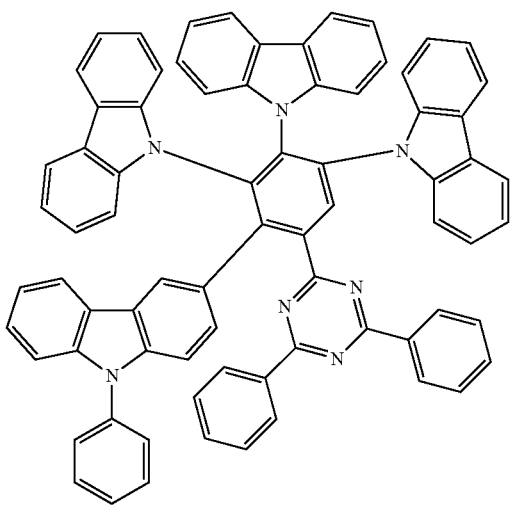

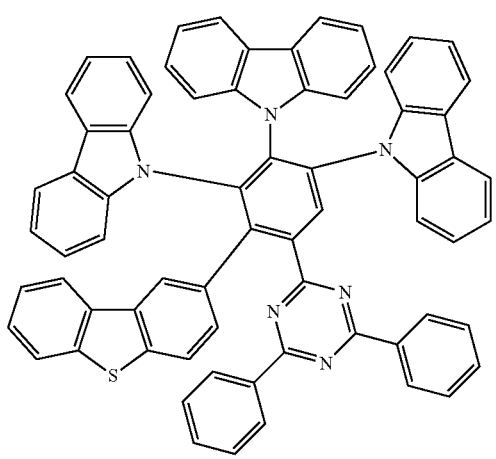

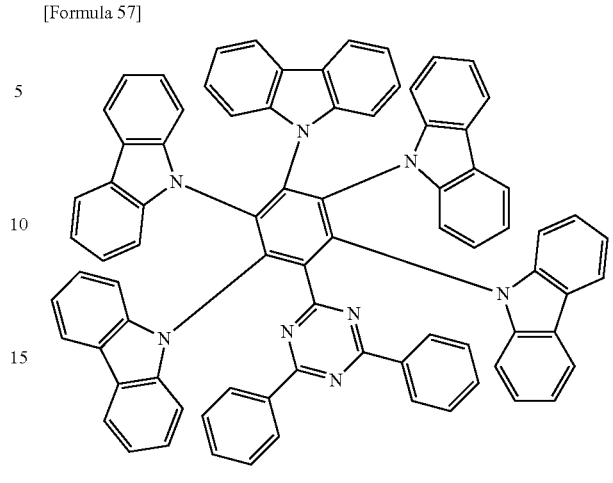

[Formula 57]

Organic-EL-Device Material

The compounds of the exemplary embodiment are applicable as an organic-EL-device material. The compounds of the exemplary embodiment may be singly used as the organic-EL-device material or a mixture of the compound(s) of the exemplary embodiment and other material may be used as the organic-EL-device material.

Organic EL Device

Arrangement(s) or an organic EL device according to the first exemplary embodiment will be described below.

The organic EL device includes an anode, a cathode and an organic layer interposed between the anode and the cathode. The organic layer includes one or more layer(s) formed from an organic compound. The organic layer may further contain an inorganic compound. The organic layer of the organic EL device of the exemplary embodiment includes at least one emitting layer. The organic layer may be provided by a single emitting layer. Alternatively, the organic layer may include layer(s) applied in a known organic EL device such as a hole injecting layer, a hole transporting layer, an electron injecting layer, an electron transporting layer, a hole blocking layer and an electron blocking layer.

FIG. 1 schematically shows an exemplary arrangement of an organic EL device according to the first exemplary embodiment.

An organic EL device 1 includes a light-transmissive substrate 2, an anode 3, a cathode 4, and an organic layer 10 interposed between the anode 3 and the cathode 4. The organic layer 10 includes a hole injecting layer 6, hole transporting layer 7, emitting layer 5, electron transporting layer 8, and electron injecting layer 9 which are sequentially laminated from the anode 3.

Emitting Layer

The emitting layer 5 of the organic EL device 1 contains a delayed-fluorescent compound according to the above-described first exemplary embodiment, and a fluorescent second compound. The compound of the first exemplary embodiment will be referred to as "a first compound" hereinafter.

The emitting layer 5 may include a metal complex. In the first exemplary embodiment, it is preferable that the emitting layer 5 does not contain a phosphorescent metal complex.

Since the organic EL device of the first exemplary embodiment contains the compound according to the first exemplary embodiment (first compound) and the fluorescent second compound, emission efficiency can be improved in the emitting layer. As described above, it is speculated that the emission efficiency is improved since inverse intersystem crossing is likely to occur in the first compound contained in the emitting layer and, as a result, singlet exited energy transfer from the first compound to the second compound increases to allow efficient light emission from the fluorescent second compound.

Second Compound

The second compound of the first exemplary embodiment is not particularly limited as long as the second compound is a fluorescent compound.

It is preferable that the second compound emits light with a main peak wavelength of 550 nm or less. Further, it is preferable that the second compound emits fluorescence with a main peak wavelength of 430 nm or more. The main peak wavelength means a peak wavelength of luminescence spectrum exhibiting a maximum luminous intensity among luminous spectra measured in a toluene solution in which the second compound is dissolved at a concentration from $10^{-6}$ mol/L to $10^{-5}$ mol/L.

The second compound preferably exhibits a green or blue fluorescence. Moreover, the second compound is preferably a material having a high emission quantum efficiency.

As the second compound in the first exemplary embodiment, a fluorescent material is usable. Examples of a blue fluorescent compound include a pyrene derivative, styrylamine derivative, chrysene derivative, fluoranthene derivative, fluorene derivative, diamine derivative, and triarylamine derivative. Examples of a green fluorescent compound include a coumarin derivative, pyrromethene boron complex, and aromatic amine derivative. Examples of a red fluorescent compound include a tetracene derivative, periflanthene derivative, pyrromethene boron complex, and diamine derivative.

The second compound of the first exemplary embodiment is also preferably a compound represented by a formula (20).

[Formula 58]

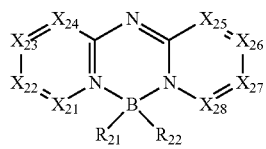

(20)

In the above formula (20), $R_{21}$ and $R_{22}$ are each independently a hydrogen atom or a substituent, and $R_{21}$ and $R_{22}$ as substituents are groups selected from the group consisting of a halogen atom, a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, and a carboxy group, $R_{21}$ and $R_{22}$ as the substituent being optionally directly bonded to form a ring, and $X_{21}$ to $X_{28}$ are each independently a carbon atom bonded to $R_{23}$ (C—$R_{23}$) or a nitrogen atom, $R_{23}$ being a hydrogen atom or a substituent selected from the group consisting of a halogen atom, a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, and a carboxy group, a plurality of $R_{23}$s as the substituents being mutually the same or different and directly bonded to each other to form a ring, being bonded through a hetero atom(s) to form a ring, or not forming a ring. The ring formed by bonding $R_{21}$ and $R_{22}$ as the substituents and the ring formed by bonding a plurality of $R_{23}$s as the substituents are each preferably a five-membered ring, a six-membered ring or a seven-membered ring, which may be any of an aliphatic ring, an aromatic hydrocarbon ring or a heterocyclic ring, and may be substituted, the plurality of rings being the same or different.

In the first exemplary embodiment, $X_{21}$ to $X_{28}$ are preferably each independently a carbon atom bonded to $R_{23}$. In this case, the second compound is represented by a formula (21). In the formula (21), $R_{231}$ to $R_{238}$ are each independently the same as the above-described $R_{23}$, and $R_{21}$ and $R_{22}$ are the same as the above-described $R_{21}$ and $R_{22}$.

[Formula 59]

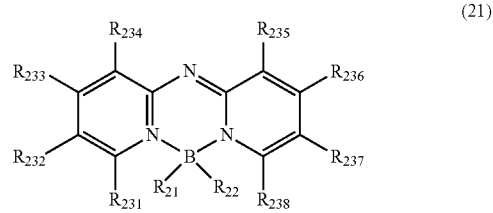

(21)

In the first exemplary embodiment, it is preferable that any of $R_{231}$ to $R_{234}$ are substituents bonded to each other to form a ring, or any of $R_{235}$ to $R_{238}$ are substituents bonded to each other to form a ring.

In the first exemplary embodiment, it is preferable that any of the substituents of $R_{231}$ to $R_{234}$ are bonded to each other to form a ring, and the substituents of $R_{235}$ to $R_{238}$ are bonded to each other to form a ring. The ring formed by bonding the substituents is preferably an aromatic hydrocarbon six-membered ring. The hydrocarbon six-membered ring may further be substituted.

The second compound of the first exemplary embodiment is also preferably a compound represented by a formula (22).

[Formula 60]

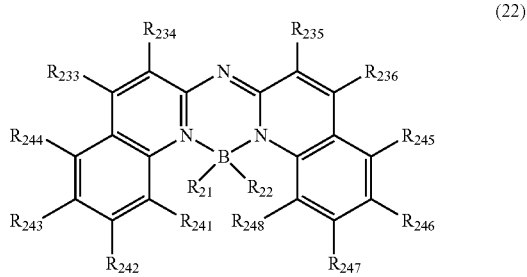

(22)

In the above formula (22), $R_{233}$ to $R_{236}$ and $R_{241}$ to $R_{248}$ each are independently the same as the above-described $R_{23}$, and $R_{21}$ and $R_{22}$ are the same as the above-described $R_{21}$ and $R_{22}$.

In the formula (22), it is preferable that $R_{241}$, $R_{242}$, $R_{244}$, $R_{245}$, $R_{247}$ and $R_{248}$ each are a hydrogen atom and $R_{243}$ and $R_{246}$ are each a substituent. $R_{243}$ and $R_{246}$ as the substituents are each independently a halogen atom or a group selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, and a carboxy group. $R_{243}$ and $R_{246}$ as the substituents preferably are each independently a halogen atom or a group selected from the group consisting of a substituted or unsubstituted aryl group having 6 to 30 ring carbon atoms and a substituted or unsubstituted alkyl group having 1 to 30 carbon atoms, more preferably a substituted or unsubstituted aryl group having 6 to 30 ring carbon atoms.

The substituents $R_{21}$ and $R_{22}$ in the first exemplary embodiment are preferably each independently selected from the group consisting of a halogen atom, a substituted or unsubstituted aryl group having 1 to 30 ring carbon atoms and an alkyl group having 1 to 30 carbon atoms, more preferably a halogen atom, and further more preferably a fluorine atom.

Specific examples of the second compound of the first exemplary embodiment are shown below. It should be noted that the second compound in the first exemplary embodiment is not limited thereto.

[Formula 61]

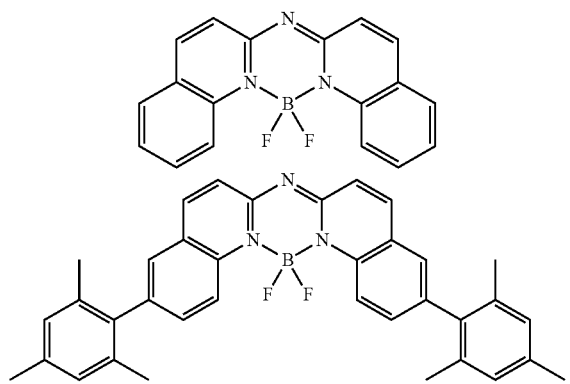

TADF Mechanism

In the organic EL device of the first exemplary embodiment, the first compound is preferably a compound having a small ΔST(M1) so that inverse intersystem crossing from the triplet energy level of the first compound to the singlet energy level thereof is easily caused by a heat energy given from the outside. An energy state conversion mechanism to perform spin exchange from the triplet state of electrically excited excitons within the organic EL device to the singlet state by inverse intersystem crossing is referred to as a TADF mechanism.

Figure 4:
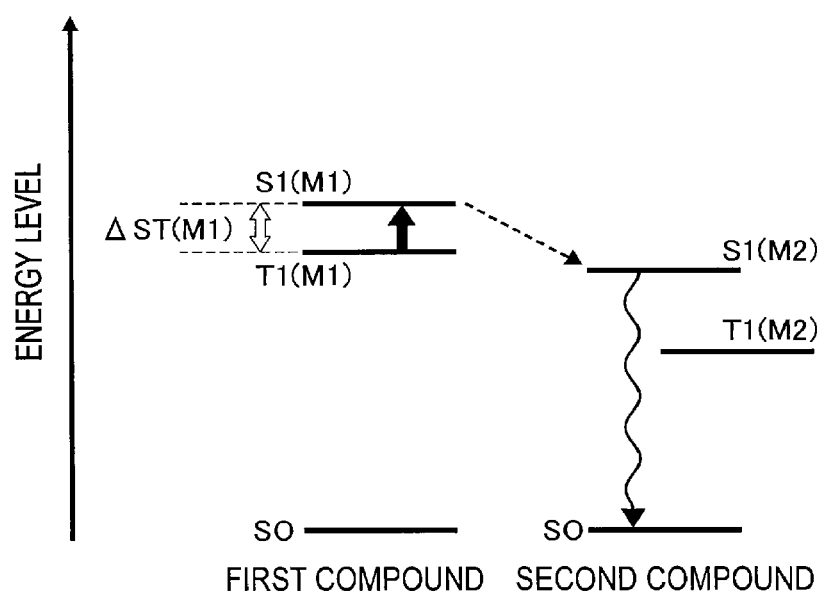
FIG. 4 shows a relationship between an energy level and an energy transfer of compounds contained in an emitting layer in the first exemplary embodiment.

FIG. 4 shows a relationship between energy levels of the first and second compounds in the emitting layer. In FIG. 4, S0 represents a ground state, S1(M1) represents a lowest singlet state of the first compound, T1(M1) represents a lowest triplet state of the first compound, S1(M2) represents a lowest singlet state of the second compound, and T1(M2) represents a lowest triplet state of the second compound. A dashed arrow directed from S1(M1) to S1(M2) in FIG. 4 represents Förster energy transfer from the lowest singlet state of the first compound to the lowest singlet state of the second compound. A difference between the lowest singlet state S1 and the lowest triplet state T1 is defined as ΔST.

As shown in FIG. 4, when a compound having a small ΔST(M1) is used as the first compound, inverse intersystem crossing from the lowest triplet state T1(M1) to the lowest singlet state S1(M1) can be caused by a heat energy. Consequently, Förster energy transfer from the lowest singlet state S1(M1) of the first compound to the lowest singlet state S1(M2) of the second compound is caused. As a result, fluorescence from the lowest singlet state S1(M2) of the second compound can be observed. It is speculated that the internal quantum efficiency can be theoretically raised up to 100% also by using the delayed fluorescence by the TADF mechanism.

In the first exemplary embodiment, a singlet energy S(M1) of the first compound is preferably larger than the singlet energy S(M2) of the second compound.

Further, in the first exemplary embodiment, an energy gap $T_{77K}$(M1) at 77 [K] of the first compound is preferably larger than an energy gap $T_{77K}$(M2) at 77 [K] of the second compound. $T_{77K}$(M1) is preferably 2.0 eV or more, more preferably 2.2 eV or more.

Relationship Between Triplet Energy and Energy Gap at 77 [K]

Description will be made on a relationship between a triplet energy and an energy gap at 77 [K]. In the first exemplary embodiment, the energy gap at 77 [K] is different from a triplet energy as typically defined in some aspects.

The triplet energy is measured as follows. Initially, a sample in which a target compound is vapor-deposited on a quartz substrate, or a sample in which a target compound dissolved in an appropriate solvent is sealed in a quartz glass tube is prepared. A phosphorescent spectrum (ordinate axis: phosphorescent luminous intensity, abscissa axis: wavelength) of the sample is measured at a low temperature (77K). A tangent is drawn to the rise of the phosphorescent spectrum on the short-wavelength side. The triplet energy is calculated by a predetermined conversion equation based on a wavelength value at an intersection of the tangent and the abscissa axis.

The first compound used in the first exemplary embodiment is preferably a compound having a small ΔST. When ΔST is small, intersystem crossing and inverse intersystem crossing are likely to occur even at a low temperature (77 [K]), so that the singlet state and the triplet state coexist. As a result, the spectrum to be measured in the same manner as the above includes emission from both the singlet state and the triplet state. Although it is difficult to distinguish the emission from the singlet state from the emission from the triplet state, the value of the triplet energy is basically considered dominant.

Accordingly, in the first exemplary embodiment, the triplet energy is measured by the same method as a typical triplet energy T, but a value measured in the following manner is referred to as an energy gap $T_{77K}$ in order to differentiate the measured energy from the typical triplet energy in a strict meaning. When a thin film is used for the measurement, the target compound is vapor-deposited on a quartz substrate at a film thickness of 100 nm to prepare a sample. A phosphorescent spectrum (ordinate axis: phosphorescent luminous intensity, abscissa axis: wavelength) of the sample is measured at a low temperature (77K). A tangent is drawn to the rise of the phosphorescent spectrum on the short-wavelength side. The energy gap $T_{77K}$ is calculated by a conversion equation 1 below based on a wavelength value λedge (nm) at an intersection of the tangent and the abscissa axis.

$$T_{77K} [eV]=1239.85/\lambda\text{edge} \qquad \text{Conversion equation 1:}$$

The tangent to the rise of the phosphorescence spectrum on the short-wavelength side was drawn as follows. While moving on a curve of the phosphorescence spectrum from the short-wavelength side to the maximum spectral value closest to the short-wavelength side among the maximum spectral values, a tangent was checked at each point on the curve toward the long-wavelength of the phosphorescence spectrum. An inclination of the tangent was increased as the curve rose (i.e., a value of the ordinate axis was increased). A tangent drawn at a point of the maximum inclination (i.e., a tangent at an inflection point) was defined as the tangent to the rise of the phosphorescence spectrum on the short-wavelength side.

The maximum with peak intensity being 15% or less of the maximum peak intensity of the spectrum is not included in the above-mentioned maximum closest to the short-wavelength side of the spectrum. The tangent drawn at a point of the maximum spectral value being closest to the short-wavelength side and having the maximum inclination is defined as a tangent to the rise of the phosphorescence spectrum on the short-wavelength side.

For phosphorescence measurement, a spectrophotofluorometer body F-4500 (manufactured by Hitachi High-Technologies Corporation) is usable. The measurement instrument is not limited to this arrangement. A combination of a cooling unit, a low temperature container, an excitation light source and a light-receiving unit may be used for measurement.

Singlet Energy S

Singlet energy S is measured as follows.

A 10 μmol/L toluene solution of a measurement target compound was manufactured and put in a quartz cell. An absorption spectrum (ordinate axis: luminous intensity, abscissa axis: wavelength) of the thus-obtained sample was measured at a normal temperature (300K). A tangent was drawn to the fall of the absorption spectrum on the long-wavelength side, and a wavelength value λedge (nm) at an intersection of the tangent and the abscissa axis was assigned to a conversion equation 2 below to calculate singlet energy.

$$S (eV)=1239.85/\lambda\text{edge} \qquad \text{Conversion equation 2:}$$

In Examples, the absorption spectrum was measured using a spectrophotometer (U3310 manufactured by Hitachi, Ltd.). It should be noted that the absorption spectrum measuring device may be different from the above device.

The tangent to the fall of the absorption spectrum on the long-wavelength side is drawn as follows. While moving on a curve of the absorption spectrum from the maximum spectral value closest to the long-wavelength side in a long-wavelength direction, a tangent at each point on the curve was checked. An inclination of the tangent was decreased and increased in a repeated manner as the curve fell (i.e., a value of the ordinate axis was decreased). A tangent drawn at a point of the minimum inclination closest to the long-wavelength side (except when absorbance was 0.1 or less) was defined as the tangent to the fall of the absorption spectrum on the long-wavelength side.

The maximum absorbance of 0.2 or less is not included in the above-mentioned maximum absorbance on the long-wavelength side.

Film Thickness of Emitting Layer

A film thickness of the emitting layer 5 of the organic EL device 1 in the first exemplary embodiment is preferably in a range of 5 nm to 100 nm, more preferably in a range of 7 nm to 100 nm, further preferably in a range of 10 nm to 100 nmnm. When the film thickness is 5 nm or more, the emitting layer 5 can be easily formed and chromaticity can be easily adjusted. At the film thickness of 100 nm or less, increase in the drive voltage is suppressible.

Content Ratio of Compounds in Emitting Layer

In the emitting layer 5 of the organic EL device 1 of the first exemplary embodiment, a content ratio of the first compound is preferably 5 mass % or more, more preferably in a range from 10 mass % to 80 mass %, further preferably in a range from 40 mass % to 60 mass %. A content ratio of the second compound is preferably in a range from 1 mass % to 10 mass %.

Supposing that the emitting layer 5 is substantially consisted only of the first compound and the second compound, the content of the first compound is preferably in a range from 90 mass % to 99 mass %, and the content of the second compound is preferably in a range from 1 mass % to 10 mass %. In the above, the term "substantially" means that there are instances where only the first and the second compounds are contained in the emitting layer 5, and the emitting layer 5 contains a minute amount of inevitable impurities derived from, for instance, the materials for forming the emitting layer. An upper limit of a total content ratio of the first and second compounds in the emitting layer 5 is 100 mass %. It should be noted that the first exemplary embodiment does not exclude an arrangement in which a material other than the first compound and the second compound is contained in the emitting layer 5.

Substrate

A substrate 2 is used as a support for the organic EL device 1. Examples of the substrate 2 include a glass substrate, quartz substrate, and plastic substrate. A flexible substrate is also usable. The flexible substrate is a substrate that is adapted to be bent. Examples of the flexible substrate include plastic substrates formed from polycarbonate, polyarylate, polyethersulfone, polypropylene, polyester, polyvinyl fluoride, polyvinyl chloride, polyimide, and polyethylene naphthalate. Moreover, an inorganic vapor deposition film is also usable for the substrate 2.

Anode

Preferable examples of a material for the anode 3 formed on the substrate 2 include metal, an alloy, an electroconductive compound, and a mixture thereof, which have a large work function (specifically, 4.0 eV or more). Specific examples of the material include indium oxide-tin oxide (ITO: Indium Tin Oxide), indium oxide-tin oxide containing silicon or silicon oxide, indium oxide-zinc oxide, and indium oxide containing tungsten oxide and zinc oxide, and graphene. In addition, gold (Au), platinum (Pt), nickel (Ni), tungsten (W), chrome (Cr), molybdenum (Mo), iron (Fe), cobalt (Co), copper (Cu), palladium (Pd), titanium (Ti), or nitrides of a metal material (e.g., titanium nitride) are usable.

The above materials are typically deposited as a film by sputtering. For instance, indium zinc oxide can be deposited as a film by sputtering using a target that is obtained by adding zinc oxide in a range from 1 mass % to 10 mass % to indium oxide. Moreover, for instance, the indium oxide containing tungsten oxide and zinc oxide can be formed by the sputtering method using a target in which tungsten oxide in a range from 0.5 mass % to 5 mass % and zinc oxide in a range from 0.1 mass % to 1 mass % are added to indium oxide. In addition, the anode 3 may be formed by a vacuum deposition method, a coating method, an inkjet method, a spin coating method or the like.

Among the organic layers formed on the anode 3, since the hole injecting layer 6 abutting on the anode 3 is formed of a composite material into which holes are easily injectable irrespective of the work function of the anode 3, a material usable as an electrode material (e.g., metal, an alloy, an electroconductive compound, a mixture thereof, and the elements belonging to the group 1 or 2 of the periodic table) is also usable for the anode 3.

The elements belonging to the group 1 or 2 of the periodic table, which are a material having a small work function, specifically, an alkali metal such as lithium (Li) and cesium (Cs), an alkaline earth metal such as magnesium (Mg), calcium (Ca) and strontium (Sr), an alloy containing the alkali metal and the alkaline earth metal (e.g., MgAg, AlLi), a rare earth metal such as europium (Eu) and ytterbium (Yb), and an alloy containing the rare earth metal are usable for the anode 3. It should be noted that the vacuum deposition method and the sputtering method are usable for forming the anode 3 using the alkali metal, alkaline earth metal and the alloy thereof. Further, when a silver paste is used for the anode 3, the coating method and the inkjet method are usable.

Hole Injecting Layer

The hole injecting layer 6 is a layer containing a highly hole-injectable substance. Examples of the substance exhibiting a high hole injectability include molybdenum oxide, titanium oxide, vanadium oxide, rhenium oxide, ruthenium oxide, chrome oxide, zirconium oxide, hafnium oxide, tantalum oxide, silver oxide, tungsten oxide, and manganese oxide.

Moreover, examples of the substance exhibiting a high hole injectability further include: an aromatic amine compound, which is a low molecular organic compound, such as 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), 4,4'-bis[N-(4-diphenylaminophenyl)-N-phenylamino]biphenyl (abbreviation: DPAB), 4,4'-bis(N-{4-[N'-(3-methylphenyl)-N'-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), 3-[N-(9-phenylcarbazole-3-yl)-N-phenylamino]-9-phenylcarbazole (abbreviation: PCzPCA1), 3,6-bis[N-(9-phenylcarbazole-3-yl)-N-phenylamino]-9-phenylcarbazole (abbreviation: PCzPCA2), and 3-[N-(1-naphthyl)-N-(9-phenylcarbazole-3-yl)amino]-9-phenylcarbazole (abbreviation: PCzPCN1); and dipyrazino[2,3-f:20,30-h]quinoxaline-2,3,6,7,10,11-hexacarbonitrile (HAT-CN).

In addition, a high polymer compound (e.g., oligomer, dendrimer and polymer) is usable as the substance exhibiting a high hole injectability. Examples of the high polymer compound include poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), and poly[N,N'-bis(4-butylphenyl)-N,N'-bis(phenyl)benzidine] (abbreviation: Poly-TPD). Moreover, an acid-added high polymer compound such as poly(3,4-ethylenedioxythiophene)/poly(styrene sulfonic acid) (PEDOT/PSS) and polyaniline/poly (styrene sulfonic acid) (PAni/PSS) are also usable.

Hole Transporting Layer

The hole transporting layer 7 is a layer containing a highly hole-transporting substance. An aromatic amine compound, carbazole derivative, anthracene derivative and the like are usable for the hole transporting layer 7. Specific examples of the substance usable for the hole transporting layer 6 include an aromatic amine compound such as 4,4'-bis[N-(1-naphthyl)-N-phenylamino]biphenyl (abbreviation: NPB), N,N'-bis(3-methylphenyl)-N,N'-diphenyl-[1,1'-biphenyl]-4,4'-diamine (abbreviation: TPD), 4-phenyl-4'-(9-phenylfluorene-9-yl)triphenylamine (abbreviation: BAFLP), 4,4'-bis[N-(9,9-dimethylfluorene-2-yl)-N-phenylamino]biphenyl (abbreviation: DFLDPBi), 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), and 4,4'-bis[N-(spiro-9,9'-bifluorene-2-yl)-N-phenylamino]biphenyl (abbreviation: BSPB). The above-described substances mostly have a hole mobility of $10^{-6}$ cm$^2$/(V·s) or more.

For the hole transporting layer 7, a carbazole derivative such as CBP, 9-[4-(N-carbazolyl)]phenyl-10-phenyl anthracene (CzPA), and 9-phenyl-3-[4-(10-phenyl-9-anthryl)phenyl]-9H-carbazole (PCzPA) and an anthracene derivative such as t-BuDNA, DNA, and DPAnth may be used. A high polymer compound such as poly(N-vinylcarbazole) (abbreviation: PVK) and poly(4-vinyltriphenylamine) (abbreviation: PVTPA) is also usable.

However, any substance having a hole transporting performance higher than an electron transporting performance may be used in addition to the above substances. A layer containing the highly hole-transporting substance may be provided in the form of a single layer or a laminate of two or more layers.

When two or more hole transporting layers are provided, one of the hole transporting layers containing a material having a larger energy gap is preferably provided closer to the emitting layer 5.

In the first exemplary embodiment, the hole transporting layer 7 preferably has a function to prevent triplet excitons generated in the emitting layer 5 from diffusing to the hole transporting layer 7 and trap the triplet excitons in the emitting layer 5.

Electron Transporting Layer

The electron transporting layer 8 is a layer containing a highly electron-transporting substance. For the electron transporting layer 8, 1) a metal complex such as an aluminum complex, beryllium complex, and zinc complex, 2) a hetero aromatic compound such as imidazole derivative, benzimidazole derivative, azine derivative, carbazole derivative, and phenanthroline derivative, and 3) a high polymer compound are usable. Specifically, as a low molecular organic compound, the metal complex such as Alq, tris(4-methyl-8-quinolinolato)aluminum (abbreviation: Almq3), bis(10-hydroxybenzo[h]quinolinato)beryllium (abbreviation: BeBq2), BAlq, Znq, ZnPBO, and ZnBTZ are usable. In addition to the metal complex, the hetero aromatic compound such as 2-(4-biphenylyl)-5-(4-tert-butylphenyl)-1,3,4-oxadiazole (abbreviation: PBD), 1,3-bis[5-(ptert-butylphenyl)-1,3,4-oxadiazole-2-yl]benzene (abbreviation: OXD-7), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproine (abbreviation: BCP), and 4,4'-bis(5-methylbenzooxazole-2-yl)stilbene (abbreviation: BzOs) are usable. In the above exemplary embodiments, a benzimidazole compound is suitably usable. The above-described substances mostly have an electron mobility of $10^{-6}$ cm$^2$/(V·s) or more. However, any substance having an electron transporting performance higher than a hole transporting performance may be used for the electron transporting layer 8 in addition to the above substances. The electron transporting layer 8 may be provided in the form of a single layer or a laminate of two or more layers of the above substance(s).

Moreover, a high-molecule compound is also usable for the electron transporting layer 8. Examples of the high polymer compound include poly[(9,9-dihexylfluorene-2,7-diyl)-co-(pyridine-3,5-diyl)] (abbreviation: PF-Py) and poly [(9,9-dioctylfluorene-2,7-diyl)-co-(2,2'-bipyridine-6,6'-diyl)] (abbreviation: PF-BPy).

In the first exemplary embodiment, the electron transporting layer 8 preferably has a function to prevent triplet excitons generated in the emitting layer 5 from diffusing to the electron transporting layer 8 and the electron injecting layer 9 and trap the triplet excitons in the emitting layer 5.

Electron Injecting Layer

The electron injecting layer 9 is a layer containing a highly electron-injectable substance. For the electron injecting layer 9, an alkali metal, alkaline earth metal or a compound thereof are usable, examples of which include lithium (Li), cesium (Cs), calcium (Ca), lithium fluoride (LiF), cesium fluoride (CsF), calcium fluoride (CaF2), and lithium oxide (LiOx). In addition, the alkali metal, alkaline earth metal or the compound thereof may be added to the substance exhibiting the electron transportability in use. Specifically, for instance, magnesium (Mg) added to Alq may be used. In this case, the electrons can be more efficiently injected from the cathode 4.

Alternatively, a composite material provided by mixing an organic compound with an electron donor may be used for the electron injecting layer 9. The composite material exhibits excellent electron injecting performance and electron transporting performance since the electron donor generates electron in the organic compound. In this arrangement, the organic compound is preferably a material exhibiting an excellent transforming performance of the generated electrons. Specifically, for instance, the above-described substance for the electron transporting layer 8 (e.g., the metal complex and heteroaromatic compound) is usable. The electron donor may be any substance exhibiting an electron donating performance to the organic compound. Specifically, the electron donor is preferably alkali metal, alkaline earth metal and rare earth metal such as lithium, cesium, magnesium, calcium, erbium and ytterbium. The electron donor is also preferably alkali metal oxide and alkaline earth metal oxide such as lithium oxide, calcium oxide, and barium oxide. Further, Lewis base such as magnesium oxide is also usable. Furthermore, tetrathiafulvalene (abbreviation: TTF) is al so usable.

Cathode

It is preferable to use metal, an alloy, an electroconductive compound, and a mixture thereof, which have a small work function (specifically, 3.8 eV or less) for the cathode 4. Examples of such a material for the cathode include the elements belonging to the group 1 or 2 of the periodic table, specifically, an alkali metal such as lithium (Li) and cesium (Cs), an alkaline earth metal such as magnesium (Mg), calcium (Ca) and strontium (Sr), an alloy containing the alkali metal and the alkaline earth metal (e.g., MgAg, AlLi), a rare earth metal such as europium (Eu) and ytterbium (Yb), and an alloy containing the rare earth metal.

It should be noted that the vacuum deposition method and the sputtering method are usable for forming the cathode 4 using the alkali metal, alkaline earth metal and the alloy thereof. Further, when a silver paste is used for the cathode 4, the coating method and the inkjet method are usable.

By providing the electron injecting layer 9, various conductive materials such as Al, Ag, ITO, graphene, and indium oxide-tin oxide containing silicon or silicon oxide may be used for forming the cathode 4 regardless of the work function. The conductive materials can be formed into a film using the sputtering method, inkjet method, spin coating method and the like.

Layer Formation Method(s)

The method of forming the respective layers of the organic EL device 1 of the first exemplary embodiment is not limited except for those specifically mentioned above, where known methods including dry film formation and wet film formation methods are applicable. Examples of the dry film formation method include vacuum deposition method, sputtering method, plasma process, and ion-plating method. Examples of the wet film formation method include spin coating method, dipping method, flow coating method and inkjet method.

Film Thickness

The film thickness of each organic layer of the organic EL device 1 in the first exemplary embodiment is subject to no limitation except for the thickness particularly described above. However, the thickness is typically preferably in a range of several nanometers to 1 μm because an excessively thin film is likely to entail defects such as pin holes while an excessively thick film requires high applied voltage and deteriorates efficiency.

Herein, a "hydrogen atom" means isotopes having different neutron numbers and specifically encompasses protium, deuterium and tritium.

Herein, "carbon atoms forming a ring (ring carbon atoms)" mean carbon atoms forming a saturated ring, unsaturated ring, or aromatic ring.

Herein, the number of carbon atoms forming a ring (also referred to as ring carbon atoms) means the number of carbon atoms included in atoms forming the ring itself of a compound in which the atoms are bonded to form the ring (e.g., a monocyclic compound, a fused ring compound, a cross-linked compound, a carbocyclic compound, and a heterocyclic compound). When the ring is substituted by a substituent, the "ring carbon atoms" do not include carbon(s) contained in the substituent. Unless specifically described, the same applies to the "ring carbon atoms" described later. For instance, a benzene ring has 6 ring carbon atoms, a naphthalene ring has 10 ring carbon atoms, a pyridinyl group has 5 ring carbon atoms, and a furanyl group has 4 ring carbon atoms. When the benzene ring and/or the naphthalene ring is substituted by, for instance, an alkyl group, the number of carbon atoms of the alkyl group is not included in the number of the ring carbon atoms. When a fluorene ring is substituted by, for instance, a fluorene ring (e.g., a spirofluorene ring), the number of carbon atoms of the fluorene ring as a substituent is not counted in the number of the ring carbon atoms for the fluorene ring.

"Atoms forming a ring (ring atoms)" herein mean carbon atoms and hetero atoms forming a hetero ring including a saturated ring, unsaturated ring, or aromatic ring.

Herein, the number of atoms forming a ring (also referred to as ring atoms) means the number of atoms forming the ring itself of a compound in which the atoms are bonded to form the ring (e.g., a monocyclic compound, a fused ring compound, a cross-linked compound, a carbocyclic compound, and a heterocyclic compound). Atom(s) not forming the ring (e.g., a hydrogen atom for terminating the atoms forming the ring) and atoms included in a substituent substituting the ring are not counted in the number of the ring atoms. Unless specifically described, the same applies to the "ring atoms" described later. For instance, a pyridine ring has 6 ring atoms, a quinazoline ring has 10 ring atoms, and a furan ring has 5 ring atoms. Hydrogen atoms respectively bonded to the pyridine ring and the quinazoline ring and atoms forming the substituents are not counted in the number of the ring atoms. When a fluorene ring is substituted by, for instance, a fluorene ring (e.g., a spirofluorene ring), the number of atoms of the fluorene ring as a substituent is not included in the number of the ring atoms for the fluorene ring.

Next, each of the substituents represented by the above formulae will be described below.

Examples of the aryl group (aromatic hydrocarbon group) having 6 to 30 ring carbon atoms in the first exemplary embodiment are a phenyl group, biphenyl group, terphenyl group, naphthyl group, anthryl group, phenanthryl group, fluorenyl group, pyrenyl group, chrysenyl group, fluoranthenyl group, benz[a]anthryl group, benzo[c]phenanthryl group, triphenylenyl group, benzo[k]fluoranthenyl group, benzo[g]chrysenyl group, benzo[b]triphenylenyl group, picenyl group, and perylenyl group.

The aryl group herein preferably has 6 to 20 ring carbon atoms, more preferably 6 to 14 ring carbon atoms, further preferably 6 to 12 ring carbon atoms. Among the aryl group, a phenyl group, biphenyl group, naphthyl group, phenanthryl group, terphenyl group and fluorenyl group are particularly preferable. In a 1-fluorenyl group, 2-fluorenyl group, 3-fluorenyl group and 4-fluorenyl group, a carbon atom at a position 9 is preferably substituted by the substituted or unsubstituted alkyl group having 1 to 30 carbon atoms or an unsubstituted aryl group having 6 to 18 ring carbon atoms described herein.

The heteroaryl group (occasionally, referred to as heterocyclic group, heteroaromatic ring group or aromatic heterocyclic group) having 5 to 30 ring atoms preferably contains at least one atom selected from the group consisting of nitrogen, sulfur, oxygen, silicon, selenium atom and germanium atom, and more preferably contains at least one atom selected from the group consisting of nitrogen, sulfur and oxygen.

Examples of the heteroaryl group (heterocyclic group) having 5 to 30 ring atoms in the first exemplary embodiment include a pyridyl group, pyrimidinyl group, pyrazinyl group, pyridazynyl group, triazinyl group, quinolyl group, isoquinolinyl group, naphthyridinyl group, phthalazinyl group, quinoxalinyl group, quinazolinyl group, phenanthridinyl group, acridinyl group, phenanthrolinyl group, pyrrolyl group, imidazolyl group, pyrazolyl group, triazolyl group, tetrazolyl group, indolyl group, benzimidazolyl group, indazolyl group, imidazopyridinyl group, benzotriazolyl group, carbazolyl group, furyl group, thienyl group, oxazolyl group, thiazolyl group, isoxazolyl group, isothiazolyl group, oxadiazolyl group, thiadiazolyl group, benzofuranyl group, benzothiophenyl group, benzoxazolyl group, benzothiazolyl group, benzisoxazolyl group, benzisothiazolyl group, benzoxadiazolyl group, benzothiadiazolyl group, dibenzofuranyl group, dibenzothiophenyl group, piperidinyl group, pyrrolidinyl group, piperazinyl group, morpholyl group, phenazinyl group, phenothiazinyl group, and phenoxazinyl group.

The heteroaryl group herein preferably has 5 to 20 ring atoms, more preferably 5 to 14 ring atoms. Among the above, a 1-dibenzofuranyl group, 2-dibenzofuranyl group, 3-dibenzofuranyl group, 4-dibenzofuranyl group, 1-dibenzothiophenyl group, 2-dibenzothiophenyl group, 3-dibenzothiophenyl group, 4-dibenzothiophenyl group, 1-carbazolyl group, 2-carbazolyl group, 3-carbazolyl group, 4-carbazolyl group, and 9-carbazolyl group are particularly preferable. In 1-carbazolyl group, 2-carbazolyl group, 3-carbazolyl group and 4-carbazolyl group, a nitrogen atom at the ninth position is preferably substituted by a substituted or unsubstituted aryl group having 6 to 30 ring carbon atoms or a substituted or unsubstituted heterocyclic group having 5 to 30 ring atoms as defined herein.

Further, the heterocyclic group herein may be a group derived from moieties represented by formulae (XY-1) to (XY-18).

[Formula 62]

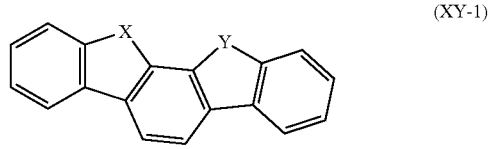

(XY-1)

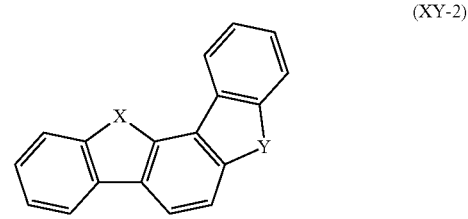

(XY-2)

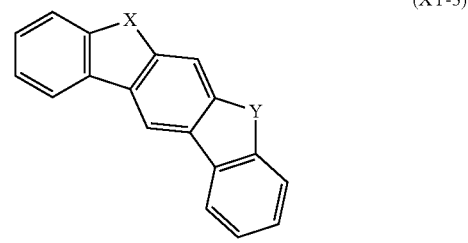

(XY-3)

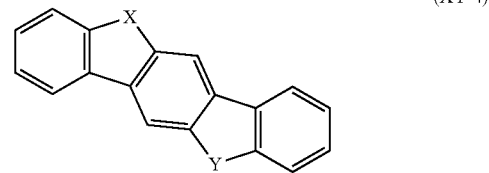

(XY-4)

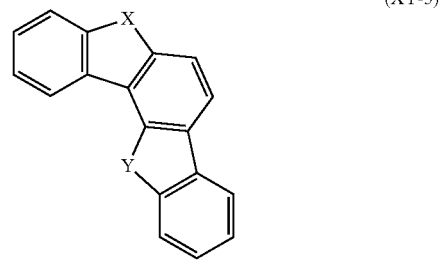

(XY-5)

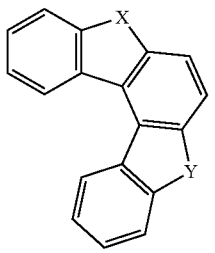  (XY-6)

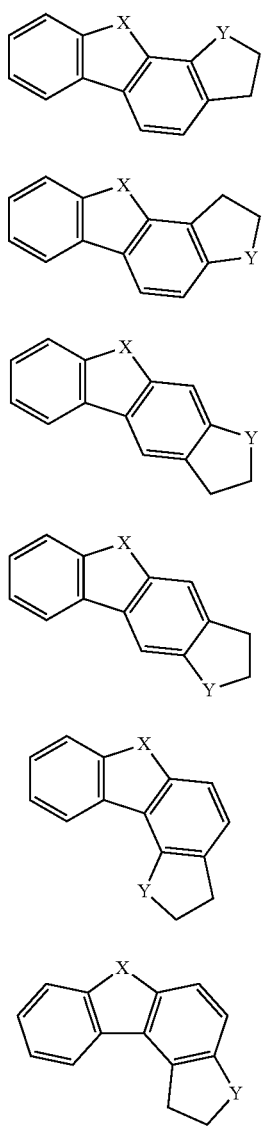

(XY-7)

(XY-8)

(XY-9)

(XY-10)

(XY-11)

(XY-12)

[Formula 64]

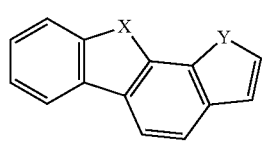 (XY-13)

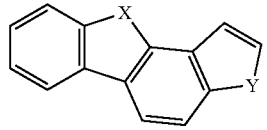 (XY-14)

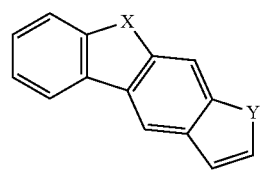 (XY-15)

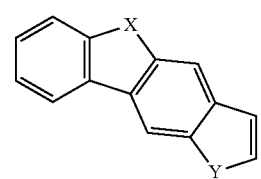 (XY-16)

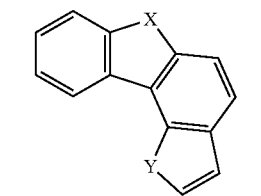 (XY-17)

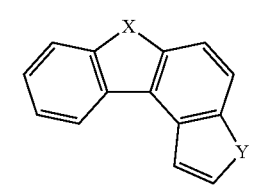 (XY-18)

In the formulae (XY-1) to (XY-18), X and Y each independently preferably are a hetero atom, and preferably are a nitrogen atom, an oxygen atom, sulfur atom, selenium atom, silicon atom or germanium atom. The partial structures represented by the formulae (XY-1) to (XY-18) may have a bond at any position to be a heterocyclic group, which may be substituted.

Herein, for instance, a substituted or unsubstituted carbazolyl group may include a group in which a ring is further fused to a carbazole ring represented by a formula below. Such a group may be substituted. The position of the bond may be altered as needed.

[Formula 65]

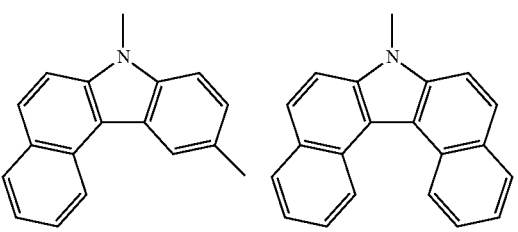

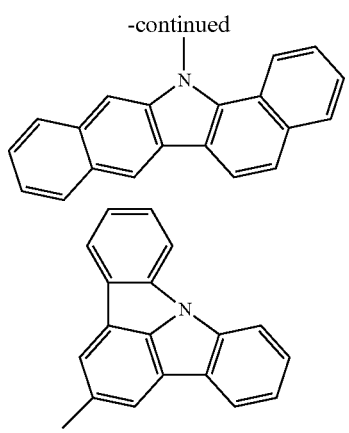

The alkyl group having 1 to 30 carbon atoms herein may be linear, branched or cyclic. Examples of the linear or branched alkyl group are a methyl group, ethyl group, propyl group, isopropyl group, n-butyl group, s-butyl group, isobutyl group, t-butyl group, n-pentyl group, n-hexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, neopentyl group, amyl group, isoamyl group, 1-methylpentyl group, 2-methylpentyl group, 1-pentylhexyl group, 1-butylpentyl group, 1-heptyloctyl group and 3-methylpentyl group.

The linear or branched alkyl group herein preferably has 1 to 10 carbon atoms, more preferably 1 to 6 carbon atoms. Among the linear or branched alkyl group, a methyl group, ethyl group, propyl group, isopropyl group, n-butyl group, s-butyl group, isobutyl group, t-butyl group, n-pentyl group, n-hexyl group, amyl group, isoamyl group and neopentyl group are particularly preferable.

Examples of the cycloalkyl group having 3 to 30 carbon atoms herein are a cyclopropyl group, cyclobutyl group, cyclopentyl group, cyclohexyl group, 4-metylcyclohexyl group, adamantyl group and norbornyl group. The cycloalkyl group preferably has 3 to 10 ring carbon atoms, more preferably 5 to 8 ring carbon atoms. Among the cycloalkyl group, a cyclopentyl group and a cyclohexyl group are particularly preferable.

A halogenated alkyl group having 1 to 30 carbon atoms herein is exemplified by one provided by substituting an alkyl group having 1 to 30 carbon atoms with one or more halogen atoms. Specific examples of the halogenated alkyl group includes a fluoromethyl group, difluoromethyl group, trifluoromethyl group, fluoroethyl group, trifluoromethylmethyl group, trifluoroethyl group, and pentafluoroethyl group.

A substituted or unsubstituted aralkyl group having 7 to 30 carbon atoms is represented as —$Z_3$—$Z_4$. $Z_3$ is exemplified by an alkylene group derived from the above alkyl group having 1 to 30 carbon atoms. $Z_4$ is exemplified by the above aryl group having 6 to 30 ring carbon atoms. In the aralkyl having 7 to 30 carbon atoms, the aryl moiety represented by $Z_4$ preferably has 6 to 20 ring carbon atoms, more preferably 6 to 12 ring carbon atoms. The alkyl moiety of $Z_3$ preferably has 1 to 20 carbon atoms, more preferably 1 to 10 carbon atoms, further more preferably 1 to 6 carbon atoms. Examples of the aralkyl group are a benzyl group, 2-phenylpropane-2-yl group, 1-phenylethyl group, 2-phenylethyl group, 1-phenylisopropyl group, 2-phenylisopropyl group, phenyl-t-butyl group, α-naphthylmethyl group, 1-α- naphthylethyl group, 2-α-naphthyl ethyl group, 1-α-naphthylisopropyl group, 2-α-naphthylisopropyl group, β-naphthylmethyl group, 1-β-naphthylethyl group, 2-β-naphthylethyl group, 1-β-naphthylisopropyl group, and 2-β-naphthylisopropyl group.

The substituted phosphoryl group is represented by a formula (P).

[Formula 66]

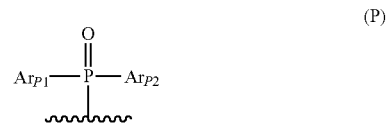

(P)

In the above formula (P), $Ar_{P1}$ and $Ar_{P2}$ are preferably each independently a substituent selected from the group consisting of an alkyl group having 1 to 30 carbon atoms and an aryl group having 6 to 30 ring carbon atoms, more preferably a substituent selected from the group consisting of an alkyl group having 1 to 10 carbon atoms and an aryl group having 6 to 20 ring carbon atoms, further preferably a substituent selected from the group consisting of an alkyl group having 1 to 6 carbon atoms and an aryl group having 6 to 14 ring carbon atoms.

Examples of the substituted silyl group are an alkylsilyl group having 3 to 30 carbon atoms and arylsilyl group having 6 to 30 ring carbon atoms.

The alkylsilyl group having 3 to 30 carbon atoms herein is exemplified by a trialkylsilyl group having the above examples of the alkyl group having 1 to 30 carbon atoms. Specific examples of the alkyl silyl group are a trimethylsilyl group, triethylsilyl group, tri-n-butylsilyl group, tri-n-octylsilyl group, triisobutylsilyl group, dimethylethylsilyl group, dimethylisopropylsilyl group, dimethyl-n-propylsilyl group, dimethyl-n-butylsilyl group, dimethyl-t-butylsilyl group, diethylisopropylsilyl group, vinyl dimethylsilyl group, propyldimethylsilyl group, and triisopropylsilyl group. Three alkyl groups in the trialkylsilyl group may be mutually the same or different.

Examples of the arylsilyl group having 6 to 30 ring carbon atoms herein are a dialkylarylsilyl group, alkyldiarylsilyl group and triarylsilyl group.

The dialkylarylsilyl group is exemplified by a dialkylarylsilyl group having two of the examples of the alkyl group having 1 to 30 carbon atoms and one of the aryl group having 6 to 30 ring carbon atoms. The dialkylarylsilyl group preferably has 8 to 30 carbon atoms.

The alkyldiarylsilyl group is exemplified by an alkyldiarylsilyl group having one of the examples of the alkyl group having 1 to 30 carbon atoms and two of the aryl group having 6 to 30 ring carbon atoms. The dialkylarylsilyl group preferably has 13 to 30 carbon atoms.

The triarylsilyl group is exemplified by a triarylsilyl group having three of the aryl group having 6 to 30 ring carbon atoms. The triarylsilyl group preferably has 18 to 30 carbon atoms.

Examples of the halogen atom are a fluorine atom, a chlorine atom, a bromine atom and an iodine atom, among which a fluorine atom is preferable.

"Unsubstituted" in "substituted or unsubstituted" herein means that a group is not substituted by the above-described substituents but bonded to a hydrogen atom.

Herein, "XX to YY carbon atoms" in the description of "substituted or unsubstituted ZZ group having XX to YY carbon atoms" represent carbon atoms of an unsubstituted ZZ group and do not include carbon atoms of a substituent(s) of the substituted ZZ group. Herein, "YY" is larger than "XX." "XX" and "YY" each mean an integer of 1 or more.

Herein, "XX to YY atoms" in the description of "substituted or unsubstituted ZZ group having XX to YY atoms" represent atoms of an unsubstituted ZZ group and does not include atoms of a substituent(s) of the substituted ZZ group. Herein, "YY" is larger than "XX." "XX" and "YY" each mean an integer of 1 or more.

Examples of the substituent meant by "substituted or unsubstituted" herein include substituted amino group, alkoxy group, aryloxy group, alkenyl group, alkynyl group, alkylthio group, arylthio group and hydroxyl group in addition to the above-described aryl group, heteroaryl group, alkyl group (linear or branched alkyl group, cycloalkyl group and haloalkyl group), aralkyl group, substituted phosphoryl group, substituted silyl group, cyano group, nitro group, carboxy group and halogen atom.

In the above-described substituents meant by "substituted or unsubstituted", the aryl group, heteroaryl group, alkyl group, halogen atom, alkylsilyl group, arylsilyl group and cyano group are preferable. The preferable ones of the specific examples of each substituent are further preferable.

The substituents meant by "substituted or unsubstituted" may further be substituted by at least one group selected from the group consisting of the above-described aryl group, heteroaryl group, alkyl group (linear or branched alkyl group, cycloalkyl group and haloalkyl group), substituted phosphoryl group, alkylsilyl group, arylsilyl group, alkoxy group, aryloxy group, alkyl amino group, aryl amino group, alkylthio group, arylthio group, alkenyl group, alkynyl group, aralkyl group, halogen atom, cyano group, hydroxyl group, nitro group and carboxy group. In addition, plural ones of these substituents may be mutually bonded to form a ring.

Examples of the substituted amino group are an alkylamino group having 2 to 30 carbon atoms and arylamino group having 6 to 60 ring carbon atoms.

The alkylamino group having 2 to 30 carbon atoms is represented by —$NHR_V$ or —$N(R_V)_2$. $R_V$ is exemplified by the alkyl group having 1 to 30 carbon atoms.

The arylamino group having 6 to 60 ring carbon atoms is represented by —$NHR_W$ or —$N(R_W)_2$. $R_W$ is exemplified by the above aryl group having 6 to 30 ring carbon atoms.

The alkoxy group having 1 to 30 carbon atoms is represented by —$OZ_1$. $Z_1$ is exemplified by the above alkyl group having 1 to 30 carbon atoms. Examples of the alkoxy group are a methoxy group, ethoxy group, propoxy group, butoxy group, pentyloxy group and hexyloxy group. The alkoxy group preferably has 1 to 20 carbon atoms.

A halogenated alkoxy group provided by substituting the alkoxy group with a halogen atom is exemplified by a halogenated alkoxy group provided by substituting the alkoxy group having 1 to 30 carbon atoms with one or more fluorine groups.

The aryloxy group having 6 to 30 ring carbon atoms is represented by —$OZ_2$. $Z_2$ is exemplified by the above aryl group having 6 to 30 ring carbon atoms. The aryloxy group preferably has 6 to 20 ring carbon atoms. The aryloxy group is exemplified by a phenoxy group.

The alkenyl group preferably has 2 to 30 carbon atoms and may be linear, branched or cyclic. Examples of the alkenyl group include a vinyl group, propenyl group, butenyl group, oleyl group, eicosapentaenyl group, docosahexaenyl group, styryl group, 2,2-diphenylvinyl group, 1,2,2-triphenylvinyl group, 2-phenyl-2-propenyl group, cyclopentadienyl group, cyclopentenyl group, cyclohexenyl group and cyclohexadienyl group.

The alkynyl group preferably has 2 to 30 carbon atoms and may be linear, branched or cyclic. Examples of the alkynyl group are ethynyl, propynyl and 2-phenylethynyl.

The alkylthio group having 1 to 30 carbon atoms is represented by —$SR_V$. $R_V$ is exemplified by the alkyl group having 1 to 30 carbon atoms. The alkylthio group preferably has 1 to 20 carbon atoms.

The arylthio group having 6 to 30 ring carbon atoms is represented by —$SR_W$. $R_W$ is exemplified by the above aryl group having 6 to 30 ring carbon atoms. The arylthio group preferably has 6 to 20 ring carbon atoms.

Herein, when the substituents are bonded to each other to form a ring structure, the ring structure is in a form of a saturated ring, an unsaturated ring, an aromatic hydrocarbon ring or a hetero ring. In addition, the ring structure formed by the bonded plural ones of these substituents may have a substituent.

Herein, examples of the aromatic hydrocarbon ring and the heterocyclic ring include a cyclic structure from which the above monovalent group is derived.

Electronic Device

The organic EL device 1 according to the first exemplary embodiments is usable in an electronic device such as a display unit and a light-emitting unit. Examples of the display unit include display components such as en organic EL panel module, TV, mobile phone, tablet, and personal computer. Examples of the light-emitting unit include an illuminator and a vehicle light.

Second Exemplary Embodiment

An arrangement of an organic EL device according to a second exemplary embodiment will be described. In the description of the second exemplary embodiment, the same components as those in the first exemplary embodiment are denoted by the same reference signs and names to simplify or omit an explanation of the components. In the second exemplary embodiment, the same materials and compounds as described in the first exemplary embodiment are usable unless particularly described.

The organic EL device according to the second exemplary embodiment differs from the organic EL device according to the first exemplary embodiment in that the emitting layer further comprises a third compound. The organic EL device according to the second exemplary embodiment is the same as the organic EL device according to the first exemplary embodiment except for the above.

Third Compound

The third compound has a singlet energy larger than a singlet energy of the first compound.

According to the organic EL device according to the second exemplary embodiment, a highly efficient organic EL device can be provided.

The organic EL device according to the second exemplary embodiment comprises an emitting layer containing a delayed-fluorescent first compound, a fluorescent second compound, and a third compound having a singlet energy larger than that of the first compound, so that emission efficiency is improved. The reason for the improvement in the emission efficiency is believed to be attributable to an improvement in a carrier balance in the emitting layer due to the presence of the third compound.

Figure 5:
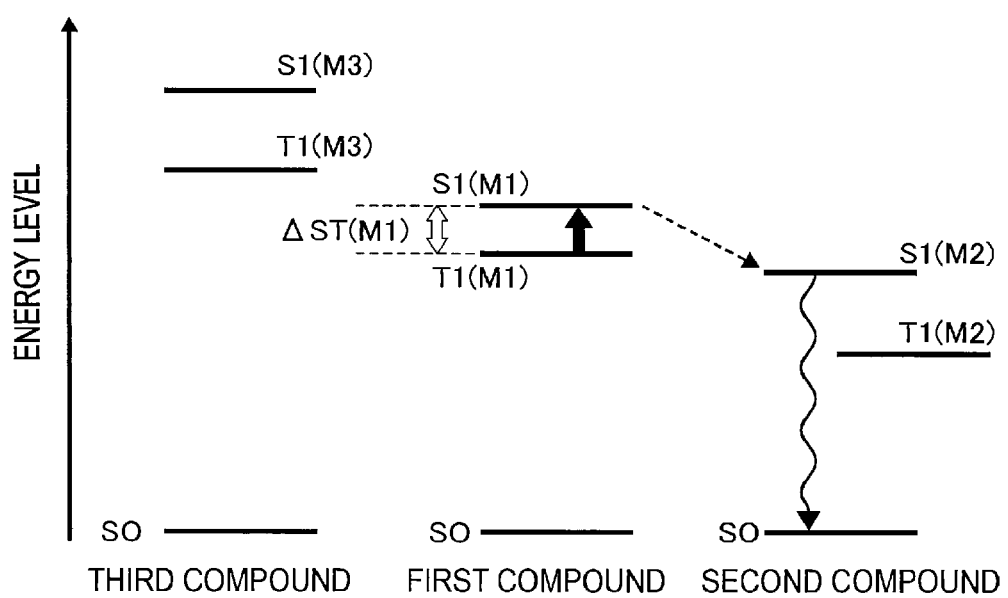
FIG. 5 shows a relationship between an energy level and an energy transfer of compounds contained in an emitting layer in a second exemplary embodiment.

FIG. 5 shows an example of a relationship between energy levels of the first, second and third compounds in the emitting layer. In FIG. 5, S0 represents a ground state, S1(M1) represents a lowest singlet state of the first compound, T1(M1) represents a lowest triplet state of the first compound, S1(M2) represents a lowest singlet state of the second compound, T1(M2) represents a lowest triplet state of the second compound, S1(M3) represents a lowest singlet state of the third compound, and T1(M3) represents a lowest triplet state of the third compound. A dashed arrow directed from S1(M1) to S1(M12 in FIG. 5 represents Förster energy transfer from the lowest singlet state of the first compound to the lowest singlet state of the second compound.

As shown in FIG. 5, when a compound having a small $\Delta ST(M1)$ is used as the first compound, inverse intersystem crossing from the lowest triplet state T1(M1) to the lowest singlet state S1(M1) can be caused by a heat energy. Consequently, Förster energy transfer from the lowest singlet state S1(M1) of the first compound to the lowest singlet state S1(M2) of the second compound is caused. As a result, fluorescence from the lowest singlet state S1(M2) of the second compound can be observed. It is speculated that the internal quantum efficiency can be theoretically raised up to 100% also by using the delayed fluorescence by the TADF mechanism.

Ratio of Three Components In the emitting layer of the organic EL device of the second exemplary embodiment, it is preferable that the content ratio of the first compound is in a range from 10 mass % to 80 mass %, the content ratio of the second compound is in a range from 1 mass % to 10 mass %, and the content ratio of the third compound is in a range from 10 mass % to 80 mass %. A content ratio of the first compound is more preferably in a range from 20 mass % to 80 mass %, further preferably in a range from 20 mass % to 60 mass %. An upper limit of a total content ratio of the first compound, second compound and third compound in the emitting layer is 100 mass %. It should be noted that the second exemplary embodiment does not exclude an arrangement in which a material other than the first compound, second compound and third compound is contained in the emitting layer.

Although the third compound is not particularly limited, the third compound is preferably a compound other than an amine compound. Further, the third compound may be a derivative selected from the group consisting of a carbazole derivative, dibenzofuran derivative, and dibenzothiophene derivative. It should be noted that the third compound in the second exemplary embodiments is not limited thereto.

It is also preferable that the third compound has at least one of a moiety represented by a formula (31) and a moiety represented by a formula (32) in one molecule.

[Formula 67]

(31)

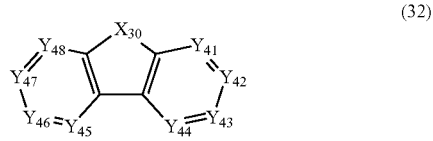

(32)

In the above formula (31), $Y_{31}$ to $Y_{36}$ are each independently a nitrogen atom, or a carbon atom bonded to other atom in the molecule of the third compound, with a proviso that at least one of $Y_{31}$ to $Y_{36}$ is the carbon atom bonded to the other atom of the molecule of the third compound. In the above formula (32), $Y_{41}$ to $Y_{48}$ are each independently a nitrogen atom, or a carbon atom bonded to other atom in the molecule of the third compound, with a proviso that at least one of $Y_{41}$ to $Y_{48}$ is the carbon atom bonded to the other atom of the molecule of the third compound, and $X_{30}$ is a nitrogen atom, an oxygen atom or a sulfur atom.

In the formula (32), it is also preferable that at least two of $Y_{41}$ to $Y_{48}$ are carbon atoms bonded to other atom(s) in the molecule of the third compound and a ring structure including the carbon atoms is formed.

For instance, the moiety represented by the formula (32) is preferably any one selected from the group consisting of moieties represented by formulae (321), (322), (323), (324), (325) and (326).

[Formula 68]

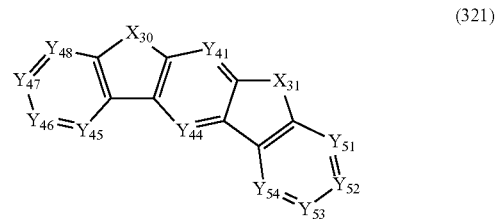

[Formula 69]

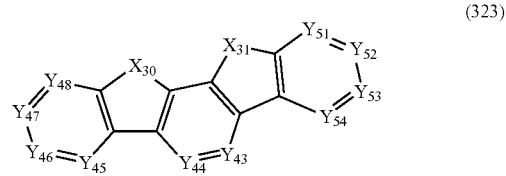

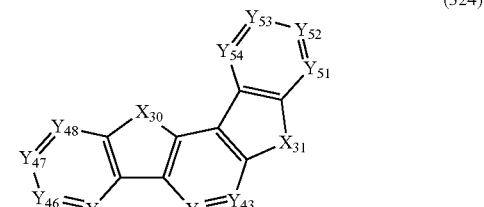

[Formula 70]

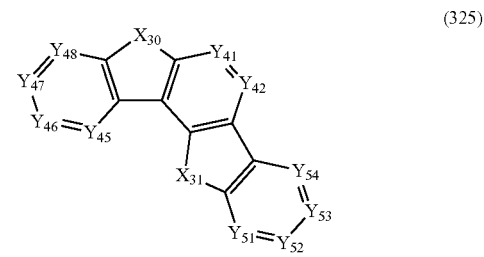

(326)

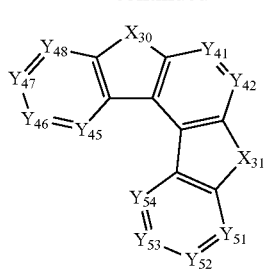

In the above formulae (321) to (326), $X_{30}$ is a nitrogen atom, an oxygen atom or a sulfur atom, and $Y_{41}$ to $Y_{48}$ are each independently a nitrogen atom, or a carbon atom bonded to other atom in the molecule of the third compound, $X_{31}$ is a nitrogen atom, an oxygen atom, a sulfur atom or a carbon atom, and $Y_{51}$ to $Y_{54}$ each independently are a nitrogen atom or a carbon atom bonded to another atom in the molecule of the third compound.

In the second exemplary embodiments, the third compound preferably has the moiety represented by the formula (323) among those represented by the formulae (321) to (326).

The moiety represented by the formula (31) is preferably included in the third compound in a form of at least one group selected from the group consisting of a group represented by a formula (33) and a group represented by a formula (34).

As for the third compound, bonding positions are preferably both situated in meta positions as shown in the formulae (33) and (34) to keep an energy gap $T_{77K}(M3)$ at 77 [K] high.

[Formula 71]

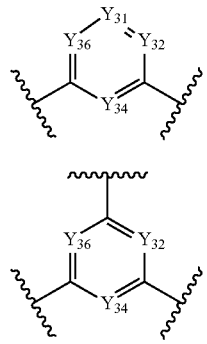

(33)

(34)

In the formulae (33) and (34), $Y_{31}$, $Y_{32}$, $Y_{34}$ and $Y_{36}$ are each independently a nitrogen atom or $CR_{31}$, $R_{31}$ is a hydrogen atom or a substituent, and $R_{31}$ as a substituent is a group selected from the group consisting of a substituted or unsubstituted aromatic hydrocarbon group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 carbon atoms, a substituted or unsubstituted aralkyl group having 7 to 30 carbon atoms, a substituted silyl group, a substituted germanium group, a substituted phosphine oxide group, a halogen atom, a cyano group, a nitro group, and a carboxy group. A substituted or unsubstituted aromatic hydrocarbon group having 6 to 30 ring carbon atoms in $R_{31}$ is preferably a non-fused ring.

Wavy lines in the formulae (33) and (34) each show a bonding position with another atom or another structure in the molecule of the third compound.

In the formula (33), $Y_{31}$, $Y_{32}$, $Y_{34}$ and $Y_{36}$ are preferably each independently $CR_{31}$, in which a plurality of $R_{31}$s may be the same or different.

Further, in the formula (34), $Y_{32}$, $Y_{34}$ and $Y_{36}$ are preferably each independently $CR_{31}$, in which a plurality of $R_{31}$s may be the same or different.

The substituted germanium group is preferably represented by —Ge($R_{101}$)$_3$. $R_{101}$ is each independently a substituent. The substituent $R_{101}$ is preferably a substituted or unsubstituted alkyl group having 1 to 30 carbon atoms or a substituted or unsubstituted aromatic hydrocarbon group having 6 to 30 ring carbon atoms. A plurality of $R_{101}$s are mutually the same or different.

The moiety represented by the formula (32) is preferably included in the third compound as at least one group selected from the group consisting of a group represented by a formula (3), a group represented by a formula (36), a group represented by a formula (37), a group represented by a formula (38), a group represented by a formula (39), and a group represented by a formula (30a).

[Formula 72]

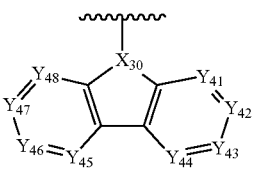

(35)

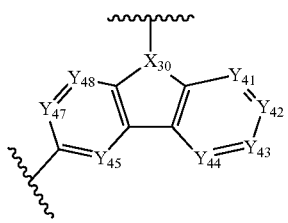

(36)

[Formula 73]

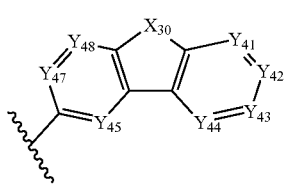

(37)

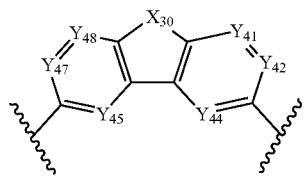

(38)

-continued

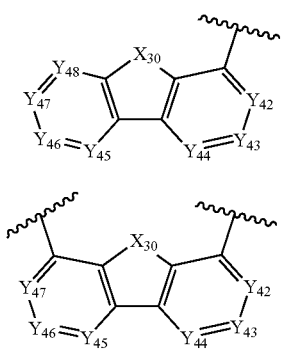

(39)

(30a)

In the above formulae (35) to (39) and (30a), it is preferable that $Y_{41}$, $Y_{42}$, $Y_{43}$, $Y_{44}$, $Y_{45}$, $Y_{46}$, $Y_{47}$ and $Y_{48}$ are each independently a nitrogen atom or $CR_{32}$, $R_{32}$ being a hydrogen atom or a substituent, $R_{32}$ as a substituent being a group selected from the group consisting of a substituted or unsubstituted aromatic hydrocarbon group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted silyl group, a substituted germanium group, a substituted phosphine oxide group, a halogen atom, a cyano group, a nitro group, and a carboxy group, with a proviso that the substituted or unsubstituted aromatic hydrocarbon group having 6 to 30 ring carbon atoms in $R_{32}$ is a non-fused ring. In the above formulae (35) and (36), it is preferable that $X_{30}$ is a nitrogen atom. In the above formulae (37) to (39) and (30a), it is preferable that $X_{30}$ is $NR_{33}$, an oxygen atom or a sulfur atom, $R_{33}$ being a substituent selected from the group consisting of a substituted or unsubstituted aromatic hydrocarbon group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted silyl group, a substituted germanium group, a substituted phosphine oxide group, a fluorine atom, a cyano group, a nitro group, and a carboxy group, with a proviso that that the substituted or unsubstituted aromatic hydrocarbon group having 6 to 30 ring carbon atoms in $R_{33}$ is a non-fused ring.

Wavy lines in the formulae (35) to (39) and (30a) each show a bonding position with another atom or another structure in the molecule of the third compound.

In the formula (35), $Y_{41}$ to $Y_{48}$ are each independently preferably $CR_{32}$. In the formulae (36) and (37), $Y_{41}$ to $Y_{45}$, $Y_{47}$ and $Y_{48}$ are each independently preferably $CR_{32}$. In the formula (38), $Y_{41}$, $Y_{42}$, $Y_{44}$, $Y_{45}$, $Y_{47}$ and $Y_{48}$ are each independently preferably $CR_{32}$. In the formula (39), $Y_{42}$ to $Y_{48}$ are each independently preferably $CR_{32}$. In the formula (30a), $Y_{42}$ to $Y_{47}$ are each independently preferably $CR_{32}$. A plurality of $R_{32}$s may be the same or different.

In the third compound, $X_{30}$ is preferably an oxygen atom or a sulfur atom, more preferably an oxygen atom.

In the third compound, $R_{31}$ and $R_{32}$ are each independently a hydrogen atom or a substituent. The substituent in $R_{31}$ and $R_{32}$ are preferably selected from the group consisting of a fluorine atom, a cyano group, a substituted or unsubstituted alkyl group having 1 to 30 carbon atoms, a substituted or unsubstituted aromatic hydrocarbon group having 6 to 30 ring carbon atoms, and a substituted or unsubstituted heterocyclic group having 5 to 30 ring atoms. $R_{31}$ and $R_{32}$ are more preferably a hydrogen atom, a cyano group, a substituted or unsubstituted aromatic hydrocarbon group having 6 to 30 ring carbon atoms, or a substituted or unsubstituted heterocyclic group having 5 to 30 ring atoms. The substituted or unsubstituted aromatic hydrocarbon group having 6 to 30 ring carbon atoms in $R_{31}$ and $R_{32}$ is preferably a non-fused ring.

It is also preferable that the third compound is an aromatic hydrocarbon compound or an aromatic heterocyclic compound. Moreover, it is preferable that the third compound does not have a fused aromatic hydrocarbon ring in the molecule.

Manufacturing Method of Third Compound

The third compound can be manufactured by methods disclosed in International Publication No. WO2012/153780, International Publication No. WO2013/038650, and the like.

Examples of the substituent in the third compound are shown below, but the invention is not limited thereto.

Specific examples of the aromatic hydrocarbon group (occasionally referred to as an aryl group) include a phenyl group, tolyl group, xylyl group, naphthyl group, phenanthryl group, pyrenyl group, chrysenyl group, benzo[c]phenanthryl group, benzo[g]chrysenyl group, benzoanthryl group, triphenylenyl group, fluorenyl group, 9,9-dimethylfluorenyl group, benzofluorenyl group, dibenzofluorenyl group, biphenyl group, terphenyl group, quarterphenyl group and fluoranthenyl group, among which a phenyl group, biphenyl group, terphenyl group, quarterphenyl group, naphthyl group, triphenylenyl group and fluorenyl group may be preferable.

Specific examples of the aromatic hydrocarbon group having a substituent include a tolyl group, xylyl group and 9,9-dimethylfluorenyl group.

As is understood from the specific examples, the aryl group includes both fused aryl group and non-fused aryl group.

Preferable examples of the aromatic hydrocarbon group include a phenyl group, biphenyl group, terphenyl group, quarterphenyl group, naphthyl group, triphenylenyl group and fluorenyl group.

Specific examples of the aromatic heterocyclic group (occasionally referred to as a heteroaryl group, heteroaromatic ring group or heterocyclic group) include a pyrrolyl group, pyrazolyl group, pyrazinyl group, pyrimidinyl group, pyridazynyl group, pyridyl group, triazinyl group, indolyl group, isoindolyl group, imidazolyl group, benzimidazolyl group, indazolyl group, imidazo[1,2-a]pyridinyl group, furyl group, benzofuranyl group, isobenzofuranyl group, dibenzofuranyl group, azadibenzofuranyl group, thiophenyl group, benzothiophenyl group, dibenzothiophenyl group, azadibenzothiophenyl group, quinolyl group, isoquinolyl group, quinoxalinyl group, quinazolinyl group, naphthyridinyl group, carbazolyl group, azacarbazolyl group, phenanthridinyl group, acridinyl group, phenanthrolinyl group, phenazinyl group, phenothiazinyl group, phenoxazinyl group, oxazolyl group, oxadiazolyl group, furazanyl group, benzoxazolyl group, thienyl group, thiazolyl group, thiadiazolyl group, benzothiazolyl group, triazolyl group and tetrazol yl group, among which a dibenzofuranyl group, dibenzothiophenyl group, carbazolyl group, pyridyl group, pyrimidinyl group, triazinyl group, azadibenzofuranyl group and azadibenzothiophenyl group may be preferable.

The aromatic heterocyclic group is preferably a dibenzofuranyl group, dibenzothiophenyl group, carbazolyl group, pyridyl group, pyrimidinyl group, triazinyl group, azadibenzofuranyl group or azadibenzothiophenyl group, and further preferably a dibenzofuranyl group, dibenzothiophenyl group, azadibenzofuranyl group or azadibenzothiophenyl group.

In the third compound, it is also preferable that the substituted silyl group is a substituted or unsubstituted trialkylsilyl group, a substituted or unsubstituted arylalkylsilyl group, or a substituted or unsubstituted triarylsilyl group.

Specific examples of the substituted or unsubstituted trialkylsilyl group include trimethylsilyl group and trimethylsilyl group.

Specific examples of the substituted or unsubstituted arylalkylsilyl group include diphenylmethylsilyl group, ditolylmethylsilyl group, and phenyl dimethylsilyl group.

Specific examples of the substituted or unsubstituted triarylsilyl group include triphenlsilyl group and tritolylsilyl group.

In the third compound, it is also preferable that the substituted phosphine oxide group is a substituted or unsubstituted diaryl phosphine oxide group.

Specific examples of the substituted or unsubstituted diaryl phosphine oxide group include a diphenyl phosphine oxide group and ditolyl phosphine oxide group.

Modification of Embodiments

It should be noted that the invention is not limited to the first exemplary embodiment. The invention may include any modification and improvement compatible with the invention.

For instance, the emitting layer is not limited to a single layer, but may be provided by laminating a plurality of emitting layers. When the organic EL device has a plurality of emitting layers, it is only required that at least one of the emitting layers contains the first compound and the second compound. For instance, the rest of the emitting layers may be a fluorescent emitting layer or a phosphorescent emitting layer with use of emission caused by electron transfer from the triplet excited state directly to the ground state.

When the organic EL device includes the plurality of emitting layers, the plurality of emitting layers may be adjacent to each other, or provide a so-called tandem-type organic EL device in which a plurality of emitting units are layered through an intermediate layer.

For instance, a blocking layer may be provided adjacent to the emitting layer closer to the anode and/or closer to the cathode. The blocking layer preferably abuts on the emitting layer and blocks at least one of holes, electrons and excitons.

For instance, when the blocking layer is provided abutting on the side of the emitting layer closer to the cathode, the blocking layer transports the electrons and blocks the holes from reaching a layer (e.g., the electron transporting layer) closer to the cathode beyond the blocking layer. When the organic EL device includes the electron transporting layer, the organic EL device preferably includes the blocking layer between the emitting layer and the electron transporting layer.

When the blocking layer is provided abutting on the side of the emitting layer closer to the anode, the blocking layer transports the holes and blocks the electrons from reaching a layer (e.g., the hole transporting layer) closer to the anode beyond the blocking layer. When the organic EL device includes the hole transporting layer, the organic EL device preferably includes the blocking layer between the emitting layer and the hole transporting layer.

Moreover, the blocking layer may abut on the emitting layer so that excited energy does not leak out from the emitting layer toward neighboring layer(s). Accordingly, the blocking layer blocks excitons generated in the emitting layer from transferring to a layer(s) (e.g., the electron transporting layer and the hole transporting layer) closer to the electrode(s) beyond the blocking layer.

The emitting layer and the blocking layer preferably abut on each other.

Further, specific arrangements and configurations for practicing the invention may be altered to other arrangements and configurations compatible with the invention.

EXAMPLE(S)

Examples of the invention will be described below. However, the invention is not limited to Examples.

Synthesis of Compound(s)

<Synthesis Example 1> Synthesis of Compound TADF-1

(1) Synthesis of Intermediate A

[Formula 75]

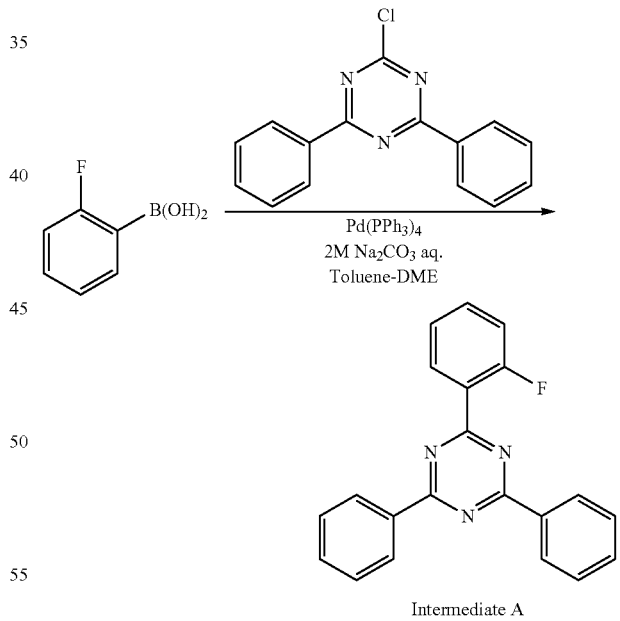

Intermediate A

To a three-necked flask, 7.0 g of 2-fluorophenyl boronic acid (50 mmmol), 13.4 g of 2-chloro-4,6-diphenyltriazine (50 mmol), 62.5 mL of 2M aqueous solution of sodium carbonate, 100 mL of 1,2-dimethoxyethane (DME) and 100 mL of toluene were added, and, after further adding 1.73 of tetrakis(triphenylphosphine)palladium (1.5 mmol), the mixture solution was stirred for 8 hours under an argon was atmosphere while being heated and refluxed. After the stirring while being heated and refluxed, an organic layer as separated. The separated organic layer was condensed under a reduced pressure, and the obtained residue was purified by using a silica-gel column chromatography. Toluene was used as a development solvent. After purification, the obtained solid was suspended and washed in methanol to obtain an intermediate A in a form of a white solid. A yield of the intermediate A was 11.6 g and yield rate of the intermediate A was 71%.

(2) Synthesis of Compound TADF-1

[Formula 76]

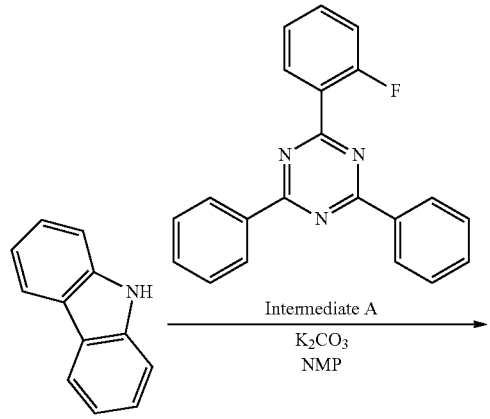

To a three-necked flask, 7.3 g of carbazole (43.6 mmol) 8.0 g of the intermediate A (24.4 mmol), 7.4 g of potassium carbonate (53.5 mmol), and 50 mL of N-methyl-2-pyrrolidone (NMP) were added and the mixture solution was heated and refluxed under an argon as atmosphere at 150 degrees C. for 20 hours. After heating and stirring, the reaction solution was poured in 200 mL of water and precipitated solid was collected by filtration. Subsequently, the solid vas repeatedly suspended and washed in ethanol to obtain a target substance (compound TADF-1) in a form of a white solid. A yield of the compound TADF-1 was 6.3 g and yield rate of the compound TADF-1 was 54%. As a result of FD-MS (Field Desorption Mass Spectrometry) analysis, m/e was equal to 474 while a calculated molecular weight was 474.

<Synthesis Example 2> Synthesis of Compound TADF-2

(1) Synthesis of Intermediate B

[Formula 77]

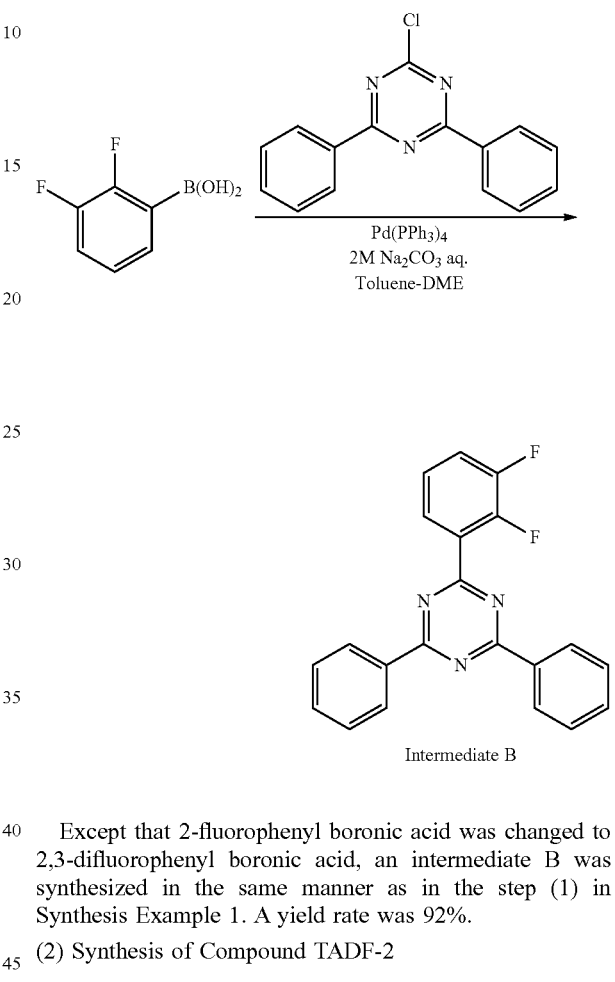

Except that 2-fluorophenyl boronic acid was changed to 2,3-difluorophenyl boronic acid, an intermediate B was synthesized in the same manner as in the step (1) in Synthesis Example 1. A yield rate was 92%.

(2) Synthesis of Compound TADF-2

[Formula 78]

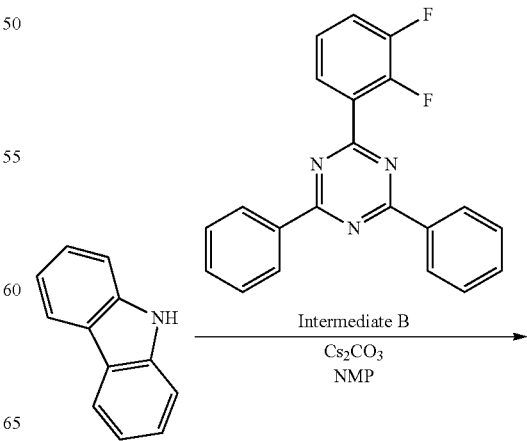

79

-continued

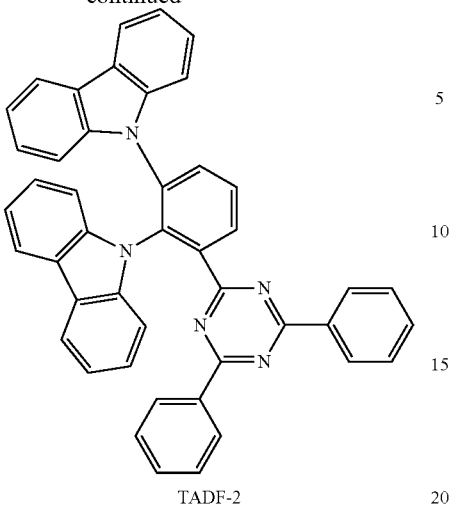

TADF-2

To a three-necked flask, 6.0 g of carbazole (35.9 mmol), 2.5 g of the intermediate B (7.24 mmol), 11.8 g of cesium carbonate (36.2 mmol), and 30 mL of N-methyl-2-pyrrolidone (NMP) were added and the mixture solution was heated and stirred under an argon gas atmosphere at 150 degrees C. for 40 hours. After heating and stirring, the reaction solution was poured in 200 mL of water and precipitated solid was collected by filtration. Subsequently, the solid was repeatedly suspended and washed in ethanol and acetone to obtain a target substance (compound TADF-2) in a form of a pale yellow solid. A yield of the compound TADF-2 was 3.6 g and yield rate of the compound TADF-2 was 77%. As a result of FD-MS analysis, m/e was equal to 639 while a calculated molecular weight was 639.

<Synthesis Example 3> Synthesis of Compound TADF-3

(1) Synthesis of Intermediate C

[Formula 79]

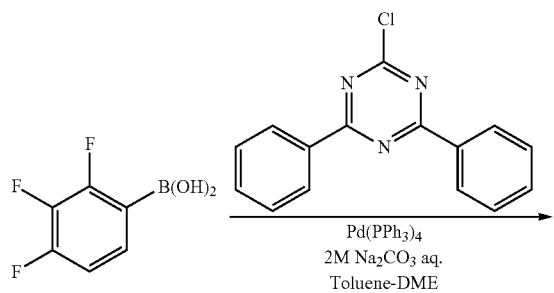

80

-continued

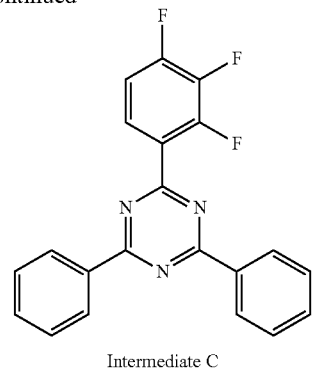

Intermediate C

Except that 2-fluorophenyl boronic acid was changed to 2,3,4-trifluorophenyl boronic acid, an intermediate C was synthesized in the same manner as in the step (1) in Synthesis Example 1. A yield rate was 82%.

(2) Synthesis of Compound TADF-3

[Formula 80]

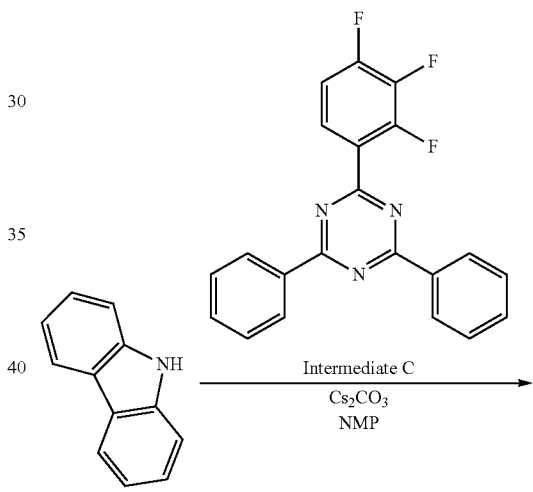

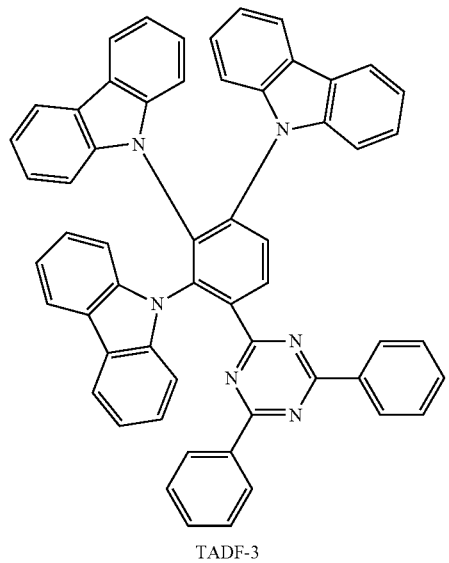

TADF-3

To a three-necked flask, 10.8 g of carbazole (64.4 mmol), 3.9 g of the intermediate C (10.7 mmol), 21.0 g of cesium carbonate (64.4 mmol), and 30 mL of N-methyl-2-pyrrolidone (NMP) were added and the mixture solution was heated and stirred under an argon gas atmosphere at 150 degrees C. for 24 hours. After heating and stirring, the reaction solution was poured in 300 mL a water and precipitated solid was collected by filtration. Subsequently, the solid was repeatedly suspended and washed in ethanol, acetone and ethyl acetate to obtain a target substance (compound TADF-3) in a form of a pale yellow solid. A yield of the compound TADF-3 was 7.5 g and yield rate of the compound TADF-3 was 87%. As a result of FD-MS analysis, m/e was equal to 804 while a calculated molecular weight was 804.

<Synthesis Example 4> Synthesis of Compound TADF-4

(1) Synthesis of Intermediate D

[Formula 81]

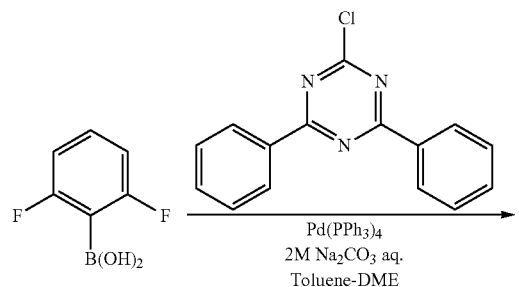

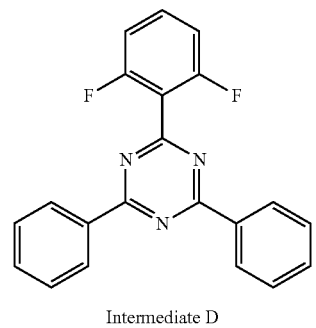

Intermediate D

Except that 2-fluorophenyl boronic acid was changed to 2,6-difluorophenyl boronic acid, an intermediate D was synthesized in the same manner as in the step (1) in Synthesis Example 1. A yield rate was 91%.

(2) Synthesis of Compound TADF-4

[Fromula 82]

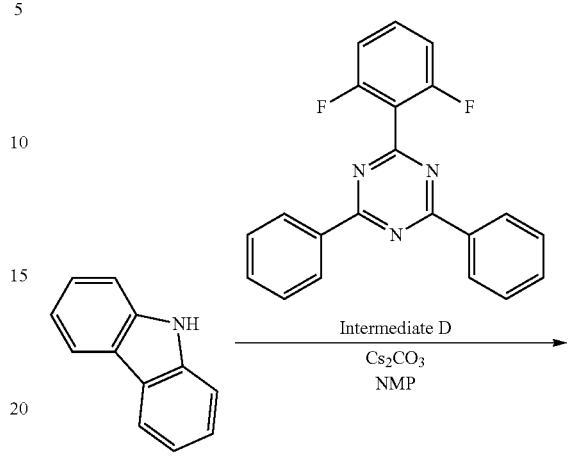

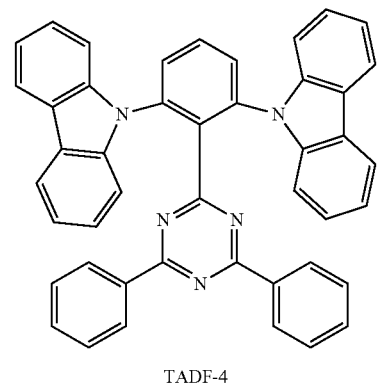

TADF-4

To a three-necked flask, 3.3 g of carbazole (19.7 mmol), 3.1 g of the intermediate D (9.0 mmol), 6.4 g of cesium carbonate (19.7 mmol), and 20 mL of N-methyl-2-pyrrolidone (NMP) were added and the mixture solution was heated and refluxed under an argon gas atmosphere at 150 degrees C. for 48 hours. After heating and stirring, the reaction solution was poured in 300 mL of water and precipitated solid was collected by filtration. Subsequently, the solid was repeatedly suspended and washed in ethanol, acetone and ethyl acetate to obtain a target substance (compound TADF-4) in a form of a white solid. A yield of the compound TADF-4 was 4.0 g and yield rate of the compound TADF-4 was 60%. As a result of FD-MS analysis, m/e was equal to 639 while a calculated molecular weight was 639.

Synthesis Example 5> Synthesis of Compound TADF-5

(1) Synthesis of Intermediate E

[Formula 83]

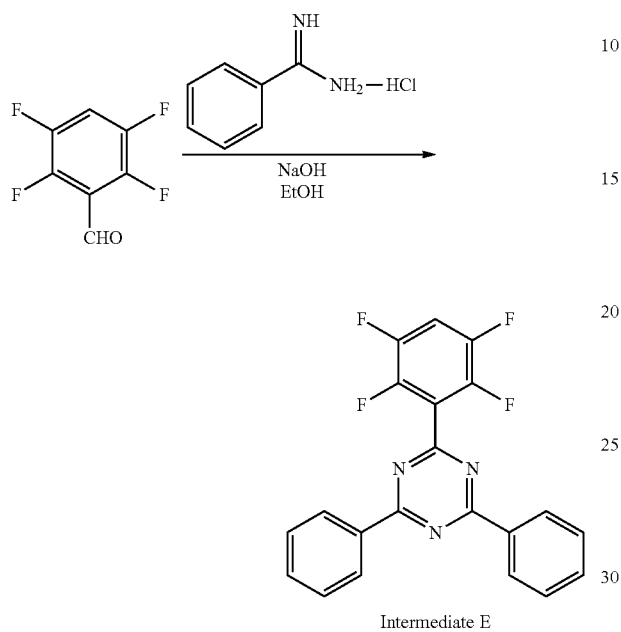

Intermediate E

After adding 19.3 of benzamidine hydrochloride (123.5 mmol) to 100 mL of ethanol, 5.4 g sodium hydroxylate (134.6 mmol) was added and the mixture solution was heated to 90 degrees C. Subsequently, 10.0 g of 2,3,5,6-tetrafluorobenzaldehyde (56.1 mmol) dissolved in 30 mL of ethanol was dropped in the mixture solution and the mixture solution was continuously stirred at 90 degrees C. for 24 hours. Precipitated solid was collected by filtration and the collected solid was washed with ethanol to obtain 9.0 g of an intermediate E.

(2) Synthesis of Compound TADF-5

[Formula 84]

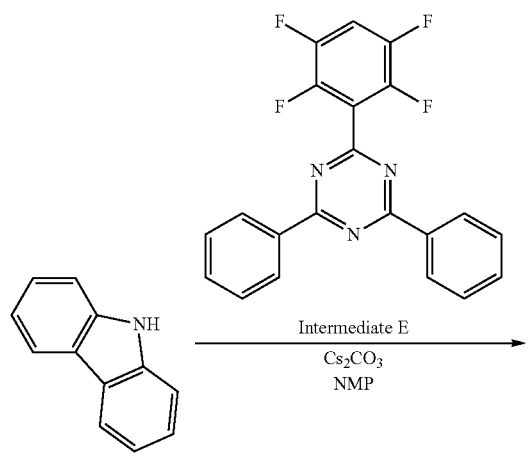

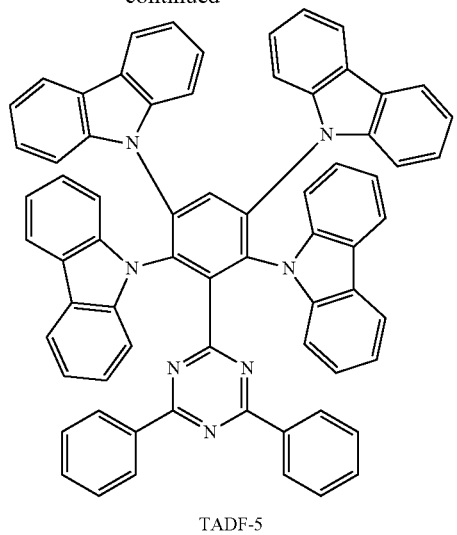

TADF-5

To a three-necked flask, 5.3 g of carbazole (31.4 mmol), 2.0 g of the intermediate E (5.2 mmol), 10.2 g of cesium carbonate (31.4 mmol), and 0.20 mL of N-methyl-2-pyrrolidone (NMP) were added and the mixture solution was heated and stirred under an argon gas atmosphere at 150 degrees C. for 24 hours. After heating and stirring, the reaction solution was poured in 300 mL of water and precipitated solid was collected by filtration. Subsequently, the solid was repeatedly suspended and washed in ethanol, acetone and ethyl acetate to obtain a target substance (compound TADF-5) in a form of a pale yellow solid. A yield of the compound TADF-5 was 3.0 g and yield rate of the compound TADF-5 was 59%. As a result of FD-MS analysis, m/e was equal to 970 while a calculated molecular weight was 970.

Evaluation of Compounds

Next, properties of the compounds used in Examples were measured. A measurement method and a calculation method are shown below.

Measurement of Fluorescence Lifetime

A sample for measuring fluorescence lifetime was manufactured according to the following method.

Specifically, a vapor-deposition film having the following composition and thickness was formed on a quartz substrate using a vacuum deposition apparatus.

Fluorescence measurement sample 1: (composition) TADF-1, (film thickness) 100 nm In the same manner, a fluorescence measurement sample 2 using the compound TADF-2, a fluorescence measurement sample 3 using the compound TADF-3, and a fluorescence measurement sample 4 using the compound REF-1 were manufactured.

[Formula 85]

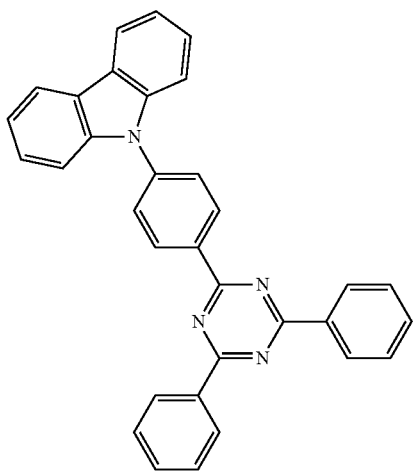

REF-1

Delayed fluorescence lifetime was measured for each of the manufactured fluorescence lifetime measurement samples 1 to 4. To measure the delayed fluorescence lifetime, a fluorescence lifetime photometer TemPro (manufactured by HORIBA, Ltd.) was used. As an excitation light source for measurement of the delayed-fluorescence lifetime, a semiconductor pulse LED light source NanoLED-340 or a semiconductor pulse LED light source SpectraLED-355 was used. Each of the excitation light sources was used depending on the delayed fluorescence lifetime. The measurement was conducted at room temperature.

Figure 6:
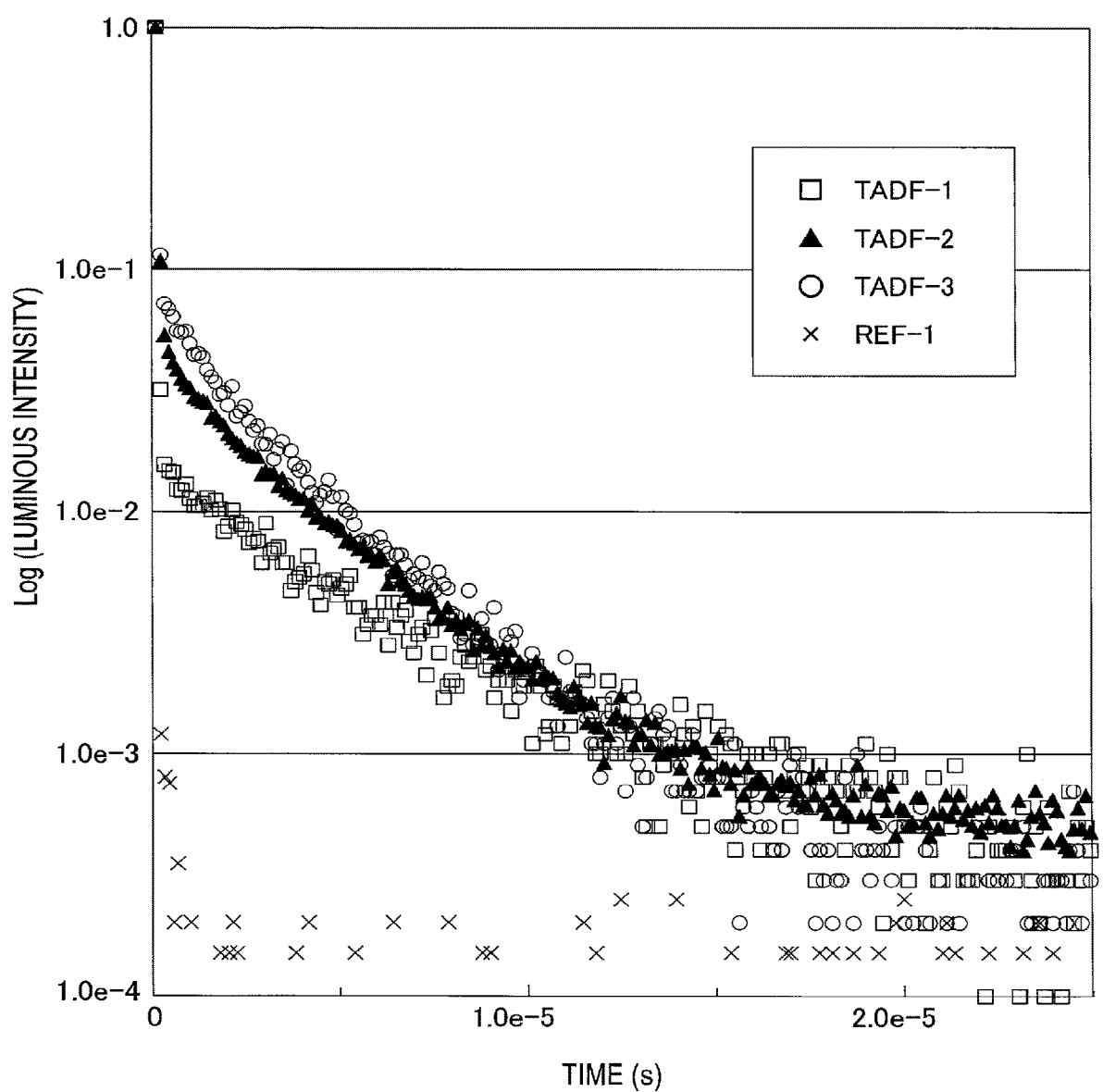
FIG. 6 is a view showing measurements of fluorescence lifetime of compounds used in Examples.

The measurement results of the fluorescence lifetime are shown in FIG. 6.

As shown in FIG. 6, all of the compound TADF1, the compound TADF2 and the compound TADF3 are delayed fluorescent compounds. It is observed that, compared to the compound REF-1 as a comparative example, the delayed fluorescence of microsecond order are significantly increased. This is believed to be because the substituents are bonded to an ortho position of an aromatic ring bonded to the electron acceptor portion of the compounds TADF1, TADF2 and TADF3 (corresponding to the triazine ring in these compounds), so that the separation between the electron acceptor portion and the electron donor portion (corresponding to the carbazole ring in these compounds) is enhanced.

Further, it is speculated that, since the compound TADF-2 and the compound TADF-3 having the electron donor portions bonded to the adjacent carbon atom exhibits enhanced delayed fluorescence as compared to the compound REF-1, interaction between the electron donor portions (corresponding to the carbazole rings in these compounds) contributes to the enhancement in the delayed fluorescence.

Singlet Energy S

Singlet energy S was measured as follows. A 10 μmol/L toluene solution of a measurement target compound was manufactured and put in a quartz cell. An absorption spectrum (ordinate axis: luminous intensity, abscissa axis: wavelength) of the thus-obtained sample was measured at a normal temperature (300K). A tangent was drawn to the fall of the absorption spectrum on the long-wavelength side, and a wavelength value λedge (nm) at an intersection of the tangent and the abscissa axis was assigned to a conversion equation 2 below to calculate singlet energy.

$S$ [eV]=1239.85/λedge            Conversion equation 2:

In Examples, the absorption spectrum was measured using a spectrophotometer (U3310 manufactured by Hitachi, Ltd.). It should be noted that the absorption spectrum measuring device may be different from the above device.

The calculated singlet energy S is shown below.

TADF-1: 2.9 eV
TADF-2: 2.9 eV
TADF-3: 2.9 eV
DPEPO: 4.0 eV (a value in a document: APPLIED PHYSICS LETTERS 101, 093306 (2012))

Preparation and Evaluation of Organic EL Device

The organic EL device was manufactured and evaluated as follows.

Example 1

A glass substrate (size: 25 mm×75 mm×1.1 mm thick, manufactured by Geomatec Co., Ltd.) having an ITO transparent electrode (anode) was ultrasonic-cleaned in isopropyl alcohol for five minutes, and then UV/ozone-cleaned for 30 minutes. A film of ITO was set to be 130-nm thick.

After the glass substrate having the transparent electrode line was cleaned, the glass substrate was mounted on a substrate holder of a vacuum evaporation apparatus. Initially, a compound HI was vapor-deposited on a surface of the glass substrate where the transparent electrode line was provided in a manner to cover the transparent electrode, thereby forming a 5-nm-thick hole injecting layer.

Next, the compound HT-1 was vapor-deposited on the hole injecting layer to form a 80-nm-thick first hole transporting layer on the HI film.

Subsequently, the compound HT-2 was vapor-deposited on the first hole transporting layer to form a 15-nm-thick second hole transporting layer.

Further, mCP was vapor-deposited on the second hole transporting layer to form a 5-nm-thick third hole transporting layer.

The compound TADF-1 (the first compound), the compound BD-1 (the second compound) and the third compound DPEPO (the third compound) were co-deposited to form a 25-nm-thick emitting layer. In the emitting layer, the concentrations of the compounds TADF-1, BD-1 and DPEPO were respectively 24 mass %, 1 mass % and 75 mass %.

The compound ET-1 was then vapor-deposited on the emitting layer to form a 5-nm-thick first electron transporting layer.

The compound ET-2 was then vapor-deposited on the first electron transporting layer to form a 20-nm-thick second electron transporting layer.

Next, lithium fluoride (LiF) was vapor-deposited on the second electron transporting layer to form a 1-nm-thick electron injecting electrode (cathode).

A metal aluminum (Al) was then vapor-deposited on the electron injecting electrode to form an 80-nm-thick metal Al cathode.

A device arrangement of the organic EL device of Example 1 is roughly shown as follows.

ITO (130)/HI-1 (5)/HT-1 (80)/HT-2 (15)/mCP (5)/DPEPO:TADF-1:BD-1 (25.75%:24%:1%)/ET-1 (5): ET-2 (20)/LiF (1)/Al (80)

Numerals in parentheses represent a film thickness (unit: nm). The numerals represented by percentage in parentheses indicate a ratio (mass %) of the first, second and third compounds in the emitting layer.

Example 2

An organic EL device of Example 2 was manufactured in the same manner as the organic EL device of Example 1 except that the compound TADF-2 was used in place of the compound TADF-1 in the emitting layer of Example 1.

A device arrangement of the organic EL device of Example 2 is roughly shown as follows.

ITO (130)/HI (5)/HT-1 (80)/HT-2 (15)/mCP (5)/DPEPO: TADF-2:BD-1 (25.75%:24%:1%)/ET-1 (5): ET-2 (20)/LiF (1)/Al (80)

Example 3

An organic EL device of Example 3 was manufactured in the same manner as the organic EL device of Example 1 except that the compound TADF-3 was used in place of the compound TADF-1 in the emitting layer of Example 1.

A device arrangement of the organic EL device of Example 3 is roughly shown as follows.

ITO (130)/HI (5)/HT-1 (80)/HT-2 (15)/mCP (5)/DPEPO: TADF-3:BD-1 (25.75%:24%:1%)/ET-1 (5): ET-2 (20)/LiF (1)/Al (80)

Example 4

An organic EL device of Example 4 was manufactured in the same manner as the organic EL device of Example 1 except that the compound TADF-4 was used in place of the compound TADF-1 in the emitting layer of Example 1.

A device arrangement of the organic EL device of Example 4 is roughly shown as follows.

ITO (130)/HI (5)/HT-1 (80)/HT-2 (15)/mCP (5)/DPEPO: TADF-4:BD-1 (25.75%:24%:1%)/ET-1 (5): ET-2 (20)/LiF (1)/Al (80)

Example 5

An organic EL device of Example 5 was manufactured in the same manner as the organic EL device of Example 1 except that the compound TADF-5 was used in place of the compound TADF-1 in the emitting layer of Example 1.

A device arrangement of the organic EL device of Example 5 is roughly shown as follows.

ITO (130)/HI (5)/HT-1 (80)/HT-2 (15)/mCP (5)/DPEPO: TADF-5:BD-1 (25.75%:24%:1%)/ET-1 (5): ET-2 (20)/LiF (1)/Al (80)

Example 6

An organic EL device of Example 6 was manufactured in the same manner as the organic EL device of Example 1 except that the compound BD-2 was used in place of the compound BD-1 in the emitting layer of Example 1.

A device arrangement of the organic EL device of Example 6 is roughly shown as follows.

ITO (130)/HI (5)/HT-1 (80)/HT-2 (15)/mCP (5)/DPEPO: TADF-1:BD-2 (25.75%:24%:1%)/ET-1 (5): ET-2 (20)/LiF (1)/Al (80)

Example 7

An organic EL device of Example 7 was manufactured in the same manner as the organic EL device of Example 1 except that the compound TADF-5 was used in place of the compound TADF-1 and the compound BD-2 was used in place of the compound BD-2 in the emitting layer of Example 1.

A device arrangement of the organic EL device of Example 7 is roughly shown as follows.

ITO (130)/HI (5)/HT-1 (80)/HT-2 (15)/mCP (5)/DPEPO: TADF-5:BD-2 (25.75%:24%:1%)/ET-1 (5): ET-2 (20)/LiF (1)/Al (80)

Comparative Example 1

An organic EL device of Comparative Example 1 was manufactured in the same manner as the organic EL device of Example 1 except that the compound REF-1 was used in place of the compound TADF-1 in the emitting layer of Example 1.

A device arrangement of the organic EL device of Comparative Example 1 is roughly shown as follows.

ITO (130)/HI (5)/HT-1 (80)/HT-2 (15)/mCP (5)/DPEPO: REF-1:BD-1 (25.75%:24%:1%)/ET-1 (5): ET-2 (20)/LiF (1)/Al (80)

Compounds used for preparing the organic EL device will be shown below.

[Formula 86]

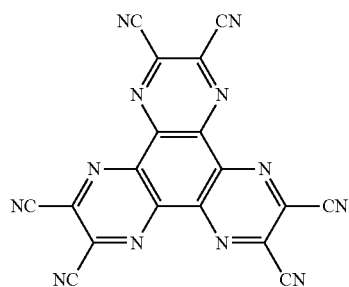

HI

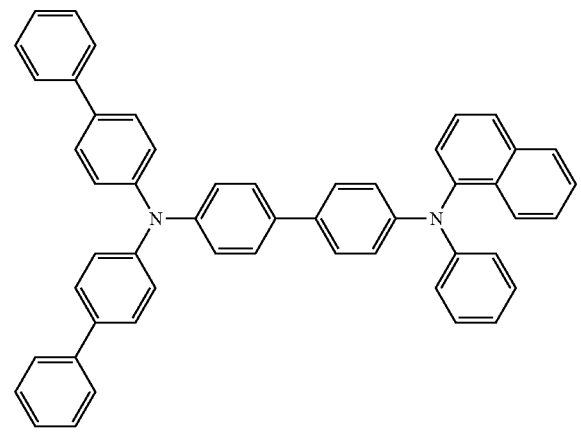

HT-1

-continued

HT-2

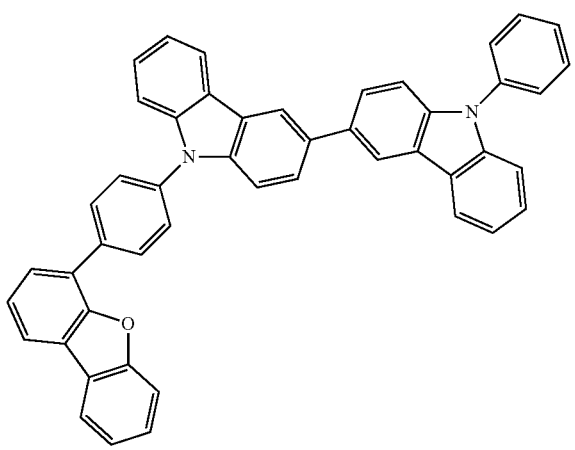

[Formula 87]

mCP

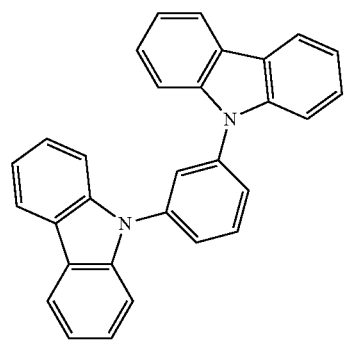

BD-1

[Formula 88]

ET-1

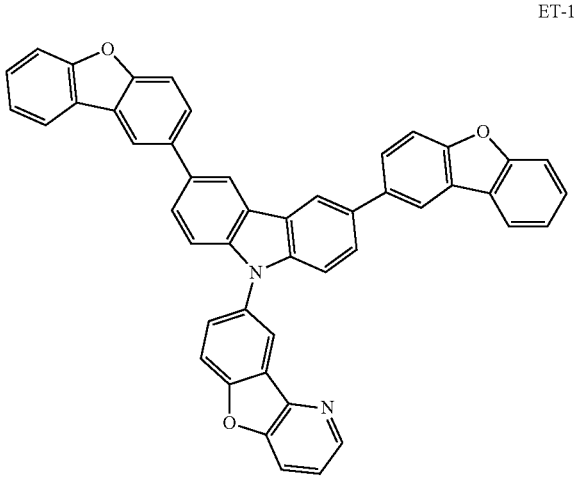

ET-2

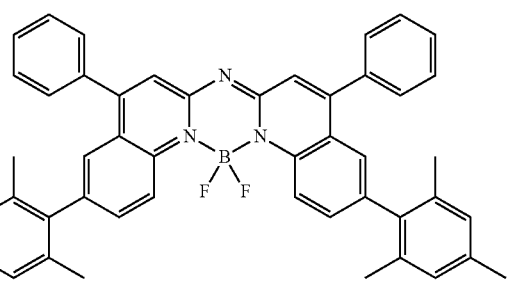

[Formula 89]

BD-2

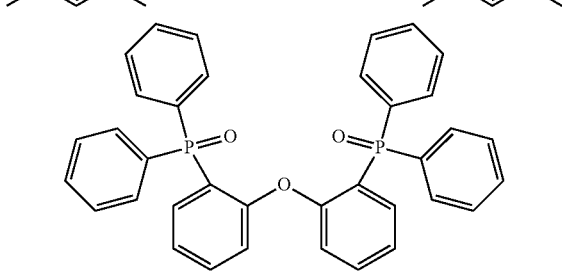

DPEPO

Evaluation of Organic EL Devices

The manufactured organic EL devices of Example 1 and Comparative Example 1 were evaluated as follows. The evaluation results are shown in Table 1.

External Quantum Efficiency EQE

Voltage was applied on each of the organic EL devices such that a current density was 0.1 mA/cm², where spectral radiance spectra were measured by a spectroradiometer (CS-1000 manufactured by Konica Minolta, Inc.). The external quantum efficiency EQE (unit: %) was calculated from the obtained spectral radiance spectra, assuming that the spectra were provided under a Lambertian radiation.

Main Peak Wavelength λp

Voltage was applied on each of the organic EL devices such that a current density was 0.1 mA/cm², where spectral radiance spectrum was measured by the spectroradiometer (CS-1000 manufactured by Konica Minolta, Inc.) and a main peak wavelength was calculated from the obtained spectral radiance spectrum. It should be noted that the main peak wavelength λp is defined as a peak wavelength at which the emission intensity is maximized in the spectrum.

TABLE 1

| | First Compound (Delayed Fluorescent) | Second Compound (Fluorescent) | EQE [%] | λp [nm] |
|---|---|---|---|---|
| Example 1 | TADF-1 | BD-1 | 15.4 | 451 |
| Example 2 | TADF-2 | BD-1 | 17.1 | 451 |
| Example 3 | TADF-3 | BD-1 | 14.8 | 451 |
| Example 4 | TADF-4 | BD-1 | 15.9 | 451 |
| Example 5 | TADF-5 | BD-1 | 16.7 | 451 |
| Example 6 | TADF-1 | BD-2 | 18.3 | 464 |
| Example 7 | TADF-5 | BD-2 | 17.2 | 464 |
| Comparative Example 1 | REF-1 | BD-1 | 9.2 | 451 |

As shown in Table 1, it is understood that the organic EL devices of Examples 1 to 7 using the delayed-fluorescent compounds TADF-1 to TADF-5 according to Examples of the invention show significantly improved external quantum efficiency as compared to Comparative Example 1 using the compound REF-1. Further, it is understood that, in view of the main peak wavelength, the emissions of the organic EL devices in Examples and Comparative are derived from the fluorescent compounds BD-1 and BD-2.

The invention claimed is:

1. An organic electroluminescence device comprising:
an anode;
an emitting layer; and
a cathode, wherein
the emitting layer comprises a delayed-fluorescent first compound and a fluorescent second compound,
wherein a singlet energy S1(M1) of the delayed-fluorescent first compound is larger than a singlet energy S1(M2) of the fluorescent second compound, and
the delayed-fluorescent first compound is represented by a formula (11aa), a formula (11 bb) or a formula (11cc),

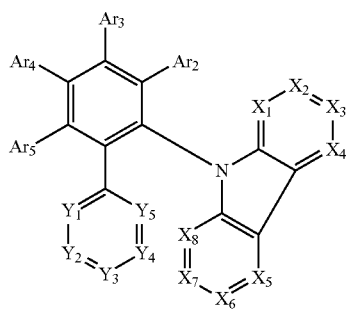
(11aa)

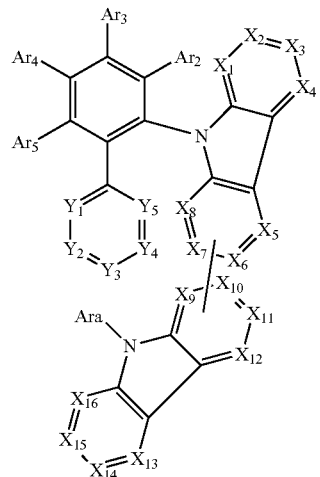
(11bb)

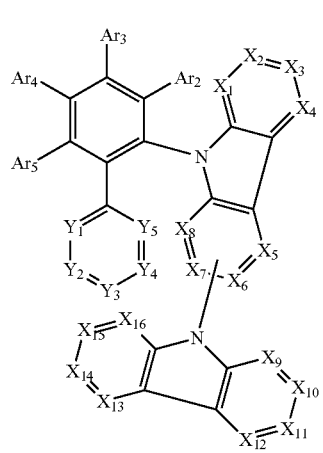
(11cc)

wherein, in the formula (11aa), the formula (11bb) or the formula (11cc):

$Y_1$ to $Y_5$ are each independently N, C—CN or C—$R_y$, at least one of $Y_1$ to $Y_5$ being N or C—CN;

$R_y$ is each independently a hydrogen atom or a substituent, and $R_y$ as a substituent is a group selected from the group consisting of an unsubstituted aryl group having 6 to 30 ring carbon atoms an unsubstituted heteroaryl group having 5 to 30 ring atoms, an unsubstituted alkyl group having 1 to 30 carbon atoms, an unsubstituted fluoroalkyl group having 1 to 30 carbon atoms an unsubstituted cycloalkyl group having 3 to 30 ring carbon atoms, an unsubstituted aralkyl group having 7 to 30 carbon atoms, a substituted phosphoryl group, a substituted silyl group, a cyano group, a nitro group, and a carboxy group;

a plurality of $R_y$s are mutually the same or different;

$Ar_2$ to $Ar_5$ are each independently a hydrogen atom or a substituent, $Ar_2$ to $Ar_5$ as substituents are groups selected from the group consisting of an unsubstituted aryl group having 6 to 30 ring carbon atoms, an unsubstituted heteroaryl group having 5 to 30 ring atoms, an unsubstituted alkyl group having 1 to 30 carbon atoms, an unsubstituted fluoroalkyl group having 1 to 30 carbon atoms, an unsubstituted cycloalkyl group having 3 to 30 ring carbon atoms, an unsubstituted aralkyl group having 7 to 30 carbon atoms, a substituted phosphoryl group, a substituted silyl group, a cyano group, a nitro group, a carboxy group, and the groups represented by formulae (1a) to (ac) as defined below; and $X_1$ to $X_{16}$ are each independently N or C—Rx: with a proviso that:

in the formula (11bb), at least one of $X_5$ to $X_8$ is a carbon atom bonded to at least one of $X_9$ to $X_{12}$, and at least one of $X_9$ to $X_{12}$ is a carbon atom bonded to at least one of $X_5$ to $X_8$;

in the formula (11cc), at least one of $X_5$ to $X_8$ is a carbon atom bonded to the nitrogen atom;

$R_X$ is each independently a hydrogen atom or a substituent, and Rx as a substituent is a group selected from the group consisting of an unsubstituted aryl group having 6 to 30 ring carbon atoms, an unsubstituted heteroaryl group having 5 to 30 ring atoms, an unsubstituted alkyl group having 1 to 30 carbon atoms, an unsubstituted fluoroalkyl group having 1 to 30 carbon atoms, an unsubstituted cycloalkyl group having 3 to 30 ring carbon atoms, an unsubstituted aralkyl group having 7 to 30 carbon atoms a substituted phosphoryl group, a substituted silyl group, a cyano group, a nitro group and a carboxy group;

a plurality of Rxs as substituents are mutually the same or different;

the plurality of Rxs as the substituents are directly bonded to each other to form a ring, are bonded via a hetero atom to form a ring or do not form a ring;

Ara is a group selected from the group consisting of an unsubstituted aryl group having 6 to 30 ring carbon atoms, an unsubstituted heteroaryl group having 5 to 30 ring atoms, an unsubstituted alkyl group having 1 to 30 carbon atoms, an unsubstituted fluoroalkyl group having 1 to 30 carbon atoms, an unsubstituted cycloalkyl group having 3 to 30 ring carbon atoms, an unsubstituted aralkyl group having 7 to 30 carbon atoms, a substituted phosphoryl group, and a substituted silyl group,

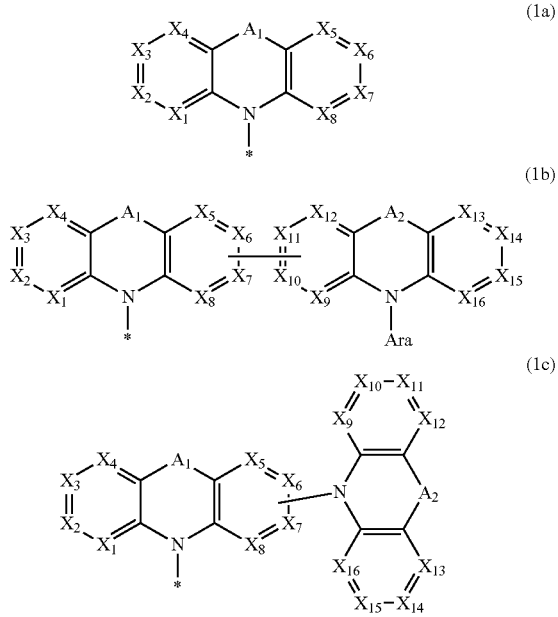

wherein, in the formula (1a to (1c); $X_1$ to $X_{16}$ are each independently N or C—Rx; with a proviso that:

in the formula (1b), one of $X_5$ to $X_8$ is a carbon atom bonded to one of $X_9$ to $X_{12}$, and one of $X_8$ to $X_{12}$ is a carbon atom bonded to one of $X_5$ to $X_8$;

in the formula (1c), one of $X_5$ to $X_8$ is a carbon atom bonded to the nitrogen atom in the ring comprising $A_2$;

$R_X$ is each independently a hydrogen atom or a substituent, and Rx as a substituent is a group selected from the group consisting an unsubstituted aryl group having 6 to 30 ring carbon atoms, an unsubstituted heteroaryl group having 5 to 30 ring atoms, an unsubstituted alkyl group having 1 to 30 carbon atoms, an unsubstituted fluoroalkyl group having 1 to 30 carbon atoms, an unsubstituted cycloalkyl group having 3 to 30 ring carbon atoms, an unsubstituted aralkyl group having 7 to 30 carbon atoms, a substituted phosphoryl group, a substituted silyl group, a cyano group, a nitro group, and a carboxy group;

a plurality of Rxs as substituents are mutually the same or different;

the plurality of Rxs as the substituents are directly bonded to each other to form a ring, are bonded via a hetero atom to form a ring, or do not form a ring;

$A_1$ and $A_2$ are each independently a single bond, O, S, $C(R_1)(R_2)$, $Si(R_3)(R_4)$, $C(=O)$, $S(=O)$, $SO_2$ or $N(R_5)$;

$R_1$ to $R_5$ are each independently a hydrogen atom or a substituent, and $R_1$ to $R_5$ as substituents are groups selected from the group consisting of an unsubstituted aryl group having 6 to 30 ring carbon atoms; an unsubstituted heteroaryl group having 5 to 30 ring atoms, an unsubstituted alkyl group having 1 to 30 carbon atoms, an unsubstituted fluoroalkyl group having 1 to 30 carbon atoms, an unsubstituted cycloalkyl group having 3 to 30 ring carbon atoms, an unsubstituted aralkyl group having 7 to 30 carbon atoms, a substituted phosphoryl group, a substituted silyl group, a cyano group, a nitro group, and a carboxy group; and Ara is a group selected from the group consisting of an unsubstituted aryl group having 6 to 30 ring carbon atoms, an unsubstituted heteroaryl group having 5 to 30 ring atoms, an unsubstituted alkyl group having 1 to 30 carbon atoms, an unsubstituted fluoroalkyl group having 1 to 30 carbon atoms, an unsubstituted cycloalkyl group having 3 to 30 ring carbon atoms, an unsubstituted aralkyl group having 7 to 30 carbon atoms, a substituted phosphoryl group, and a substituted silyl group.

2. The organic electroluminescence device according to claim 1, wherein $Ar_2$ is any group selected from the group consisting of groups represented by the formulae (1a) to (1c), or $Ar_2$ and $Ar_3$ are any group selected from the group consisting of groups represented by the formulae (1a) to (1c).

3. The organic electroluminescence device according to claim 1, wherein $Ar_2$ and $Ar_3$ are selected from the group consisting of groups represented by the formulae (1a) to (1c).

4. The organic electroluminescence device according to claim 1, wherein in the formula (1a), when $X_1$ to $X_8$ are carbon atoms bonded to Rx (C-Rx), the plurality of Rxs as substituents do not form a ring.

5. The organic electroluminescence device according to claim 1, wherein at least one of $Y_1$, $Y_3$ and $Y_5$ is N.

6. The organic electroluminescence device according to claim 1, wherein $Y_1$ and $Y_3$ are N, and $Y_2$, $Y_4$ and $Y_5$ are C-Ry.

7. The organic electroluminescence device according to claim 1, wherein $Y_1$ and $Y_5$ are N, and $Y_2$, $Y_3$ and $Y_4$ are C-Ry.

8. The organic electroluminescence device according to claim 1, wherein $Y_1$, $Y_3$ and $Y_5$ are N, and $Y_2$ and $Y_4$ are C-Ry.

9. The organic electroluminescence device according to claim 1, wherein the emitting layer further comprises a third compound, and the third compound has a singlet energy larger than a singlet energy of the first compound.

10. The organic electroluminescence device according to claim 9, wherein the third compound comprises at least one of a moiety represented by a formula (31) and a moiety represented by a formula (32) in one molecule,

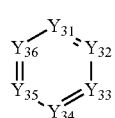
(31)

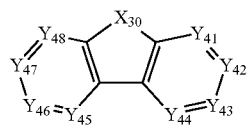
(32)

wherein, in the formula (31): $Y_{31}$ to $Y_{36}$ are each independently a nitrogen atom or a carbon atom bonded to another atom in the molecule of the third compound, with a proviso that at least one of $Y_{31}$ to $Y_{36}$ is a carbon atom bonded to another atom in the molecule of the third compound; and wherein, in the formula (32): $Y_{41}$ to $Y_{48}$ are each independently a nitrogen atom or a carbon atom bonded to another atom in the molecule of the third compound, with a proviso that at least one of $Y_{41}$ to $Y_{48}$ is a carbon atom bonded to another atom in the molecule of the third compound; and $X_{30}$ is a nitrogen atom, an oxygen atom or a sulfur atom.

11. The organic electroluminescence device according to claim 1, further comprising a hole transporting layer between the anode and the emitting layer.

12. The organic electroluminescence device according to claim 1, further comprising an electron sporting layer between the cathode and the emitting layer.

13. An electronic device comprising the organic electroluminescence device according to claim 1.

14. The organic electroluminescence device according to claim 1, wherein $Ar_5$ is any group selected from the group consisting of groups represented by the formulae (1a) to (1c).

15. A compound represented by a formula (11a), a formula (11b) or a formula (11c),

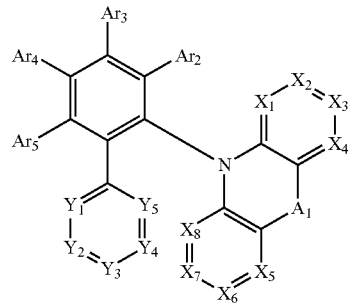
(11a)

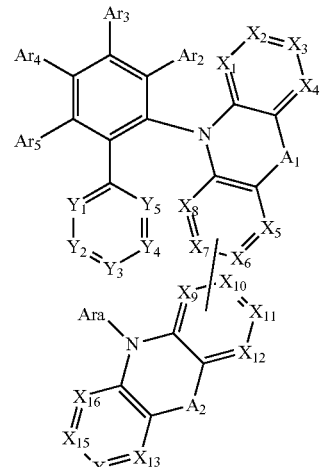
(11b)

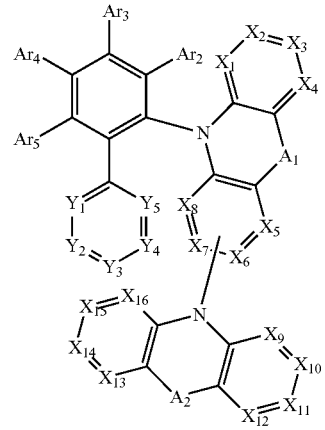
(11c)

wherein, in the formula (11a), a formula (11b) or a formula (11c):

$Y_1$ to $Y_5$ are each independently N, C—CN or C-Ry, at least one of $Y_1$ to $Y_5$ being N or C—CN;

Ry is each independently a hydrogen atom or a substituent and Ry as a substituent is a group selected from the group consisting of an unsubstituted aryl group having 6 to 30 ring carbon atoms, unsubstituted heteroaryl group having 5 to 30 ring atoms, an unsubstituted alkyl group having 1 to 30 carbon atoms, an unsubstituted fluoroalkyl group having 1 to 30 carbon atoms, an unsubstituted cycloalkyl group having 3 to 30 ring carbon atoms, an unsubstituted aralkyl group having 7 to 30 carbon atoms, a substituted phosphoryl group, a substituted silyl group, a cyano group, a nitro group, and a carboxy group;

a plurality of $R_y$s are mutually the same or different, $Ar_2$ to $Ar_5$ are each independently a hydrogen atom or a substituent, $Ar_2$ to $Ar_5$ as substituents are groups selected from the group consisting of an unsubstituted aryl group having 6 to 30 ring carbon atoms, an unsubstituted heteroaryl group having 5 to 30 ring atoms, an unsubstituted alkyl group having 1 to 30 carbon atoms, an unsubstituted fluoroalkyl group having 1 to 30 carbon atoms, an unsubstituted cycloalkyl group having 3 to 30 ring carbon atoms, an unsubstituted aralkyl group having 7 to 30 carbon atoms, a substituted phosphoryl group, a substituted silyl group a cyano group, a nitro group, a carboxy group, and the groups represented by formulae (1a) to (1c) as defined below: with a proviso that (i) $Ar_2$ is a group represented by any one of the formulae (1a) to (1c) and none of $Ar_3$ to $Ar_5$ is a group represented by any one of the formulae (1a) to (1c), (ii) $Ar_5$ is a group represented by any one of the formulae (1a) to (1c) and none of $Ar_2$ to $Ar_4$ is a group represented by any one of the formulae (1a) to (1c), or (iii) $Ar_2$ and $Ar_3$ are each independently a group represented by any one of the formulae (1a) to (1c), and none of $Ar_4$ and $Ar_5$ is a group represented by any one of the formulae (1a) to (1c), $Y_2$ and $Y_4$ being C—$R_y$, $R_y$ being an unsubstituted aryl group having 6 to 30 ring carbon atoms;

$X_1$ to $X_{16}$ are each independently N or C-Rx: with a proviso that:

in the formula (11b), at least one of $X_5$ to $X_8$ is a carbon atom bonded to at least one of $X_9$ to $X_{12}$, and at least one of $X_9$ to $X_{12}$ is a carbon atom bonded to at least one of $X_5$ to $X_8$;

in the formula (11c), at least one of $X_5$ to $X_8$ is a carbon atom bonded to the nitrogen atom in the ring comprising $A_2$;

$R_X$ is each independently a hydrogen atom or a substituent, and Rx as a substituent is a group selected from the group consisting of an unsubstituted aryl group having 6 to 30 ring carbon atoms, an unsubstituted heteroaryl group having 5 to 30 ring atoms, an unsubstituted alkyl group having 1 to 30 carbon atoms, an unsubstituted fluoroalkyl group having 1 to 30 carbon atoms, an unsubstituted cycloalkyl group having 3 to 30 ring carbon atoms, an unsubstituted aralkyl group having 7 to 30 carbon atoms, a substituted phosphoryl group, a substituted silyl group, a cyano group, a nitro group, and a carboxy group;

a plurality of Rxs as substituents are mutually the same or different, the plurality of Rxs as the substituents are directly bonded to each other to form a ring, are bonded via a hetero atom to form a ring or do not form a ring;

$A_1$ and $A_2$ are each independently a single bond, O, S, C($R_1$)($R_2$) Si $R_3$)($R_4$), C(=O), S(=O), $SO_2$ or N($R_5$);

$R_1$ to $R_5$ are each independently a hydrogen atom or a substituent, and $R_1$ to $R_5$ as substituents are groups selected from the group consisting of an unsubstituted aryl group having 6 to 30 ring carbon atoms, an unsubstituted heteroaryl group having 5 to 30 ring atoms, an unsubstituted alkyl group having 1 to 30 carbon atoms, an unsubstituted fluoroalkyl an group having 1 to 30 carbon atoms, an unsubstituted cycloalkyl group having 3 to 30 ring carbon atoms, an unsubstituted aralkyl group having 7 to 30 carbon atoms, a substituted phosphoryl group, a substituted silyl group, a cyano group, a nitro group, and a carboxy group; and Ara is a group selected from the group consisting of an unsubstituted aryl group having 6 to 30 ring carbon atoms, an unsubstituted heteroaryl group having 0.5 to 30 ring atoms, an unsubstituted alkyl group having 1 to 30 carbon atoms, an unsubstituted fluoroalkyl group having 1 to 30 carbon atoms, an unsubstituted cycloalkyl group having 3 to 30 ring carbon atoms, an unsubstituted aralkyl group having 7 to 30 carbon atoms, a substituted phosphoryl group, and a substituted silyl group,

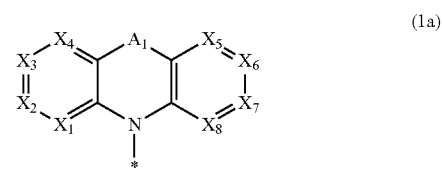

(1a)

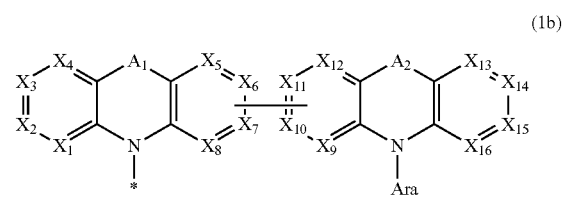

(1b)

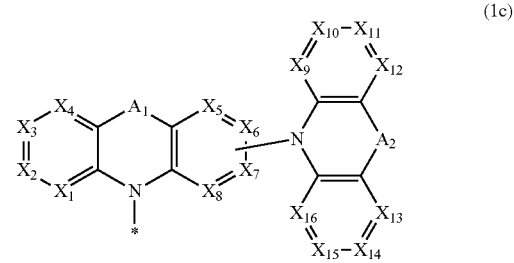

(1c)

wherein, in the formulae (1a) to (1c): $X_1$ to $X_{16}$ are each independently N or C-Rx; with a proviso that:

in the formula (1b), one of $X_5$ to $X_8$ is a carbon atom bonded to one of $X_9$ to $X_{12}$, and one of $X_9$ to $X_{12}$ is a carbon atom bonded to one of $X_5$ to $X_8$;

in the formula (1c), one of $X_5$ to $X_5$ is a carbon atom bonded to the nitrogen atom in the ring comprising $A_2$;

$R_X$ is each independently a hydrogen atom or a substituent, Rx as a substituent is a group selected from the group consisting of an unsubstituted aryl group having 6 to 30 ring carbon atoms, an unsubstituted heteroaryl group having 5 to 30 ring atoms, an unsubstituted alkyl group having 1 to 30 carbon atoms, an unsubstituted fluoroalkyl group having 1 to 30 carbon atoms, an unsubstituted cycloalkyl group having 3 to 30 ring carbon atoms, an unsubstituted aralkyl group having 7 to 30 carbon atoms, a substituted phosphoryl group, a substituted silyl group, a cyano group, a nitro group, and a carboxy group;

a plurality of Rxs as substituents are mutually the same or different;

the plurality of Rxs as the substituents being directly bonded to each other to form a ring, are bonded via a hetero atom to form a ring or do not form a ring;

$A_1$ and $A_2$ are each independently a single bond, O, S, $C(R_1)(R_2)$, $Si(R_3)(R_4)$, $C(=O)$, $S(=O)$, $SO_2$ or $N(R_5)$;

$R_1$ to $R_5$ are each independently a hydrogen atom or a substituent, and $R_1$ to $R_5$ as substituents are groups selected from the group consisting of an unsubstituted aryl group having 6 to 30 ring carbon atoms, an unsubstituted heteroaryl group having 5 to 30 ring atoms, an unsubstituted alkyl group having 1 to 30 carbon atoms, an unsubstituted fluoroalkyl group having 1 to 30 carbon atoms, an unsubstituted cycloalkyl group having 3 to 30 ring carbon atoms, an unsubstituted aralkyl group having 7 to 30 carbon atoms, a substituted phosphoryl group, a substituted silyl group, a cyano group, a nitro group, and a carboxy group; and Ara is a group selected from the group consisting of an unsubstituted aryl group having 6 to 30 ring carbon atoms, an unsubstituted heteroaryl group having 5 to 30 ring atoms, an unsubstituted alkyl group having 1 to 30 carbon atoms, an unsubstituted fluoroalkyl group having 1 to 30 carbon atoms, an unsubstituted cycloalkyl group having 3 to 30 ring carbon atoms, a substituted an unsubstituted aralkyl group having 7 to 30 carbon atoms, a substituted phosphoryl group, and a substituted silyl group.

16. The compound according to claim 15, wherein the compound is represented by a formula (11aa), a formula (11bb) or a formula (11cc),

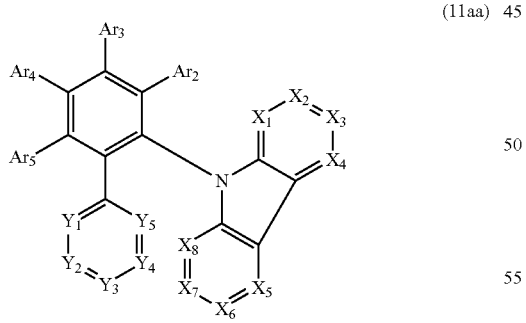

(11aa)

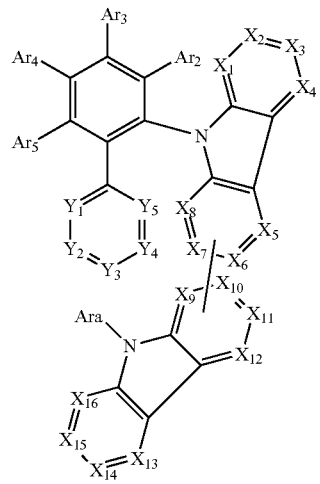

(11bb)

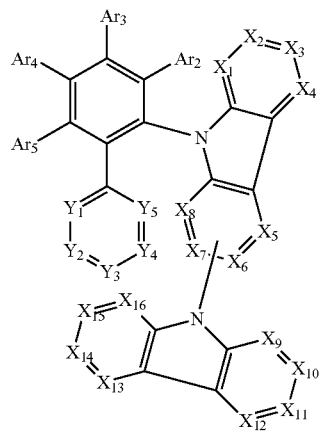

(11cc)

wherein $Y_1$ to $Y_5$, $R_y$, $Ar_2$ to $Ar_5$, $X_1$ to $X_{16}$, Rx, and Ara in the formulae (11aa), (11bb) and (11cc) are the same as $Y_1$ to $Y_5$, $R_y$, $Ar_2$ to $Ar_5$, $X_1$ to $X_{16}$, Rx, and Ara defined in the above.

17. The compound according to claim 16, wherein in the formulae (11aa), (11bb) and (11cc), $Ar_2$ is a group represented by any one of the formulae (1a) to (1c) and none of $Ar_3$ to $Ar_5$ is a group represented by any one of the formulae (1a) to (1c).

18. The compound according to claim 16, wherein in the formulae (11aa), (11bb) and (11 cc), $Ar_2$ is a group represented by any one of the formulae (1a) to (1c) and none of $Ar_2$ to $Ar_4$ is a group represented by any one of the formulae (1a) to (1c).

19. The compound according to claim 16, wherein in the formulae (11aa), (11bb) and (11cc), $Ar_2$ and $Ar_3$ are each independently a group represented by any one of the formulae (1a) to (1c), and none of $Ar_4$ and $Ar_5$ is a group represented by any one of the formulae (1a) to (1c), $Y_2$ and $Y_4$ being C-Ry, Ry being an unsubstituted aryl group having 6 to 30 ring carbon atoms.

* * * * *

UNITED STATES PATENT AND TRADEMARK OFFICE
CERTIFICATE OF CORRECTION

PATENT NO. : 10,547,009 B2
APPLICATION NO. : 15/557681
DATED : January 28, 2020
INVENTOR(S) : Kei Yoshida et al.

It is certified that error appears in the above-identified patent and that said Letters Patent is hereby corrected as shown below:

Column 91, Line 52, Claim 1 "11 bb" should read --11bb--.

Column 92, Line 42, Claim 1 "$R_y$" should read --Ry--.

Column 92, Line 44, Claim 1 "$R_y$" should read --Ry--.

Column 92, Line 45, Claim 1 "$R_y$" should read --Ry--.

Column 92, Line 56, Claim 1 "$R_y$s" should read --Rys--.

Column 93, Line 2, Claim 1 "(ac)" should read --(1c)--.

Column 93, Line 12, Claim 1 "$R_x$" should read --Rx--.

Column 93, Line 67, Claim 1 "(1a to (1c);" should read --(1a) to (1c):--.

Column 94, Line 2, Claim 1 "$X_8$ to $X_{12}$" should read --$X_9$ to $X_{12}$--.

Column 94, Line 6, Claim 1 "$R_x$" should read --Rx--.

Column 94, Line 8, Claim 1 "consisting an unsubstituted" should read --consisting of an unsubstituted--.

Column 96, Line 59, Claim 15 "unsubstituted" should read --an unsubstituted--.

Column 97, Line 1, Claim 15 "$R_y$s" should read --Rys--.

Column 97, Line 15, Claim 15 "below:" should read --belowx--.

Signed and Sealed this
Second Day of June, 2020

Andrei Iancu
*Director of the United States Patent and Trademark Office*

CERTIFICATE OF CORRECTION (continued)
U.S. Pat. No. 10,547,009 B2

Column 97, Line 26, Claim 15 "C-$R_y$, $R_y$" should read --C-Ry, Ry--.

Column 97, Line 39, Claim 15 "$R_X$" should read --RX--.

Column 97, Line 52, Claim 15 "different," should read --differentx--.

Column 97, Line 57, Claim 15 "($R_2$) Si $R_3$)" should read --($R_2$), Si($R_3$)--.

Column 98, Lines 6 and 7, Claim 15 "0.5 to 30" should read --5 to 30--.

Column 98, Line 54, Claim 15 "g $_5$ to g $_5$" should read --g $_5$ to g $_8$--.

Column 98, Line 56, Claim 15 "$R_x$" should read --Rx--.

Column 99, Lines 34 and 35, Claim 15 "a substituted an unsubstituted" should read --an unsubstituted--.

Column 100, Line 39, Claim 16 "$R_y$" should read --Ry--.

Column 100, Line 41, Claim 16 "$R_y$" should read --Ry--.

Column 100, Line 49, Claim 18 "11 cc" should read --11cc--.